United States Patent
Ogilvie

(10) Patent No.: US 12,290,443 B2
(45) Date of Patent: May 6, 2025

(54) IMPLANTABLE INTERPOSITIONAL ORTHOPEDIC PAIN MANAGEMENT

(71) Applicant: Ensemble Orthopedics, Inc., West Lake Hills, TX (US)

(72) Inventor: William F. Ogilvie, Austin, TX (US)

(73) Assignee: Ensemble Orthopedics, Inc., West Lake Hills, TX (US)

( * ) Notice: Subject to any disclaimer, the term of this patent is extended or adjusted under 35 U.S.C. 154(b) by 114 days.

(21) Appl. No.: 16/865,297

(22) Filed: May 1, 2020

(65) Prior Publication Data

US 2021/0338434 A1 Nov. 4, 2021

(51) Int. Cl.
| A61F 2/30 | (2006.01) |
| A61F 2/46 | (2006.01) |
| A61F 2/42 | (2006.01) |

(52) U.S. Cl.
CPC ........ *A61F 2/30721* (2013.01); *A61F 2/4606* (2013.01); *A61F 2002/30131* (2013.01); *A61F 2002/30301* (2013.01); *A61F 2002/30754* (2013.01); *A61F 2002/30892* (2013.01); *A61F 2002/4258* (2013.01)

(58) Field of Classification Search
CPC ................ A61F 2/30721; A61F 2/4606; A61F 2002/30131; A61F 2002/30301; A61F 2002/30754; A61F 2002/30892; A61F 2002/4258; A61F 2/3804; A61F 2/3872; A61F 2/4241; A61F 2002/30878; A61F 2002/30891; A61F 2002/4256
See application file for complete search history.

(56) References Cited

U.S. PATENT DOCUMENTS

| 730,284 A | 6/1903 | Monosmith |
| 2,642,862 A | 6/1953 | Jackson |
| 4,759,766 A | 7/1988 | Buettner-Janz et al. |
| 5,522,900 A | 6/1996 | Hollister |
| 5,645,605 A | 7/1997 | Klawitter |
| 5,702,472 A | 12/1997 | Huebner |

(Continued)

FOREIGN PATENT DOCUMENTS

| CH | 711485 A2 | 3/2017 |
| EP | 2364674 A1 | 9/2011 |

(Continued)

OTHER PUBLICATIONS

CMC APL Suspensionplasty With InternalBrace Ligament Augmentation, Surgical Technique Guide, Arthrex, 2019, 1 Ref. # LT1-00078-EN_C, pp. 1-8, URL: https://www.arthrex.com/resources/surgical-technique-guide/x-oqu9gc1uEGT-gFcDceb1w/cmc-apl-suspensionplasty-with-internalbrace-ligament-augmentation.

(Continued)

*Primary Examiner* — Brian A Dukert
*Assistant Examiner* — Melissa A Hoban
(74) *Attorney, Agent, or Firm* — KOKKA & BACKUS, PC

(57) ABSTRACT

Techniques for implantable orthopedic pain management devices are disclosed, including a saddle configured to axially align a top contoured surface to a bone surface and to axially align a bottom contoured surface to another bone surface, and a peripheral protrusion disposed on a peripheral surface of the saddle, the peripheral protrusion being configured to maintain dynamic stability of the saddle between the bone surface and the another bone surface.

19 Claims, 34 Drawing Sheets

(56) References Cited

U.S. PATENT DOCUMENTS

| | | | |
|---|---|---|---|
| 6,017,366 A | 1/2000 | Berman | |
| 6,436,146 B1 | 8/2002 | Hassler et al. | |
| 7,641,696 B2 | 1/2010 | Ogilvie et al. | |
| 7,837,739 B2 | 11/2010 | Ogilvie | |
| 8,012,217 B2* | 9/2011 | Strzepa | A61F 2/4202 623/21.18 |
| 8,100,979 B2 | 1/2012 | Felt et al. | |
| 8,292,954 B2 | 10/2012 | Robinson et al. | |
| 8,303,664 B1* | 11/2012 | Burstein | A61F 2/4225 623/20.14 |
| 8,764,830 B2 | 7/2014 | Robinson et al. | |
| 8,852,286 B2* | 10/2014 | Cook | A61F 2/30756 623/21.18 |
| 8,945,138 B2 | 2/2015 | Klotz et al. | |
| 9,237,958 B2* | 1/2016 | Duggal | A61B 17/1604 |
| 9,320,609 B2 | 4/2016 | Schon et al. | |
| 9,408,706 B2 | 8/2016 | Hassler et al. | |
| 9,572,673 B2 | 2/2017 | Hassler et al. | |
| 9,707,090 B2 | 7/2017 | DelSignore | |
| 10,064,739 B2* | 9/2018 | Duggal | A61B 17/1757 |
| 11,083,587 B2* | 8/2021 | Sikora | A61F 2/30756 |
| 11,642,226 B2 | 5/2023 | Ogilvie et al. | |
| 2002/0127264 A1* | 9/2002 | Felt | A61B 17/562 623/23.11 |
| 2004/0002768 A1* | 1/2004 | Parks | A61F 2/4202 606/87 |
| 2004/0143338 A1 | 7/2004 | Burkinshaw et al. | |
| 2004/0176773 A1 | 9/2004 | Zubok et al. | |
| 2004/0176844 A1 | 9/2004 | Zubok et al. | |
| 2005/0033426 A1 | 2/2005 | Ogilvie et al. | |
| 2005/0256577 A1 | 11/2005 | Baumgartner et al. | |
| 2006/0069446 A1* | 3/2006 | Ragusa | A61F 2/4225 623/18.11 |
| 2006/0241777 A1 | 10/2006 | Partin et al. | |
| 2006/0241778 A1 | 10/2006 | Ogilvie | |
| 2007/0100450 A1 | 5/2007 | Hodorek | |
| 2007/0123985 A1 | 5/2007 | Errico et al. | |
| 2008/0027250 A1 | 1/2008 | Link et al. | |
| 2008/0269908 A1 | 10/2008 | Warburton | |
| 2009/0012615 A1 | 1/2009 | Fell | |
| 2009/0254190 A1 | 10/2009 | Gannoe et al. | |
| 2010/0004743 A1 | 1/2010 | Strzepa et al. | |
| 2010/0057213 A1 | 3/2010 | Graham et al. | |
| 2010/0292800 A1 | 11/2010 | Zubok | |
| 2011/0106269 A1 | 5/2011 | Warburton | |
| 2011/0295379 A1 | 12/2011 | Shohat | |
| 2012/0046753 A1 | 2/2012 | Cook et al. | |
| 2012/0185056 A1 | 7/2012 | Warburton | |
| 2013/0079877 A1 | 3/2013 | Buma et al. | |
| 2013/0211530 A1 | 8/2013 | Mayer et al. | |
| 2014/0194999 A1 | 7/2014 | Orbay et al. | |
| 2014/0277552 A1 | 9/2014 | Burstein et al. | |
| 2014/0336652 A1 | 11/2014 | Christensen et al. | |
| 2015/0366672 A1 | 12/2015 | DelSignore | |
| 2016/0242920 A1 | 8/2016 | Parrott et al. | |
| 2016/0287407 A1 | 10/2016 | Patrick et al. | |
| 2017/0056181 A1 | 3/2017 | Rosenwasser et al. | |
| 2018/0193158 A1 | 7/2018 | Suddaby | |
| 2020/0171202 A1 | 6/2020 | Spence et al. | |
| 2021/0077265 A1 | 3/2021 | Garvey et al. | |
| 2021/0338433 A1 | 11/2021 | Ogilvie | |
| 2021/0338444 A1 | 11/2021 | Muir et al. | |
| 2021/0338451 A1 | 11/2021 | Ogilvie et al. | |
| 2021/0346166 A1 | 11/2021 | Sapio et al. | |
| 2022/0079768 A1 | 3/2022 | Hotchkiss et al. | |
| 2022/0202592 A1 | 6/2022 | Clarke et al. | |
| 2022/0249239 A1 | 8/2022 | Williams et al. | |
| 2023/0355395 A1 | 11/2023 | Ogilvie | |
| 2024/0023993 A1 | 1/2024 | Ogilvie | |
| 2024/0299175 A1 | 9/2024 | Ogilvie | |
| 2024/0299179 A1 | 9/2024 | Ogilvie | |

FOREIGN PATENT DOCUMENTS

| | | |
|---|---|---|
| EP | 3128934 B1 | 11/2019 |
| FR | 2883723 A1 | 10/2006 |
| WO | 2003007841 A2 | 1/2003 |
| WO | 2019022712 A1 | 1/2019 |
| WO | 2021222907 A2 | 11/2021 |
| WO | 2024186934 A1 | 9/2024 |

OTHER PUBLICATIONS

Hoban, Melissa A., Non-Final Office Action mailed Jan. 24, 2022 for U.S. Appl. No. 16/865,296.

Thomas, Shane, Notification of Transmittal of the International Search Report and the Written Opinion of the International Searching Authority, or the Declaration, mailed Dec. 2, 2021 for International Application No. PCT/US2021/030514.

Shih, Jessica G et al. "Comparison of Computed Tomography Articular Surface Geometry of Male Versus Female Thumb Carpometacarpal Joints." Hand (New York, N.Y.) vol. 13,1 (2018): 33-39. doi: 10.1177/1558944716688528.

Hoban, Melissa A., Final Office Action mailed Sep. 14, 2022 for U.S. Appl. No. 16/865,296.

Hoban, Melissa A., Non-Final Office Action mailed May 10, 2023 for U.S. Appl. No. 16/865,296.

Stewart, Alvin J., Non-Final Office Action mailed Oct. 11, 2022 for U.S. Appl. No. 16/865,299.

Matos, Taina, Notification of Transmittal of the International Search Report and the Written Opinion of the International Searching Authority, or the Declaration mailed Aug. 26, 2024 for International Application No. PCT/US2024/018735.

* cited by examiner

IMPLANTABLE INTERPOSITIONAL ORTHOPEDIC PAIN MANAGEMENT

FIELD

The present invention relates generally to implantable devices for medical and health-related purposes. More specifically, techniques for implantable interpositional orthopedic pain management are described.

BACKGROUND

Orthopedic pain is created by many different conditions including rheumatoid arthritis, traumatic arthritis, osteoarthritis, overuse, post-fracture deformation, bone loss (due to aging or use-related injuries) and others, all of which can result in substantial pain, loss of strength, or decreased ranges of motion. Pain can be caused due to severely weakened or degraded cartilage between bones, including those found in knee, hip, finger, metacarpal, carpometacarpal, and many other joints throughout the human body. Friction or physical contact between bones with missing, weakened, or degraded cartilage is a frequent source of pain, particularly in elderly persons. Consequently, orthopedic pain relief is a major field of research, endeavor, and investment.

Conventional techniques for relieving pain and restoring motion or improving a range of motion in some bodily joints typically require the removal of degraded cartilage and bones, fusing of joints, or other highly invasive surgical procedures that can often be counterproductive to biomechanical restoration of movement and future usefulness of degraded bodily joints. Fusion of bones in some bodily joints is also problematic because further use and range of motion are eliminated or severely limited. Also, conventional solutions are problematic and can lead to the transmission of pain from a joint through bones that are fused, which is typically a time (due to surgical operating time and post-surgical rehabilitation) less costly procedure than attempting joint repair or restoration. Further, conventional surgical techniques to alleviate pain in a joint often point away from removing bones or portions thereof, which limits effectiveness, minimizes pain relief and pain management, and restoration of joint stability and ranges of motion. Other conventional solutions often remove bone or parts thereof, such as ligament removal and tendon interpositioning ("LRTI") remove bone or portions thereof such as removing a trapezium when attempting to surgically effect pain relief in joints such as the carpometacarpal ("CMC") joint, which can leave gaps and undesirable large joint spaces. These conventional solutions do not typically achieve joint stability or restore range of motion or strength to a degree of normal articulation and use.

Other problematic conventional solutions rely upon the use of implantable devices. Due to large numbers of ligaments, connective tissue, and bone presence, conventional techniques for the placement of implantable devices can result in cutting connective and non-connective tissue, tendons, muscle, and ligaments that do not naturally restore easily post-surgery. Many implantable devices are made of materials that are problematic as long-term options for effecting orthopedic pain relief and range of motion restoration. For example, implantable devices such as ball-and-socket artificial joints made of cobalt chrome or other metals or alloys can erode surrounding bone or cause friction resulting in bone erosion over time. Further, conventional placement of implantable devices in bodily joints typically require substantial alterations to bones and bone structures by cutting off ends, portions, or removing bones entirely. Conventional techniques are hampered due to the sacrifice of function in exchange for pain relief and are limited in offerings to a user seeking to regain normal strength and range of motion.

Thus, what is needed is a solution for orthopedic pain management using implantable medical devices without the limitations of conventional techniques.

BRIEF DESCRIPTION OF THE DRAWINGS

Various embodiments or examples ("examples") of the invention are disclosed in the following detailed description and the accompanying drawings.

DETAILED DESCRIPTION

Various embodiments or examples may be implemented in numerous ways, including as a device, a system, a process, an apparatus, or an article of manufacture. Processes generally may be varied in individual operations, processes, or sub-processes may be performed in an arbitrary order, unless otherwise provided in the claims.

A detailed description of one or more examples is provided below along with accompanying figures. This detailed description is provided in connection with such examples, but is not limited to any particular example. The scope is limited only by the claims and numerous alternatives, modifications, and equivalents. Numerous specific details are set forth in the following description in order to provide a thorough understanding. These details are provided for the purpose of illustrating various examples and the described techniques may be practiced according to the claims without some or all of these specific details. For clarity, technical material that is known in the technical, medical, and industrial fields and related to the exemplary subject matter has not been described in detail to avoid unnecessarily obscuring the description or providing unnecessary details that may be already known to those of ordinary skill in the art.

Figure 1A:
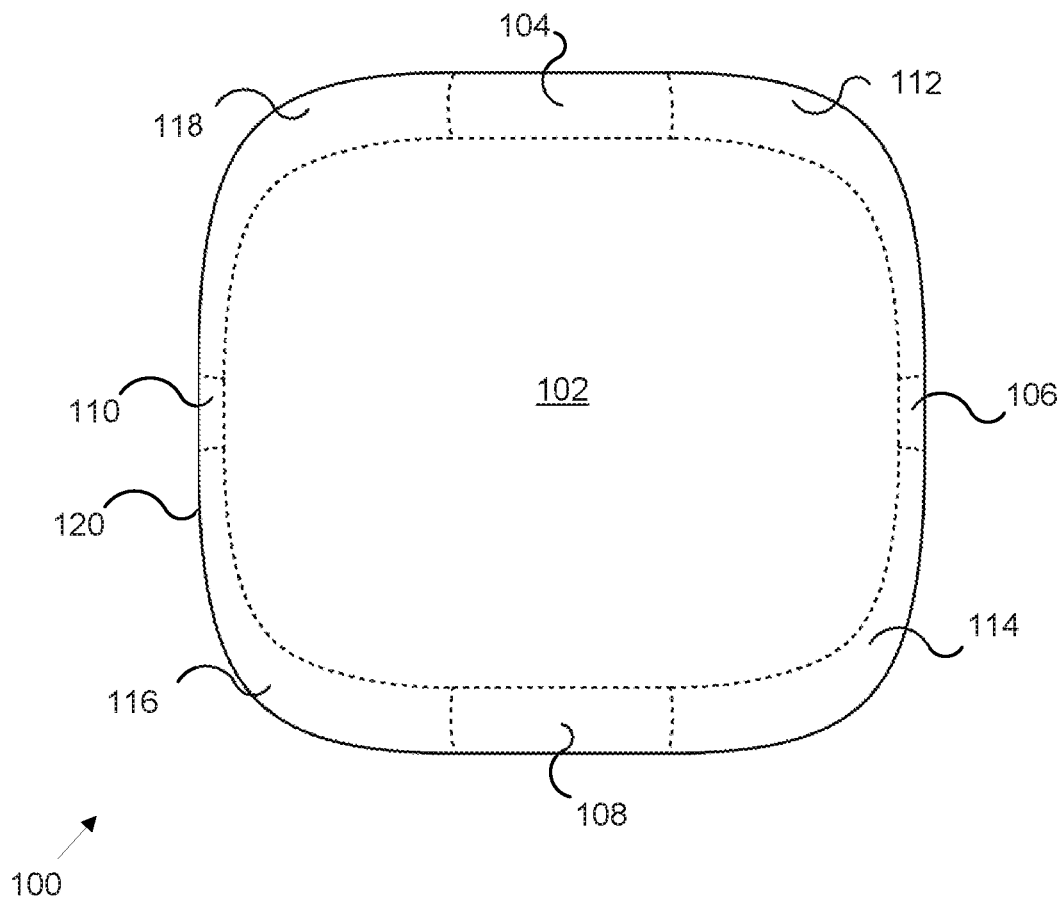
FIG. 1A illustrates a top view of an exemplary implantable interpositional orthopedic pain management apparatus.

FIG. 1A illustrates a top view of an exemplary implantable interpositional orthopedic pain management apparatus. Here, a top view is shown of device 100, which includes interpositional saddle surface 102, saddle channel openings 104-110, peripheral protrusions 112-118, and periphery 120 (collectively "elements 102-120"). As used herein, like numbered and/or like named elements are assumed to be referencing the same or a substantially similar element having the same or substantially similar function or structure. As used herein, the term "saddle" may be used to refer to any implementation of device 100, which is not limited to symmetrical, asymmetrical, off-centered, centered, aligned, or other specific geometric shapes or properties. A "saddle" may be implemented using various shapes that may be concave or convex and are not required to be aligned symmetrically around any dimensional axis (not shown) shown or described throughout, but can be axially aligned, anatomically aligned (i.e., aligned about a joint, bone, or other anatomical structure, without limitation or restriction), or aligned differently, without limitation or restriction. The term "saddle" may be used to refer, in some examples, to a body of device 100 that is configured to receive, fit, conform, or otherwise be positioned or placed on, over, under, or between one or more bones. Some of these shapes may be varied such that device is saddle-shaped or substantially saddle-shaped implementation. In some examples, device 100 may be an implantable medical device (as used herein, "implantable medical device," "implantable device," "implant device," "implant," and "device" are interchangeable terms that may be used to refer to, for example, device 100, without limitation or restriction) configured for orthopedic pain relief in various types of joints such as the carpometacarpal joint, knee joint, elbow joint, or any other type of joint where two or more bones form a cartilaginous joint in which device 100 may be implanted or disposed (hereafter "implanted," "inserted," "surgically inserted,"

"positioned," "oriented," or "placed," may be used interchangeably with "disposed"). As shown, device 100 may be formed as a monolithic structure or as a composite of structures and/or sub-structures that, when combined, form an integrated implantable device that may be appropriately sized for a particular joint (or type of joints) to distract bones adjacent to a joint to prevent direct or indirect physical contact, thus alleviating pain and providing dynamic stability to the joint as well as restoring or maintaining a desired range of motion. Also, degraded (due to age-related wear or other biological deterioration) or damaged cartilage (e.g., resulting from a traumatic injury) may be replaced partially or fully using device 100.

Here, device 100 is configured structurally to contour to bone ends (e.g., distal or proximal ends of bones that have various contoured surfaces that may be convex, concave, or otherwise). For example, in a carpometacarpal joint (hereafter referred to as the "CMC joint"), a trapezium bone ("trapezium") and a metacarpal bone ("metacarpal") form a joint surrounded by a synovial capsule in which there may be cartilage. When used to replace degraded, deteriorated, or missing cartilage in the CMC joint, device 100 may be structurally configured with a concave surface such as interpositional saddle surface 102, which may be configured with a curvature attribute (e.g., one or more types of radii (e.g., spline, toroidal (e.g., elliptical, spline, donut, or other toroidal shapes), ellipse, or others, without limitation or restriction)) that is larger than that of, for example, a bone associated with a joint targeted for the implant within a given patient. In other examples, a curvature attribute (e.g., radius or radii of curvature) may be substituted with other units or attributes of measurement such as splines, As used herein, "larger" may refer to an attribute associated with the sizes and shapes of device 100 and interpositional saddle surface 102 (or other interpositional saddle surfaces or other features of device 100 and others such as those described herein) as determined by a range of size measurements of various bones forming different types of joints and standards of deviation. In some examples, the term "interpositional" as used herein may refer to an intended function and/or structure of device 100 as a "spacer" or intermediate implantable medical device that is designed to interpose between bones in a joint in order to alleviate pain, prevent distraction of bones from each other, and prevent or reduce loss of articulating motion and/or ranges of motion associated with a joint having missing and/or damaged cartilage. Here, device 100 may be configured for insertion into joints such as the CMC in order to relieve pain (e.g., due to injury, wounds, degradation, aging, arthritis, or other causes) while avoiding invasive and destructive procedures such as bone removal and/or joint fusion.

For example, device 100 may be formed (i.e., made, manufactured, molded, synthesized, built, generated, or the like) to different sizes of joints using various types of materials. Materials such as alloys, ceramics, ceramic-like, or polymers (e.g., thermoplastics, polycarbonate, polycarbonate urethanes ("PCU"), carbon chrome, pyrolytic carbon, polycarbon, polyetheretherketone ("PEEK"), polyetherketone ("PEK"), polyetherketoneketone ("PEKK"), polyurethane, or others, without limitation or restriction) may be used to form device 100. Also, materials may be organic, inorganic, synthetic, or natural when forming device 100, elements 102-120, and the other examples provided herein, regardless of manufacturing processes or techniques. In some examples, other attributes of device 100 may be varied before, during, or after formation. For example, device 100 may be implemented with attributes to determine the type of material to be used. In some examples, materials having an elastic modulus or moduli that is similar or substantially similar to that of bone may be used. In other words, some implementation examples of device 100 (and the other examples of devices similar or substantially similar to device 100 as described below) may be designed, formed, or otherwise implemented using materials that present attributes, characteristics, and properties (e.g., elastic modulus (i.e., elasticity), flexibility, permeability, porosity, strength, tensile strength, tensile/compressive moduli or others, without limitation or restriction) that are similar or substantially similar to those of cortical bone and bone matrix (e.g., materials that exhibit properties such as elastic moduli similar or substantially similar to cortical bone). In other examples, materials for forming device 100 may be selected based on attributes and properties of materials that are similar, substantially similar, or less than that of cortical bone and cortical bone matrix in order to prevent damage to surrounding bones during implantation. For example, material for forming device 100 may be selected with a low enough elastic moduli such that implantation may occur by folding or partially deforming device 100 for insertion through an incision in a synovial capsule and an enlarged opening into a joint. Once inserted, device 100 made of materials such as those described above, may have a sufficient low modulus (property of elastic moduli such that it recovers and restores into its originally formed shape once positioned within a joint. The above examples are provided solely for purposes of illustrating a variety of materials that may be used to implement device 100 and the other implementation examples provided herein, without limitation or restriction to any particular type of material, whether found in nature or synthesized in artificial manufacturing processes. As used herein, different types of materials may be used and are not limited to the examples above.

Sizes may be determined based on median measurements of bone structures and features such as radii of curvature of tori found at either the distal or proximal ends of the bone structures. To provide tolerance for sizing implants for various joint sizes, one or multiple standards of deviation of measurements may also be taken into account when forming device 100. For a CMC joint of a given patient, in some examples, interpositional saddle surface 102 may be formed having a radius of curvature that is designed to fit over the proximal or distal end of a trapezium, metacarpal, tibia, femur, or other type of bone that couples to another bone over one or more joints. A "channel" or length of curvature traversing horizontally through interpositional saddle surface 102 may, in some examples, extend between saddle channel openings 106 and 110. Thus, curved surfaces rising up the sides of a saddle channel between saddle channel openings 106-110 along interpositional saddle surface 102 may be formed with a radius of curvature that, when measured, may be one or two standard deviations apart from the measured radius of curvature of a bone end (i.e., distal or proximal end of a bone or bone structures such as those mentioned above) over which device 100 has been configured to "fit" when disposed within a joint. In other words, when device 100 is implanted within a synovial capsule (the term "synovial capsule" may be used interchangeably with "capsule" and may refer to an anatomical structure or feature surrounding a joint in which bone, cartilage, or other anatomical elements or features may be found), interpositional saddle surface 102 is designed (i.e., structured, formed, or configured) to contour to a corresponding surface of a bone. As an example, device 100 may be implanted into a CMC joint (not shown). When inserted, interpositional saddle surface 102 may be positioned over the end (e.g., proximal or distal) of the metacarpal or trapezium bones (not shown) adjacent to and forming the CMC joint. Formed having a radius of curvature that is one, two, or other standard deviations from a measured radius of curvature of a patient's metacarpal or trapezium, interpositional saddle surface 102 may be a concave channel traversing the distance between saddle channel openings 106 and 110 and configured to receive the end (e.g., distal or proximal) of a metacarpal, trapezium, or other bone of a joint. For example, anthropometric data may be used to determine a given radius of curvature and 1, 2, 3, or more standard deviations when forming device 100 in order to ensure interpositional saddle surface 102 has a radius of curvature that exceeds the radius of curvature of any bone adjacent to the joint.

In some examples, a channel (e.g., as formed by interpositional saddle surface 102 and saddle channel openings 106 and 110) may be disposed on one side of device 100 instead of having multiple channels on opposite sides. In other words, device 100 may be varied to have a single channel to receive the head or torus of a single bone of a joint as opposed to multiple channels configured to receive opposing bones. As shown in the present example, FIG. 1A illustrates an example of device 100 having multiple channels, but there may be examples where cartilage is present within a synovial capsule and joint in such quantity as to require only a single channel implementation of device 100.

Alternatively, another channel, an example of which is described below in connection with FIG. 1B, may be formed between saddle channel openings 104 and 108. Saddle channel openings 104 and 108, in some examples, may be disposed at either end of another saddle channel (not shown) that may be axially offset from the saddle channel formed by interpositional saddle surface 102 between saddle channel openings 106 and 110. Another saddle channel (not shown) may be disposed on the opposite surface of interpositional saddle surface 102 and configured to receive the end of an opposing bone (e.g., trapezium or metacarpal) forming a joint (not shown) with the bone received by interpositional saddle surface 102, as described in greater detail below in connection with FIG. 1B.

Referring back to FIG. 1A, an outer perimeter of device 102 (e.g., periphery 120) may have one or more peripheral protrusions 112-118 formed (e.g., molded, made, integrated, incorporated, included, or otherwise disposed) and disposed at different locations along periphery 120. As shown from a top view, a cross section (not shown) of device 100 along a horizontal (i.e., x-axis) plane may, in some examples, be substantially rectangular in shape, particularly if a cross-sectional view is of a horizontal plane disposed between interpositional saddle surface 102 and interpositional saddle surface 132 (FIG. 1B)). Axes, as presented throughout this description, may be aligned along the length, width, cross-axially, anatomically aligned, or aligned otherwise, without limitation or restriction. In some examples, axes (as referred to herein) may refer to one or more axes that may run the length, width, diagonal, or in other directions aligned with one or more bones of a joint. For example, one axis may run lengthwise through a tibia, while another axis may also run lengthwise through a femur, and still another set of axes may be used for orientation associated with a joint or bone(s) (i.e., "anatomical alignment"). In other words, axes may or may not correspond to a set of three (3) dimensional axes that are orthogonal to each other, but are instead determined based on a joint and the bones that form said joint. An axis associated with a given bone may or may not necessarily also be aligned with another one of a joint. Axes may also be determined differently and are not limited to examples described.

In other examples, the positions of peripheral protrusions 112-118 may be varied, without limitation or restriction. For example, here, peripheral protrusions 112-118 are substantially positioned at the corner regions of device 100 along periphery 120. Peripheral protrusions 112-118 may be configured (i.e., when device 100 is inserted into a synovial capsule of a joint) to be positioned at non-articulating regions of a joint (not shown), but may be shaped in various configurations to maintain and prevent expulsion of device 100 from within the joint. In other examples, the positioning, number, shape, configuration, design, material, or other aspects, without limitation or restriction to the examples described. In other examples, device 100 and elements 102-120 may be designed, configured, formed, modified, or implemented apart from the examples shown or described and are not limited to those provided.

Figure 1B:
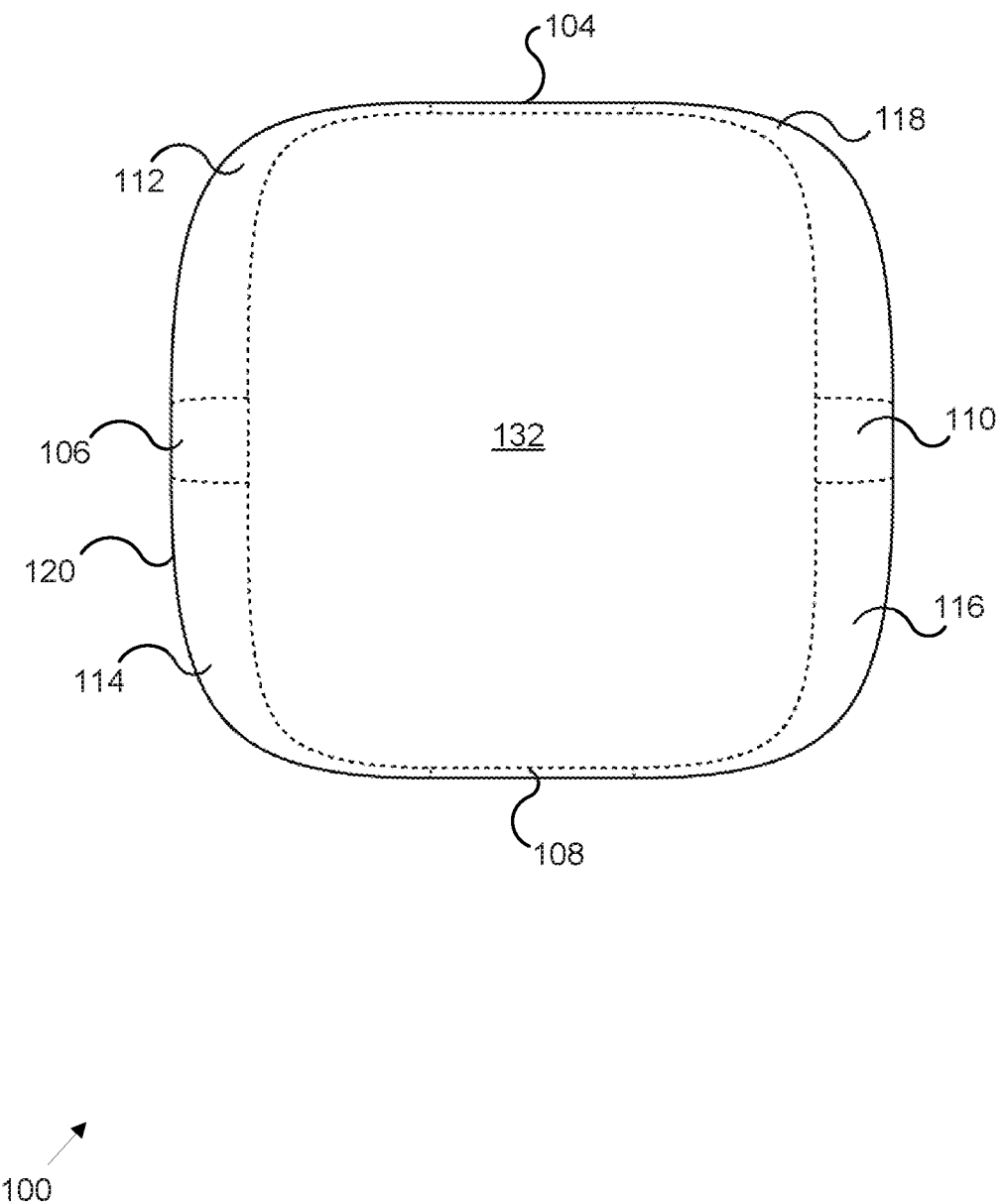
FIG. 1B illustrates a bottom view of an exemplary implantable interpositional orthopedic pain management apparatus.

FIG. 1B illustrates a bottom view of an exemplary implantable interpositional orthopedic pain management apparatus. Here, a bottom view is shown of device 100, which includes saddle channel openings 104-110, peripheral protrusions 112-118, and periphery 120, and interpositional saddle surface 132, (collectively "elements 102-132"). As used herein, like numbered and/or like named elements are assumed to be referencing the same or a substantially similar element having the same or substantially similar function or structure. Differences in function or structure may be described separately with regard to a specific feature described. In some examples, another saddle channel may be formed with interpositional saddle surface 132, and saddle channel openings 104 and 108. As described above, an interpositional saddle channel disposed between saddle channel openings 104 and 108 along interpositional saddle surface 132 may be a partially or entirely concave feature of device 100 that is configured to receive a bone (opposite to another bone received by interpositional saddle surface 102 ((FIG. 1A)). In some examples, the heads (e.g., torus) of each bone, when received by interpositional saddle surfaces 102 and 132, may be axially offset from or aligned with each other, without limitation or restriction. Interpositional saddle surface 102 and 132 may be orthogonal or substantially orthogonal to each other. In other examples, interpositional saddle surface 102 and 132 may be axially offset, along one or more different axes, by more or less than 90 degrees.

As shown, interpositional saddle surface 102, in some examples, may have a cross sectional shape with a radius of curvature (which may be of various sizes) that is structured to receive a bone adjacent to a joint into which device 100 may be inserted. Also, as described above, a cross-section of a plane disposed substantially parallel to an axis of each interpositional saddle channel running between saddle channel openings 104 and 108 and 106 and 110, respectively. A cross-section of a plane that is substantially orthogonal to a plane lying parallel to interpositional saddle surface 102 (FIG. 1A) and interpositional saddle surface 132 (FIG. 1B) may be substantially rectangular in shape. In other examples, the shape, cross-section, or other dimensional attributes of device 100 may be varied and is not limited to those shown and described.

In some examples, peripheral protrusions 112-118 may be disposed at substantially corner positions of periphery 120 to provide sub-structures molded into periphery 120 that are configured to maintain a given position and/or orientation of device 100 within a joint. Although shown disposed at substantially corner positions of periphery 120, peripheral protrusions 112-118 may be formed at different positions, angles, attitudes, or other varying attributes along periphery 120. Here, device 100 includes peripheral protrusions 112-118 that are configured for disposition within non-articulating regions when device 100 is inserted and oriented within a synovial capsule and joint. Peripheral protrusions 112-118, in some examples, are configured to maintain device 100 within one or more tolerances of fit within a joint to prevent physical contact (i.e., relieving or lessening pain by doing so) between one or more bones of a joint, but also to maintain position within a joint and prevent expulsion, partially or fully, of device 100. In other examples, device 100 and elements 102-132 may be designed, configured, formed, modified, or implemented apart from the examples shown or described and are not limited to those provided.

Figure 1C:
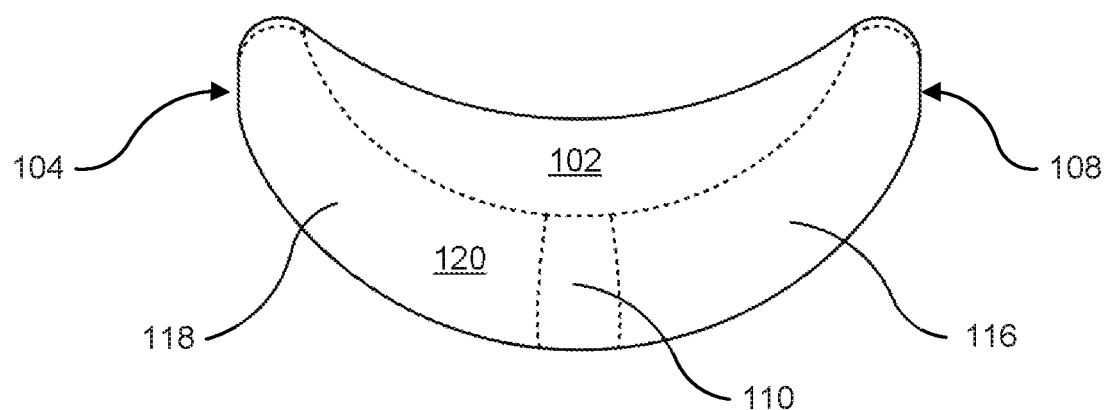
FIG. 1C illustrates an anterior view of an exemplary implantable interpositional orthopedic pain management apparatus.

FIG. 1C illustrates an anterior view of an exemplary implantable interpositional orthopedic pain management apparatus. Here, an anterior or frontal view of device 100 includes interpositional saddle channel surface 102 (showing a substantially concave contour), channel openings 104, 108 and 110 (peripheral protrusions 104 and 108 being used to form a saddle channel (i.e., a channel or contoured surface, concave or convex, configured to receive the end, head, torus, or other portion of a bone adjacent to a joint into which device 100 is surgically implanted, inserted, or otherwise disposed, regardless of surgical technique) with surface 132 (as described in connection with FIG. 1B above)), and peripheral protrusions 116-118 disposed along periphery 120. As used herein, like numbered and/or like named elements are assumed to be referencing the same or a substantially similar element having the same or substantially similar function or structure. Differences in function or structure may be described separately with regard to a specific feature described. In some examples, when device 100 is inserted into a synovial capsule or into a joint, a bone adjacent to the joint may be received by interpositional saddle surface 102. As an example, saddle surface 102 may be disposed on one side or another of device 100 in order to provide a channel (i.e., a regularly, irregularly, symmetrical, asymmetrical, or other contoured surface that may or may not be substantially concave, convex, or shaped differently) configured to receive a torus or other portion of a bone in order to provide an intermediate structure designed to prevent one bone of a joint from contact another bone in the same joint in order to prevent or alleviate pain (i.e., pain management).

Once inserted and positioned within a joint, device 100 may be configured to remain in place by disposing peripheral protrusions 116-118 in non-articulating regions of a joint (i.e., between two or more bones). As a joint is articulated (not shown), device 100, as shown in FIG. 1C, may be used to receive the end of a bone in direct or indirect or "floating" (i.e., intermittent) contact with interpositional saddle surface 102. Periphery 120, which forms an integrate perimeter of device 100, including peripheral protrusions 116-118, which may be substantially smooth or shaped with structures (as shown in FIGS. 2-4 below) configured to maintain device 100 within a joint (i.e., prevent expulsion of device 100 by providing structures (e.g., peripheral protrusion 116-118) that are configured to maintain the position of device 100 between two or more articulating bones. Saddle channel opening 110 may be shaped (e.g., configured with a radius of curvature that is larger than that of a bone intended to be received within interpositional saddle surface 102) to receive the end, head, torus, or other portion of a bone when surgically implanted into a joint (e.g., inserting through a surgically-created opening in a synovial capsule surrounding a joint). Likewise, saddle channel openings 104 and 108 may be implemented similarly or differently.

Also shown in FIG. 1C are saddle channel openings 104 and 108, which may be axially (e.g., symmetrically) or not axially (e.g., asymmetrically) aligned to provide another saddle channel (as described below in connection with FIG. 1D) to receive the head, end, torus or other portion of an opposing or another bone when device 100 is surgically implanted. For example, when device 100 is surgically implanted in a CMC joint, interpositional saddle surface 102 and saddle channel opening 110 may be configured to receive a torus of a metacarpal bone. In some examples, saddle channel openings 104 (not shown) and 108 may be configured to receive an opposing end, head, torus, or portion of a trapezium bone and, once implanted, device 100 may be configured in function and shape to provide an intermediate implantable device (e.g., device 100) to manage, relieve, or prevent pain by preventing a trapezium and metacarpal bones from direct or indirect contact. As described herein, device 100 may be used to replace deteriorated, damaged, injured, worn, partially or wholly lost cartilage in a CMC or other joint, without restriction or limitation.

In other examples, device 100 and the elements shown and described may be designed, configured, formed, modified, or implemented apart from the examples shown or described and are not limited to those provided.

Figure 1D:
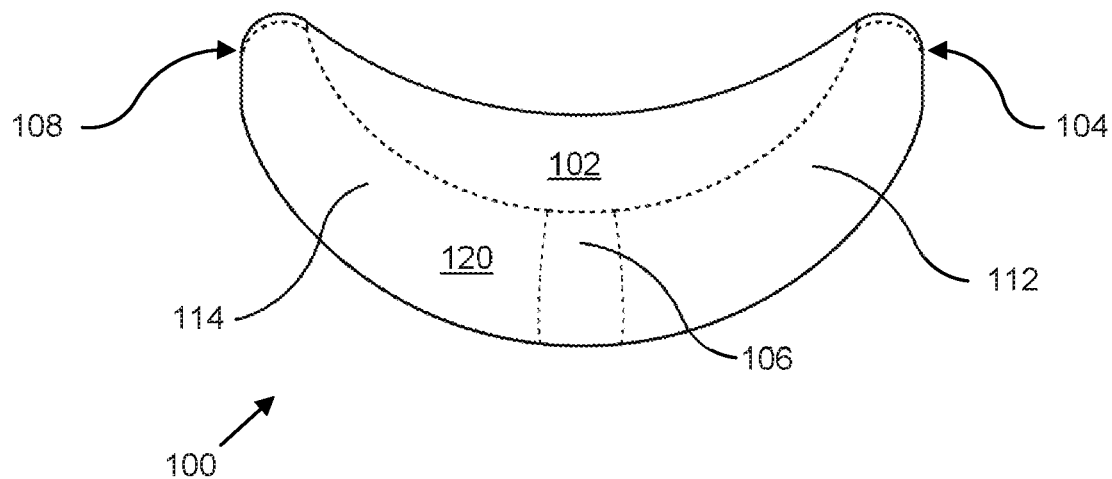
FIG. 1D illustrates a posterior view of an exemplary implantable interpositional orthopedic pain management apparatus.

FIG. 1D illustrates a posterior or rear view of an exemplary implantable interpositional orthopedic pain management apparatus. Here, a posterior or rear view of device 100 includes interpositional saddle channel surface 102 (showing a substantially concave contour substantially opposite to that shown in FIG. 1C), channel openings 104-108 (channel openings 106-108 may be used to implement a saddle channel with interpositional saddle channel surface 102 (as described above in connection with FIG. 1A)), and peripheral protrusions 112-114 disposed along periphery 120. As used herein, like numbered and/or like named elements are assumed to be referencing the same or a substantially similar element having the same or substantially similar function or structure. Differences in function or structure may be described separately with regard to a specific feature described. For example, although interpositional saddle surface 102 is shown as substantially concave, in other examples, different shapes, contours, structures, or features may instead be implemented. As an example, interpositional saddle surfaces 102 and 132 (FIG. 1B) may be convex and/or concave, in entirety or partially. In other examples, interpositional saddle surfaces 102 and 132 (FIG. 1B) may also be substantially flat or planar or the degree of concavity or convex curvature (i.e., radii of curvature) may be altered to varying degrees. Still further, concave, convex, flat, planar, or other surface contouring may be symmetrically or asymmetrically oriented around a vertical axis (not shown) of device 100.

As shown and described, the posterior or rear view of device 100 also illustrates interpositional saddle surface 102, saddle channel openings 104-108 (for interpositional saddle surface 132 (not shown)), and peripheral protrusions 112-114 disposed along periphery 120. As described above, device 100 and the elements shown may be implemented in structure and function similarly to device 100 as shown and described above in connection with FIGS. 1A-1C. In other examples, device 100 may include variations in function and/or structure such as having a saddle channel (i.e., interpositional saddle surface 102 extending between saddle channel openings 106 and 110 (FIG. 1C)) on a single side of device 100. In other examples, device 100 may be implemented such that saddle channels may be disposed on adjacent sides or surfaces instead of being disposed on substantially opposite sides of device 100. In still other examples, device 100 and the elements shown and described may be designed, configured, formed, modified, or implemented apart from the examples shown or described and are not limited to those provided.

Figure 1E:
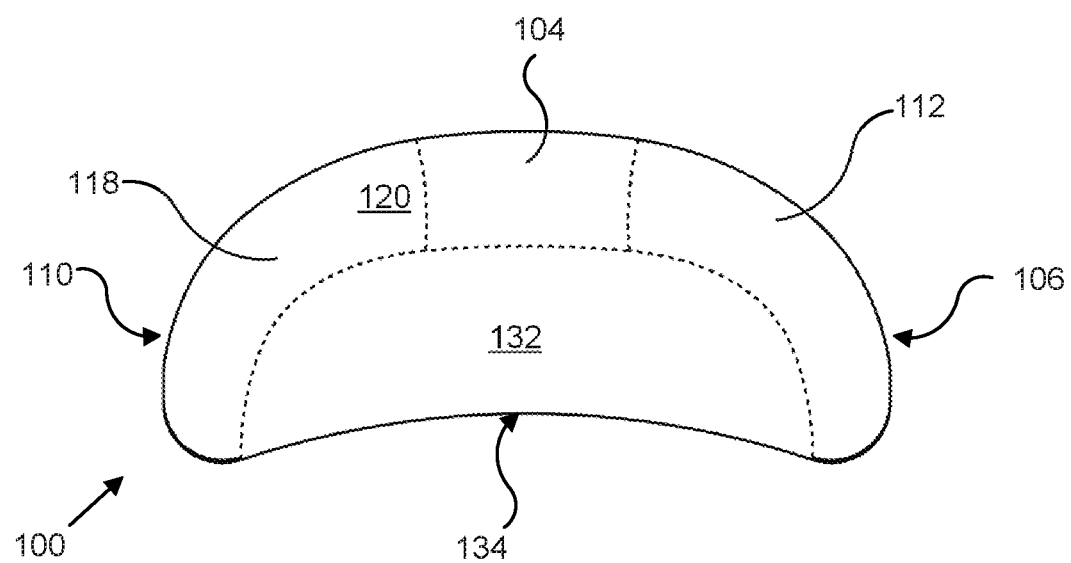
FIG. 1E illustrates a left view of an exemplary implantable interpositional orthopedic pain management apparatus.
Figure 1F:
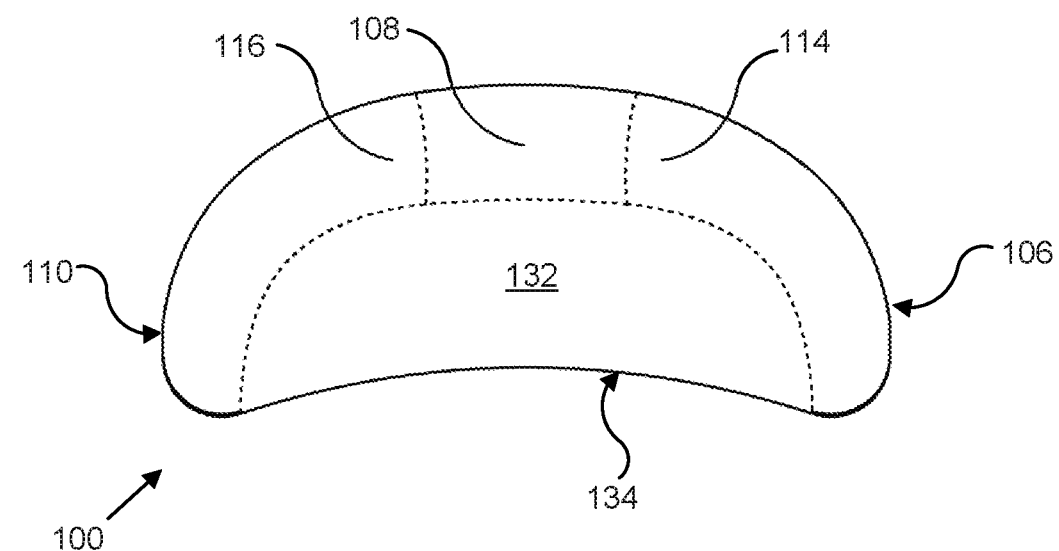
FIG. 1F illustrates a right view of an exemplary implantable interpositional orthopedic pain management apparatus.

FIG. 1E illustrates a left view of an exemplary implantable interpositional orthopedic pain management apparatus. Here, a left view is shown of device 100 (i.e., an example of an implantable interpositional orthopedic pain management apparatus), which includes saddle channel openings 104-106 and 110, peripheral protrusions 112 and 118 disposed along and formed with periphery 120, interpositional saddle surface 132, and outer surface 134 (collectively "elements 102-132"). As described herein, like numbered and/or like named elements are assumed to be referencing the same or a substantially similar element having the same or substantially similar function or structure. Differences in function or structure may be described separately with regard to a specific feature described. In some examples, outer surface 134 may be shaped, curved, contoured, or otherwise formed to have a radius of curvature that is configured to receive a bone adjacent to a joint in which device 100 is surgically implanted. As shown, interpositional saddle surface 132 may be configured substantially orthogonal and opposing to interpositional saddle surface 102 (FIG. 1A) and used to receive a bone other than that received by a channel formed by interpositional saddle surface 102 and saddle channel openings 106 and 110. If implanted in a CMC joint, for example, interpositional saddle surface 132 may be configured with outer surface 134 having a radius of curvature that is one, two, or more standard deviations of width, depth, or other dimensions in order to receive a trapezium bone. A trapezium, when inserted into a channel formed by interpositional saddle surface 132 and saddle channel openings 104 and 108, may be configured to receive a trapezium bone. Further, another channel on substantially an opposing side of device 100 may be formed with interpositional saddle surface 102 and saddle channel openings 106 and 110 and configured to receive a metacarpal bone. In other examples, device 100 and elements 102-134 may be designed, configured, formed, modified, or implemented apart from the examples shown or described and are not limited to those provided.

FIG. IF illustrates a right view of an exemplary implantable interpositional orthopedic pain management apparatus. Here, a right view is shown of device 100, which includes saddle channel openings 106-110, peripheral protrusions 114-116 formed in periphery 120, and interpositional saddle surface 132 with outer surface 134 (collectively "elements 102-132"). As used herein, like numbered and/or like named elements are assumed to be referencing the same or a substantially similar element having the same or substantially similar function or structure. Differences in function or structure may be described separately with regard to a specific feature described. In some examples, the above-described elements are similar to those previously described and device 100 is shown from a right-side view illustrating interpositional saddle surface 132 with saddle channel opening 108 being configured to receive a bone (e.g., trapezium, metacarpal, tibia, ulna, or others, without limitation or restriction). As described above in connection with FIG. 1E, outer surface 134 may be formed as part of interpositional saddle surface 132 with a radius of curvature configured to receive another bone. In other examples, the radius of curvature of outer surface 134 and interpositional saddle surface 132 may have a different or no curvature of radius. In other words, device 100 may be implemented with a channel on a single side and used to instead have a substantially flat surface for outer surface 134 when inserted into a joint. In other examples, device 100 and elements 102-134 may be designed, configured, formed, modified, or implemented apart from the examples shown or described and are not limited to those provided.

Figure 1G:
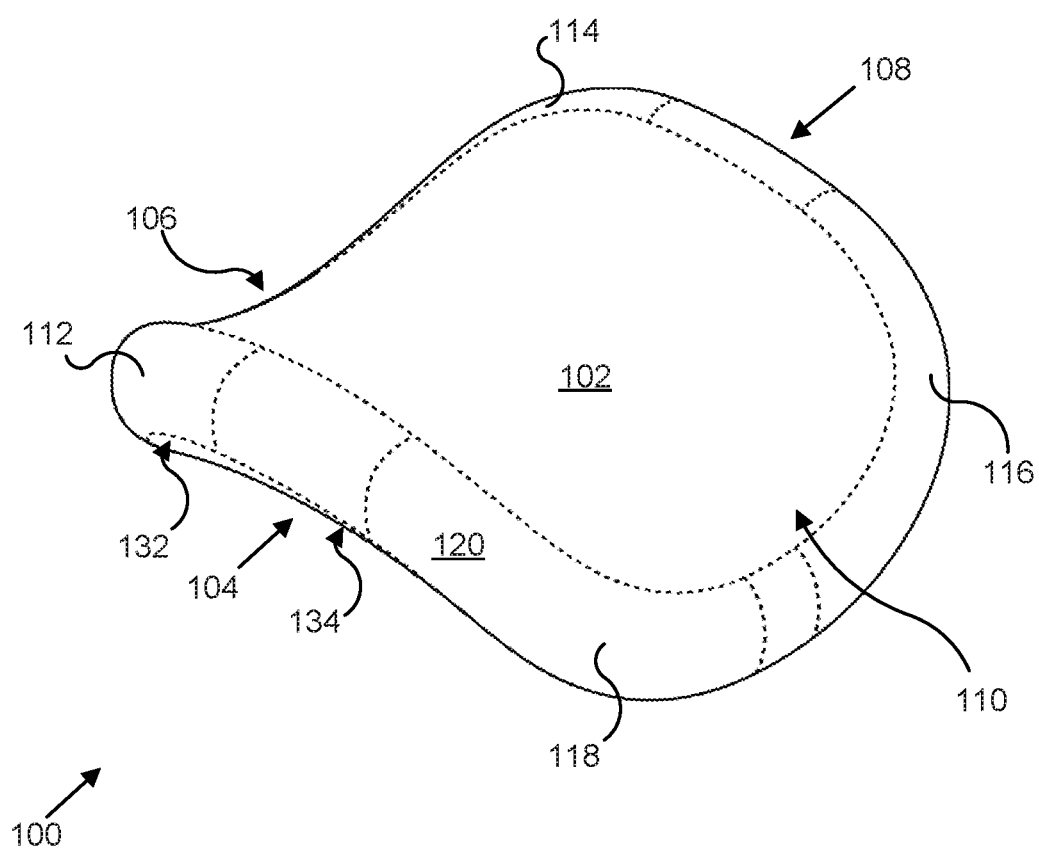
FIG. 1G illustrates a perspective view of an exemplary implantable interpositional orthopedic pain management apparatus.

FIG. 1G illustrates a perspective view of an exemplary implantable interpositional orthopedic pain management apparatus. Here, a perspective view of device 100 is shown including interpositional saddle surface 102, saddle channel openings 104-110, peripheral protrusions 112-118, periphery 120, interpositional saddle surface 132, and outer surface 134 of interpositional saddle surface 132. As used herein, like numbered and/or like named elements are assumed to be referencing the same or a substantially similar element having the same or substantially similar function or structure. Differences in function or structure may be described separately with regard to a specific feature described. In some examples, saddle channel openings 104-110 may refer to those portions or regions of device 100 that have substantially concave surfaces and are designed to act as openings for receiving, for example, heads, portion, torus, or other parts of bones into interpositional saddle surfaces 102 and 132. In other examples, as described above, the radius of curvature of interpositional saddle surfaces 102 and/or 132 may be varied and alternatively have a flat or substantially flat surface on one side. In some examples, when device 100 is formed, interpositional saddle surfaces 102 and 132 may be configured to have flat, curved, concave, convex, or multi-faceted (i.e., having concave and convex surfaces disposed over interpositional saddle surfaces 102 or 132) structures or sub-structures. As described in greater detail below, peripheral protrusions 112-118 may be configured for placement within a joint to receive adjacent bones (and prevent them from contact). Device 100, in some examples, is substantially maintained in position and prevented from expulsion due to peripheral protrusions 112-118 disposed at various points along periphery 120. Thus, regardless of how a joint or bones are manipulated along various axes (e.g., abduction-adduction, flexion-extension, supination-pronation, and others) whether due to active manipulation of a joint (e.g., active motion) or passive motion (i.e., motion that may occur when the joint or bones adjacent thereto are not being directly manipulated, but instead have motion imparted to them due to other proximal or distal anatomical motion or activity), device 100 may be prevent from expulsion by one or more of peripheral protrusions 112-118 coming into contact with an articulating or non-articulating structure that keeps device 100 in position. In other examples, device 100 and elements 102-134 may be designed, configured, formed, modified, or implemented apart from the examples shown or described and are not limited to those provided.

Figure 2A:
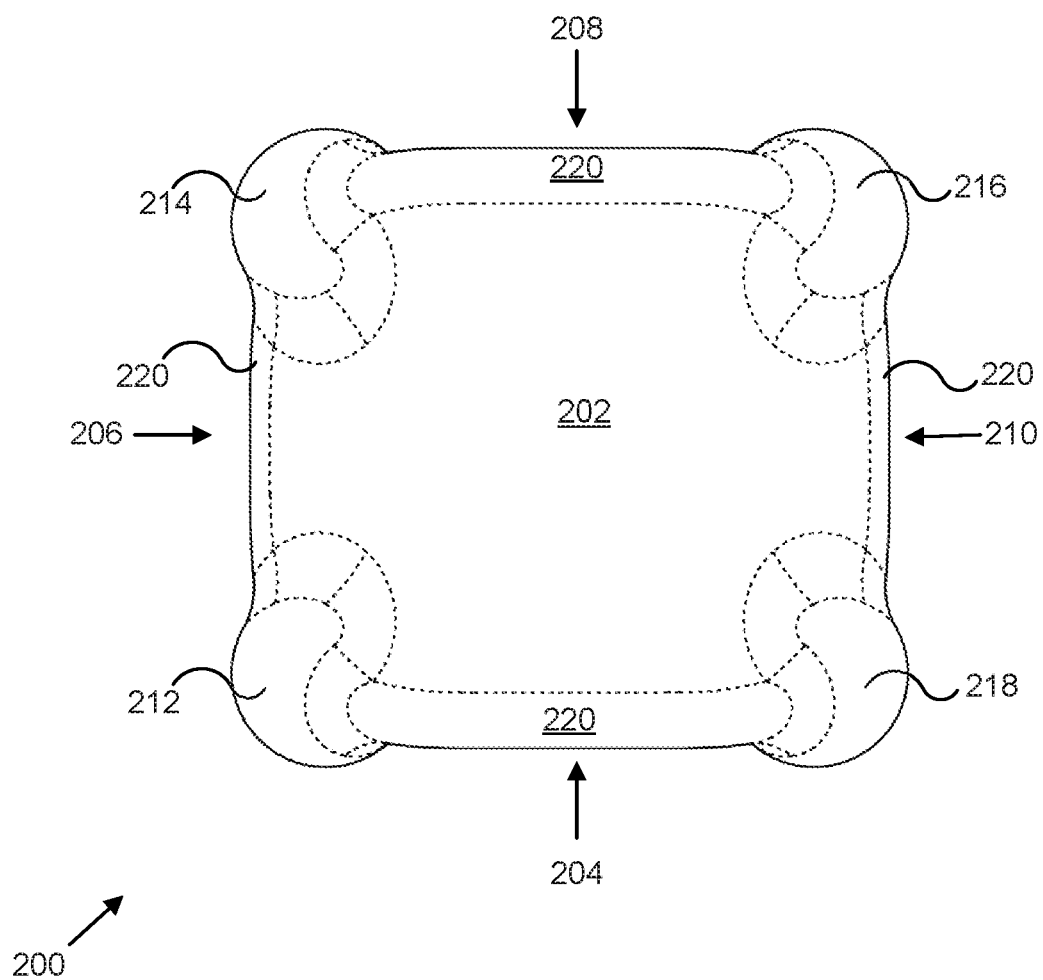
FIG. 2A illustrates a top view of an exemplary implantable interpositional orthopedic pain management apparatus.

FIG. 2A illustrates a top view of an exemplary implantable interpositional orthopedic pain management apparatus. Here, device 200 includes interpositional saddle surface 202, saddle channel openings 204-210, peripheral protrusions 212-218, and periphery 220. As used herein, like numbered and/or like named elements are assumed to be referencing the same or a substantially similar element having the same or substantially similar function or structure. Differences in function or structure may also be described separately without limitation, restriction, or regard to a specific feature previously described. For example, interpositional saddle surface 202 may be designed and implemented in function and structure similarly or substantially similarly to interpositional saddle surface 102 (FIGS. 1A, 1C-1G). In some examples, interpositional saddle surface 202 may be, with saddle channel openings 206 and 210, configured to be substantially concave in shape and receive a bone (e.g., metacarpal, trapezium, tibia, femur, or others, without limitation or restriction) and function similarly to the examples shown and described above in connection with FIGS. 1A-1G. Alternatively, peripheral protrusions 212-218 may be formed and integrated with periphery 220 to provide pronounced structures that, when device 202 is surgically implanted in a joint, may be configured to interact within articulating or non-articulating regions (or, in some examples, in a combination of articulating and non-articulating regions) of a joint.

In some examples, peripheral protrusions 212-218 may be implemented as spherical or substantially spherical (or other shapes) structures that are integrated (i.e., formed) with or along periphery 220 of device 202. When device 202 is surgically implanted, peripheral protrusions 212-218 may be positioned (i.e., disposed) within a joint so as to contact or provide structures that are configured to interact with bones or portions thereof adjacent or joining within a joint. Here, a channel may be formed as a concave or substantially concave surface of interpositional saddle surface 202 and saddle channel openings 206 and 210 that are configured to receive, as an example, a metacarpal bone in a CMC joint. As the CMC joint (not shown) is articulated, spherically-shaped (as shown in this example, but in others, different shapes, sizes, and quantities may be used and are not restricted or limited to the examples presented herein) peripheral protrusions 212-218 formed as part of periphery 220 are configured to prevent expulsion of device 200 from the joint. In other examples, the size, dimensions, and shape of device 200 may be configured for placement in different types of joints, including wrist, elbow, shoulder, knee, ankle, or others, without limitation or restriction. Further, peripheral protrusions may be extended to an opposing surface (i.e., an opposing interpositional saddle surface, as described in greater detail below) of interposition saddle surface 202.

As described herein, including in connection with FIGS. 1A-1G, device 200 may be surgically implanted to achieve stability and regain hand strength in a carpometacarpal ("CMC"), basal, or other type of joint and is not limited to any particular joint. When implanted, device 200 using peripheral protrusions 212-218 disposed about periphery 220 may be used to prevent expulsion of device 200 from a joint while also providing dynamic stability and pain relief in cases where cartilage has been worn away, destroyed, damaged, or is otherwise missing from a joint. Further, peripheral protrusions 212-218 are configured to not interfere with motion of joint in order to provide maximum range of extension and motion associated with individual bones forming a joint. Prevents migration of implantable device (i.e., implant or device) from joint. As described herein, device 200 may be surgically implanted (i.e., placed) in a joint at a point, position, and/or orientation where device 202 is least likely to be expulsed when the joint is articulated. As described above, device 200 is configured to permit motion or articulation of a joint without dislocation or expulsion of device 200 from the joint. In other words, when bones in a given joint are articulated, device 200 when implanted may be configured and implemented to prevent one or more bones from dislocation or expulsing device 200 from the joint.

In some examples, device 200 with peripheral protrusions 212-218 is configured to permit motion such as pivoting about one or more axes (e.g., abduction-adduction, flexion-extension, supination-pronation, and others) without dislocation of bones or displacement of device 200 from a joint. In some examples, surgical clamps or any type of implant holder may be configured for surgical insertion of implantable devices such as device 200 in human or animal joints, which may include carpometacarpal, trapeziometacarpal, or others, without limitation or restriction. In other examples, device 200 and the elements shown and described may be designed, configured, formed, modified, or implemented apart from the examples shown or described and are not limited to those provided.

Figure 2B:
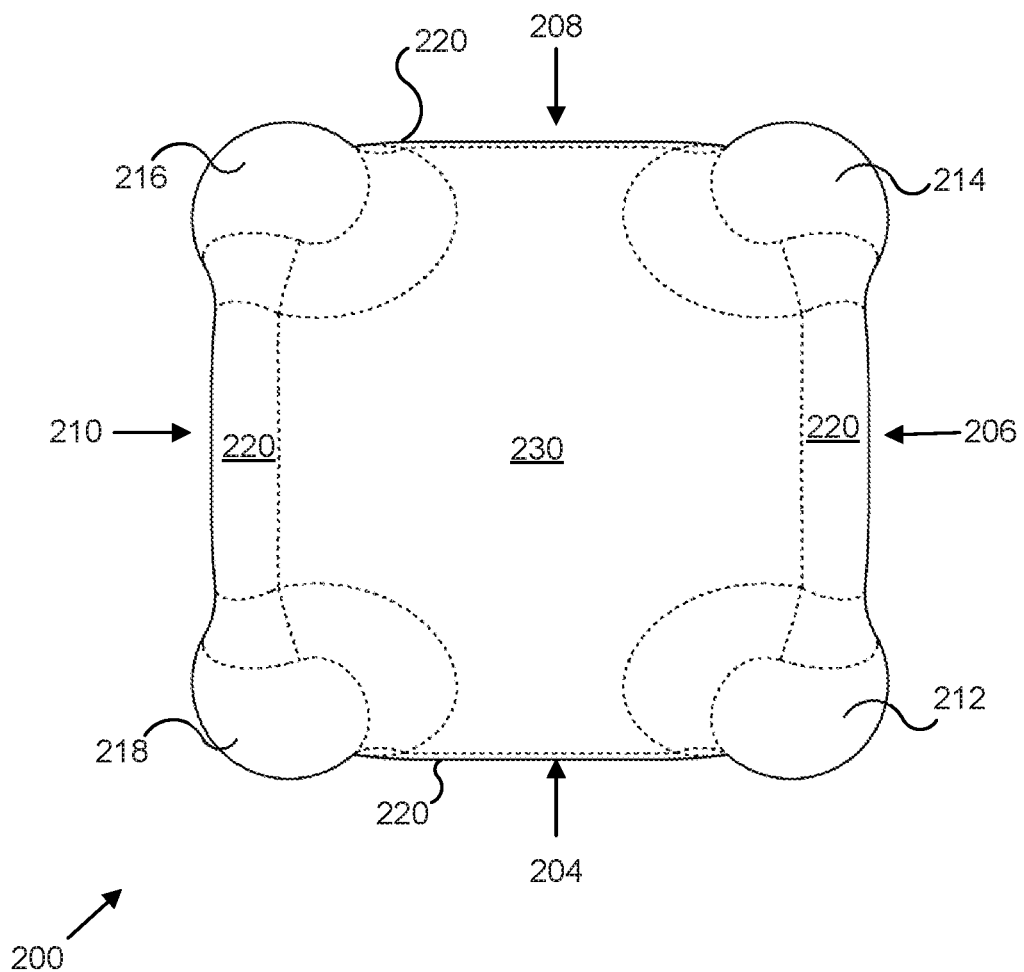
FIG. 2B illustrates a bottom view of an exemplary implantable interpositional orthopedic pain management apparatus.

FIG. 2B illustrates a bottom view of an exemplary implantable interpositional orthopedic pain management apparatus. Here, device 200 includes saddle channel openings 204-210, peripheral protrusions 212-218, periphery 220, and interpositional saddle surface 230. In some examples, interpositional saddle surface 230 may be contoured substantially opposite to that of interpositional saddle surface 202 (FIG. 2A). For example, interpositional saddle surface 202 (FIG. 2A) may be concave or substantially concave while interpositional saddle surface 230 may be formed to provide a convex or substantially convex channel for receiving an opposing bone in a joint. As an example, interpositional saddle surface 202 (FIG. 2A) may be formed as a substantially concave surface configured to receive a portion (e.g., central ridge, radial facet volar tubercle, or other structure disposed toward the proximal end of a metacarpal) of a bone while interpositional saddle surface 230 may be configured to fit a concave feature formed at the distal end of a trapezium bone. In other examples, interpositional saddle surfaces 202 (FIG. 2A) and 230 may be implemented differently and are not limited to the examples shown and described.

As used herein, like numbered and/or like named elements are assumed to be referencing the same or a substantially similar element having the same or substantially similar function or structure. Differences in function or structure may be described separately with regard to a specific feature described. In other examples, device 200 and the elements shown and described may be designed, configured, formed, modified, or implemented apart from the examples shown or described and are not limited to those provided.

Figure 2C:
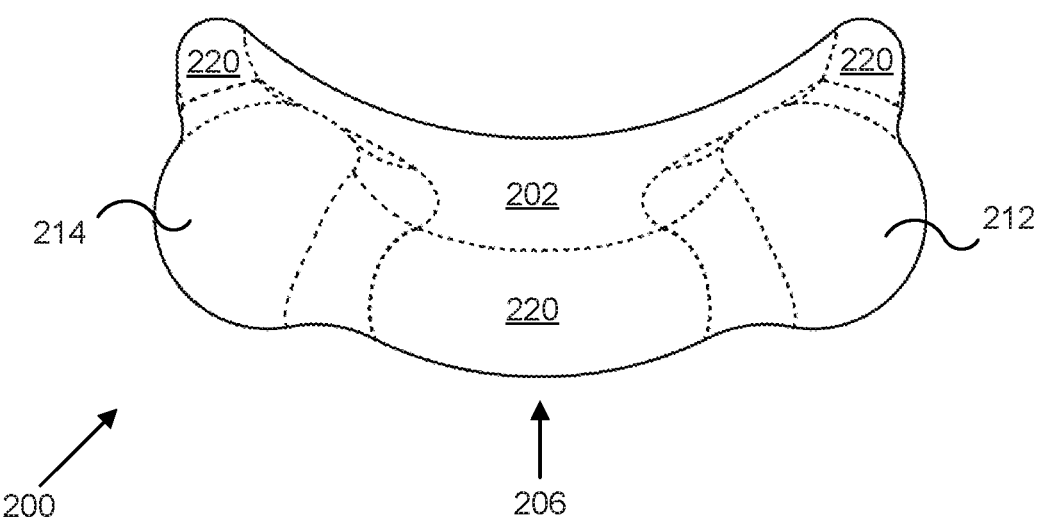
FIG. 2C illustrates an anterior view of an exemplary implantable interpositional orthopedic pain management apparatus.

FIG. 2C illustrates an anterior view of an exemplary implantable interpositional orthopedic pain management apparatus. Here, an anterior or front view of device 200 is shown, including interpositional saddle surface 202, saddle channel opening 206, peripheral protrusions 212-214, and periphery 220. As used herein, like numbered and/or like named elements are assumed to be referencing the same or a substantially similar element having the same or substantially similar function or structure. Differences in function or structure may be described separately with regard to a specific feature described. Here, a directional arrow points toward saddle channel opening 206, which is an opening into a saddle channel formed with interpositional saddle surface 202 and saddle channel opening 206 and saddle channel opening 210 (not shown) in which a bone (e.g., metacarpal, trapezium, femur, tibia, or the like) may be received. In some examples, peripheral protrusions 212-214 may be formed as substantially spherical structures that are integrated with periphery 220. In some examples, peripheral protrusions 212-214 may be configured to provide structures on one side (not shown) of device 200 or on multiple sides (as shown and described). In other examples, peripheral protrusions 212-214 may be formed differently and are not limited to the substantially spherical examples shown and described. Alternatively, peripheral protrusions 212-214 may be implemented using non-spherical or partially-spherical shapes. In other examples, device 200 and the elements shown and described may be designed, configured, formed, modified, or implemented apart from the examples shown or described and are not limited to those provided.

Figure 2D:
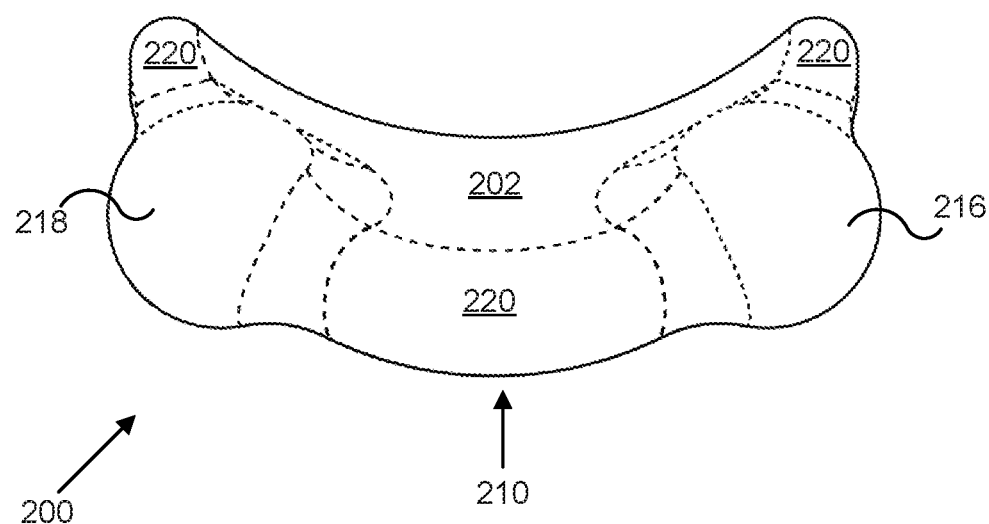
FIG. 2D illustrates a posterior view of an exemplary implantable interpositional orthopedic pain management apparatus.

FIG. 2D illustrates a posterior view of an exemplary implantable interpositional orthopedic pain management apparatus. Here, a posterior or rear view of device 200 is shown, including interpositional saddle surface 202, saddle channel opening 210, peripheral protrusions 216-218, and periphery 220. In some examples, saddle channel opening 210 is configured to form, with interpositional saddle surface 202 and saddle channel opening 206 (FIG. 2C) a saddle-shaped channel configured to receive a bone in interpositional saddle surface 202 when device 200 is surgically implanted into a synovial capsule and joint. Disposed at an opposite end of a saddle channel formed with interpositional saddle surface 202 and saddle channel opening 206, saddle channel opening 210 is configured to receive a bone or a portion thereof (e.g., metacarpal) onto interpositional saddle surface 202. As used herein, like numbered and/or like named elements are assumed to be referencing the same or a substantially similar element having the same or substantially similar function or structure. Differences in function or structure may be described separately with regard to a specific feature described. In other examples, device 200 and the elements shown and described may be designed, configured, formed, modified, or implemented apart from the examples shown or described and are not limited to those provided.

Figure 2E:
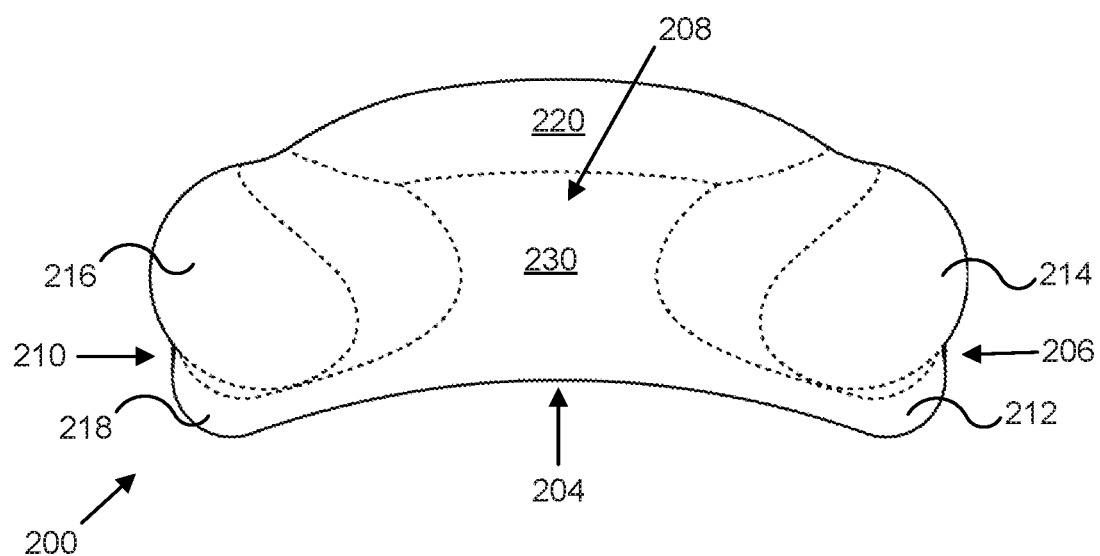
FIG. 2E illustrates a left view of an exemplary implantable interpositional orthopedic pain management apparatus.

FIG. 2E illustrates a left view of an exemplary implantable interpositional orthopedic pain management apparatus. Here, device 200 is shown from a left view, including saddle channel openings 204-210, peripheral protrusions 212-218, periphery 220, and interpositional saddle surface 230. From a side view, interpositional saddle surface 230 is visible substantially underneath device 200 with saddle channel openings 204 and 208 at either end. In some examples, interpositional saddle surface 230 is configured, with saddle channel openings 204 and 208, to receive a bone or a portion thereof when device 200 is surgically implanted. For example, if device 200 is surgically implanted into a CMC joint, interpositional saddle surface 230 may be configured, with saddle channel openings 204 and 208, to receive (i.e., interpositional saddle surface 230 may have a radius of curvature that is larger than that of a trapezium bone) a trapezium bone, or other bone adjacent to the joint. As described above, a saddle channel consisting of interpositional saddle surface 202 (not shown; FIG. 2A) is also disposed between saddle channel openings 206 and 210. As used herein, like numbered and/or like named elements are assumed to be referencing the same or a substantially similar element having the same or substantially similar function or structure. Differences in function or structure may be described separately with regard to a specific feature described. In other examples, device 200 and the elements shown and described may be designed, configured, formed, modified, or implemented apart from the examples shown or described and are not limited to those provided.

Figure 2F:
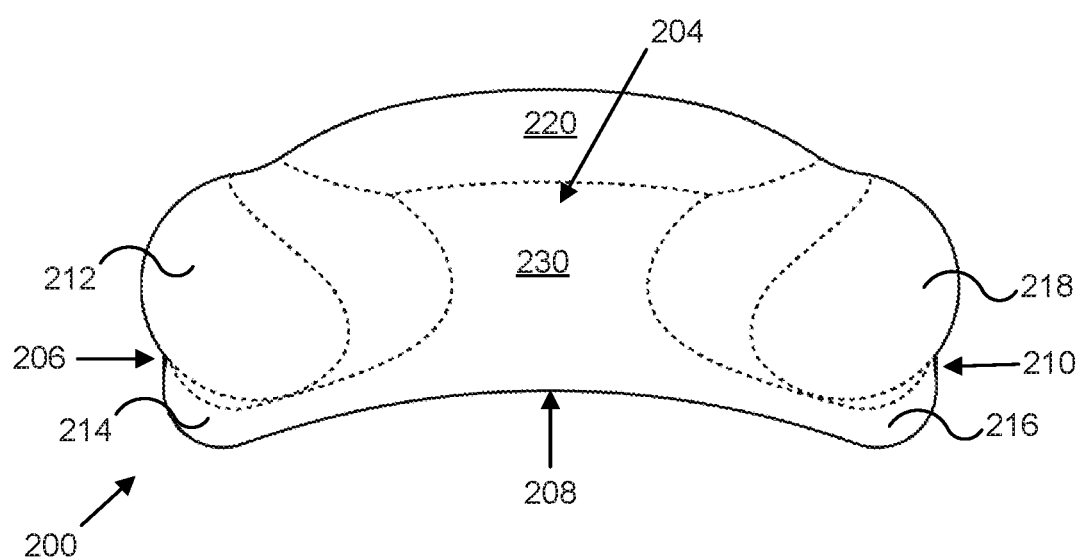
FIG. 2F illustrates a right view of an exemplary implantable interpositional orthopedic pain management apparatus.

FIG. 2F illustrates a right view of an exemplary implantable interpositional orthopedic pain management apparatus. Here, a right view of device 200 is shown including saddle channel openings 204-210, peripheral protrusions 212-218, periphery 220, and interpositional saddle surface 230. As used herein, like numbered and/or like named elements are assumed to be referencing the same or a substantially similar element having the same or substantially similar function or structure. Differences in function or structure may be described separately with regard to a specific feature described. In other examples, device 200 and the elements shown and described may be designed, configured, formed, modified, or implemented apart from the examples shown or described and are not limited to those provided.

Figure 2G:
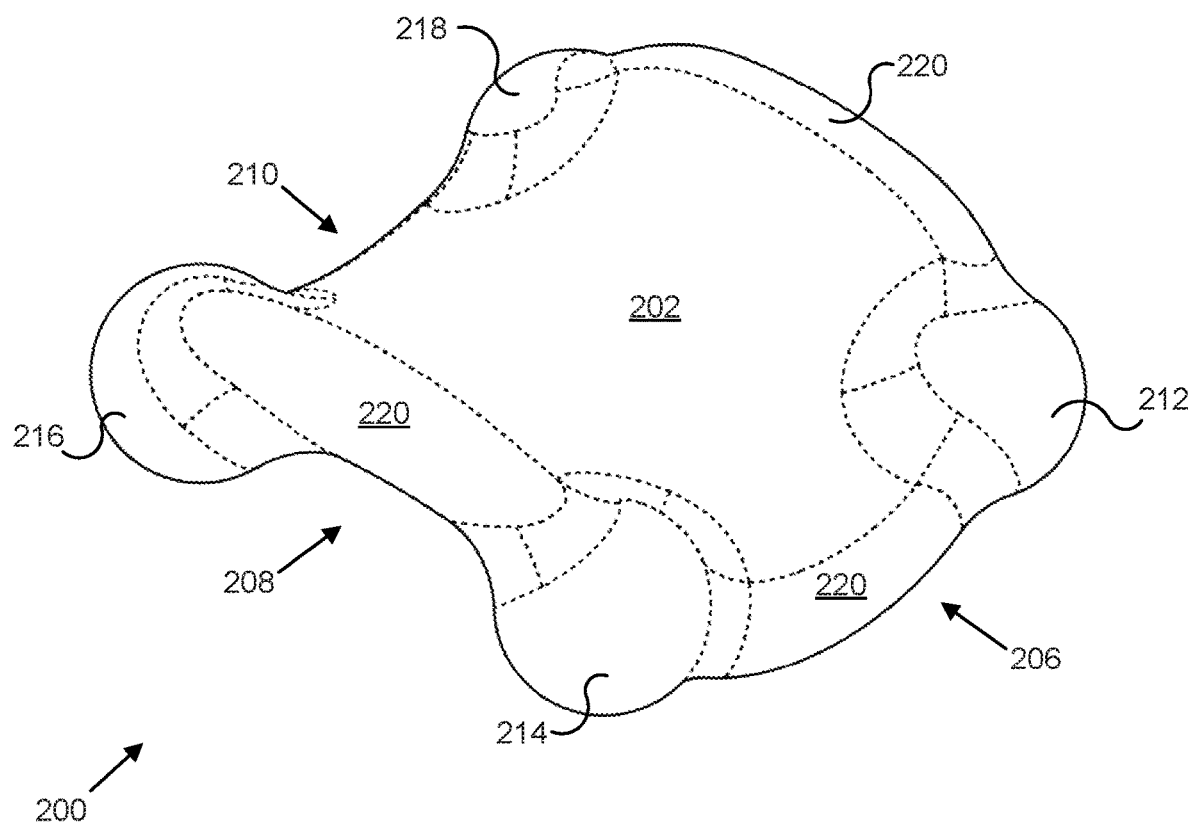
FIG. 2G illustrates a perspective view of an exemplary implantable interpositional orthopedic pain management apparatus.

FIG. 2G illustrates a perspective view of an exemplary implantable interpositional orthopedic pain management apparatus. Here, device 200 includes interpositional saddle surface 202, saddle channel openings 206-210, peripheral protrusions 212-218, and periphery 220. In some examples, a channel configured to receive a bone (e.g., a metacarpal bone in a CMC joint or a bone adjacent to another joint) may be implemented using interpositional saddle surface 202, saddle channel openings 206 and 210. As described above, when device 200 is surgically implanted in a joint (e.g., through an incision or opening in a synovial capsule), peripheral protrusions 212-218 may be oriented by positioning device 200 in a joint to provide dynamic stability to a joint with weakened, degraded, or missing cartilage while preventing dislocation of bones from a joint and expulsion of device 200 when a given joint is articulated. As shown, another saddle channel may be implemented on the opposite side of device 200 by using interpositional saddle surface 230 (FIG. 2B; not shown) and saddle channel openings 204 (FIG. 2B; not shown) and 208. As used herein, like numbered and/or like named elements are assumed to be referencing the same or a substantially similar element having the same or substantially similar function or structure. Differences in function or structure may be described separately with regard to a specific feature described. In other examples, device 200 and the elements shown and described may be designed, configured, formed, modified, or implemented apart from the examples shown or described and are not limited to those provided.

Figure 3A:
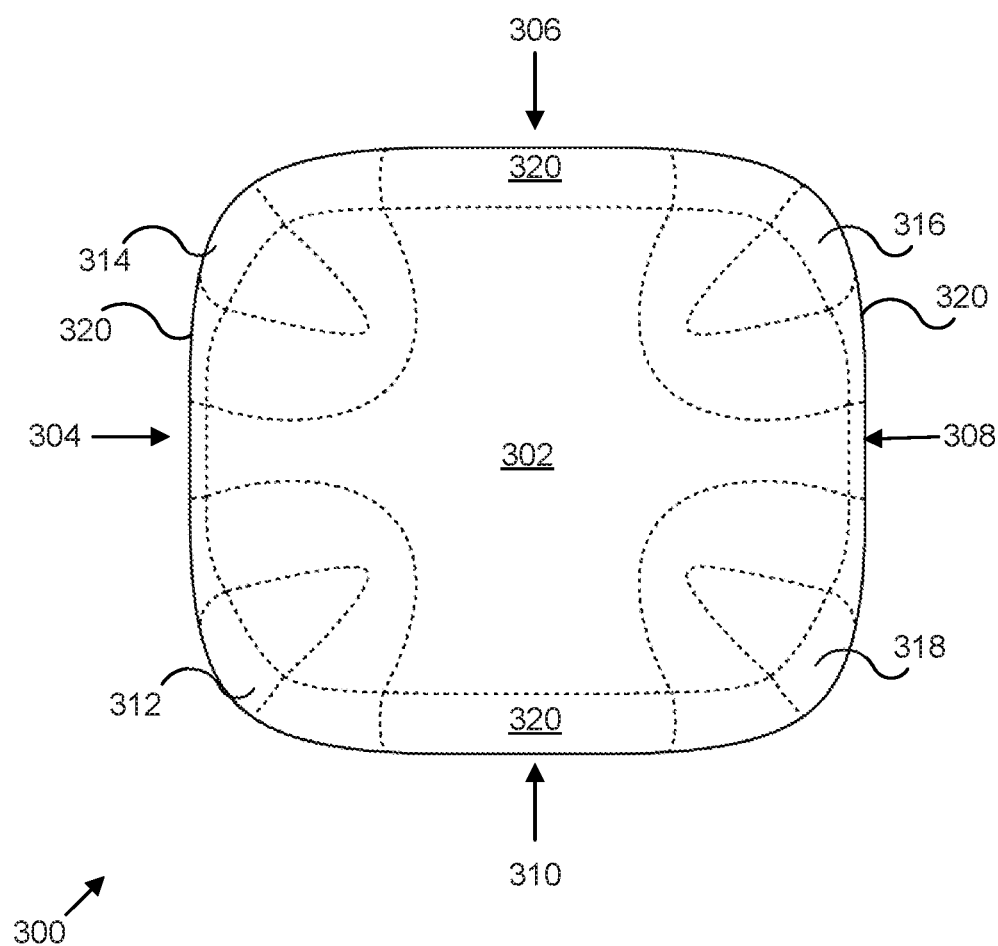
FIG. 3A illustrates a top view of an exemplary implantable interpositional orthopedic pain management apparatus.

FIG. 3A illustrates a top view of an exemplary implantable interpositional orthopedic pain management apparatus. Here, device 300 includes interpositional saddle surface 302, saddle channel openings 304-310, peripheral protrusions 312-318, and periphery 320. As used herein, like numbered and/or like named elements are assumed to be referencing the same or a substantially similar element having the same or substantially similar function or structure. Differences in function or structure may be described separately with regard to a specific feature described. As shown in this drawing and others above and below, dotted lines are presented for purposes of illustrating contours and features that may include convex or concave ridges, structural or ornamental features, or other attributes as described herein.

In some examples, interpositional saddle surface 302 is configured to provide a concave surface of device 300 that is contoured and integrated with peripheral protrusions 312-318, which may be configured to "rise" from the channel formed between saddle channel openings 304 and 308. As used throughout the description of this drawing and others described above and below, the term "channel" may refer to a concave or convex feature using interpositional saddle surfaces such as interpositional saddle surface 302 or 330 (see FIG. 3B below), which functions to provide a structural feature that is configured to fit within a joint as described herein.

Here, dotted lines are presented to illustrate contouring of peripheral protrusions 312-318 as corner features of periphery 320, the latter of which may describe a perimeter portion of device 300. While formed as part or integrated with device 300, periphery 300 may be an outermost perimeter of device 300 into which features are shaped such as peripheral protrusions 312-318. As shown, periphery 320 can be found on the outer edges (i.e., perimeter) of device 300 and, disposed at various points are peripheral protrusions 312-318. In other examples, as in the previously and following described figures, the number, shape, type, quantity, and disposition of peripheral protrusions 312-318 may be varied and are not limited to those shown and described.

Here, peripheral protrusions 312-318 are illustrated in contrast to spherical or substantially spherical (e.g., peripheral protrusions 212-218 (FIGS. 2A-2G)), flat or substantially flat (e.g., 112-118 (FIGS. 1A-1G)) shapes such as those previously shown and described. In some examples, peripheral protrusions 212-218 are shaped to provide additional features and contours to improve placement, positioning, and expulsion resistance when device 300 is surgically implanted. Cavities formed within the proximal or distal ends of bones may have structures that device 300 is configured to contour to fit. The dotted lines shown in device 300 may represent contours of peripheral protrusions 212-218 that are configured to be disposed within non-articulating portions of a synovial capsule and/or joint and, when motion occurs that articulates a given joint, device 300 alleviates pain by preventing distal and proximal ends of bones in a joint from contact while peripheral protrusions also prevent dislocation (i.e., one or more bones distracting or dislocating from a joint) and expulsion of device 300. In other examples, device 300 and the elements shown and described may be designed, configured, formed, modified, or implemented apart from the examples shown or described and are not limited to those provided.

Figure 3B:
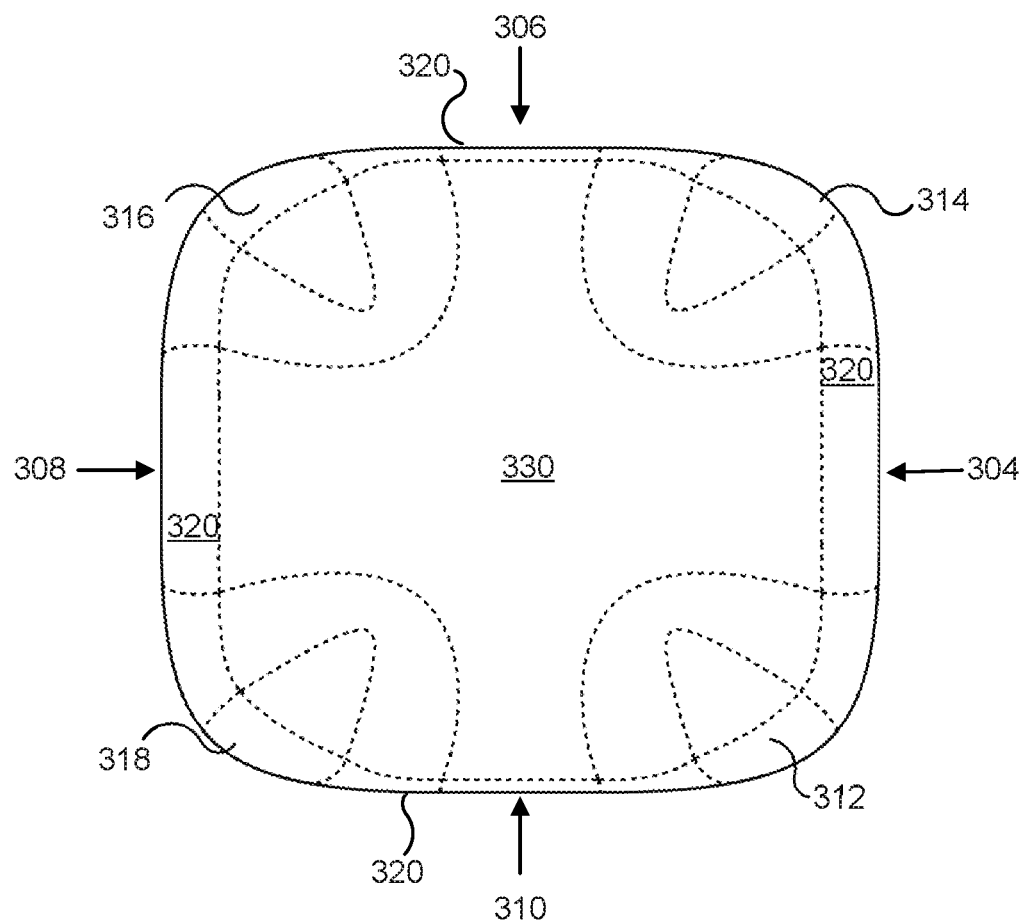
FIG. 3B illustrates a bottom view of an exemplary implantable interpositional orthopedic pain management apparatus.

FIG. 3B illustrates a bottom view of an exemplary implantable interpositional orthopedic pain management apparatus. Here, device 300 includes saddle channel openings 304-310, peripheral protrusions 312-318, periphery 320, and interpositional saddle surface 330. As used herein, like numbered and/or like named elements are assumed to be referencing the same or a substantially similar element having the same or substantially similar function or structure. Differences in function or structure may be described separately with regard to a specific feature described. As shown herein, an "underside" view of device 300 is shown with interpositional saddle surface 330 forming a channel or contour that is configured to be disposed over or fit within a cavity formed with or within a bone, bone structure, bone joint, or portion(s) thereof, functioning similar or substantially similar to the other examples shown and described above and below in connection with various drawings throughout. In some examples, interpositional saddle surface 330 may be convex, concave, or having a radius of curvature that is substantially opposing to that of interpositional saddle surface 302. For example, interpositional saddle surface 302 (FIG. 3A) may be concave or substantially concave while interpositional saddle surface 330 may be convex or substantially convex.

Here, the radius of curvature of each of interpositional saddle surfaces 302 and 330 are configured such that a layer of material such as those described above is disposed between interpositional saddle surfaces 302 and 330 in such a manner that a cross sectional area that is coplanar between the two is substantially rectangular in shape or configuration. While the various examples shown herein may exhibit symmetry around various axes, in other examples device 300 and others described above and below may be asymmetrically formed or off-axially aligned, including when surgically implanted within a joint. In still other examples, device 300 and the elements shown and described may be designed, configured, formed, modified, or implemented apart from the examples shown or described and are not limited to those provided.

Figure 3C:
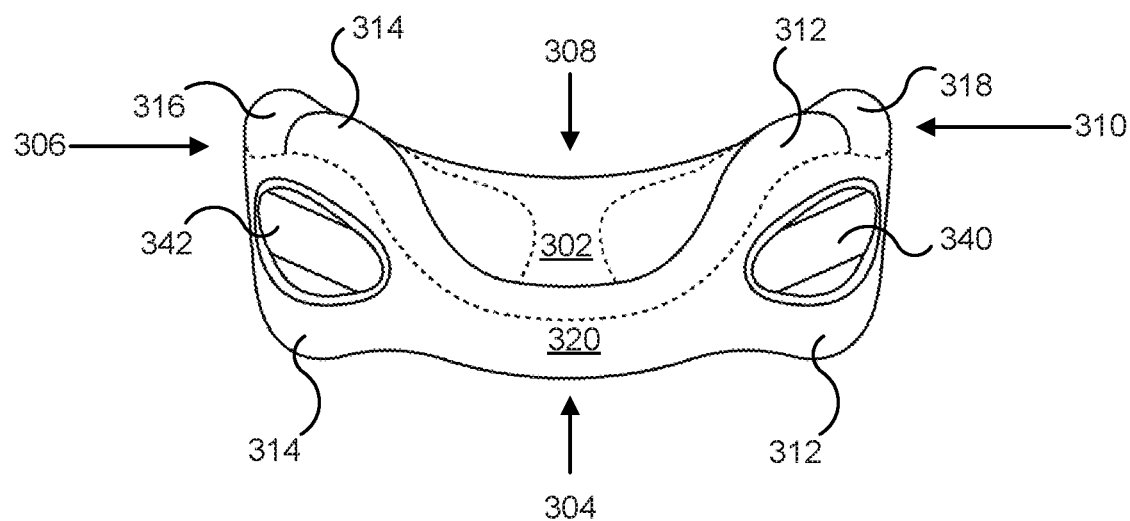
FIG. 3C illustrates an anterior view of an exemplary implantable interpositional orthopedic pain management apparatus.

FIG. 3C illustrates an anterior view of an exemplary implantable interpositional orthopedic pain management apparatus. Here, an anterior or frontal view of device 300 includes interpositional saddle surface 302, saddle channel openings 304-310, peripheral protrusions 312-318 disposed in periphery 320, and contours 340-342. As used herein, like numbered and/or like named elements are assumed to be referencing the same or a substantially similar element having the same or substantially similar function or structure. Differences in function or structure may be described separately with regard to a specific feature described. In some examples, an interpositional saddle (i.e., "channel") is provided by interpositional surface 302 and saddle channel openings 304 and 308, which is configured to receive a bone (e.g., metacarpal) when surgically implanted into a joint (e.g., CMC joint). Disposition within a joint (not shown) may include peripheral protrusions 312-318 being positioned to prevent expulsion of device 300 when the joint is articulated. Specifically, one or more of peripheral protrusions 312-318 (which are shown extending both to the upper and lower surfaces of device 300) may be configured to interact with one or more bones, bone structures, heads, ends, or portions thereof when surgically implanted. Further, contours 340-342 may be configured to provide additional surface features or contours that are also shaped or formed to interact with other portions of one or more bones, bone structures, heads, ends, or portions thereof when device 300 is surgically implanted within a joint. In other words, when surgically implanted, peripheral protrusions 312-318 and contours 340-342 may be configured for different types of joints or those that are specific to a given individual based on input or attributes determined or defined from techniques such as x-rays, magnetic resonance imaging (MRI), computed tomography (CAT), fluoroscopy, or other types of imaging techniques, without limitation or restriction. Device 300, as shown and described herein, provides peripheral or corner features that may be tailored to provide customization features for individual joints, bones, or other anatomical structures. Additionally, another channel may be provided, as partially indicated by saddle channel openings 306 and 310, which may be used with interpositional saddle channel 330 (FIG. 3B) to provide an opposing or substantially opposing channel on the underside of device 300 that is shaped to receive mutually reciprocal or substantially mutually reciprocal bones, bone structures, or portions thereof in a joint (e.g., trapezium, metacarpal, radial facet of a metacarpal, or others, without restriction or limitation). In other examples, device 300 and the elements shown and described may be designed, configured, formed, modified, or implemented apart from the examples shown or described and are not limited to those provided.

Figure 3D:
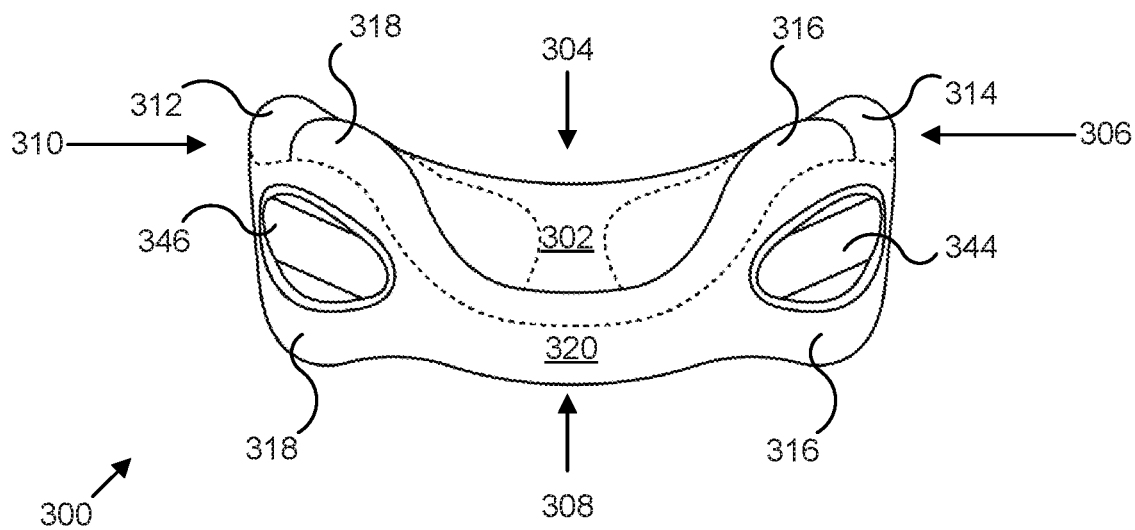
FIG. 3D illustrates a posterior view of an exemplary implantable interpositional orthopedic pain management apparatus.

FIG. 3D illustrates a posterior view of an exemplary implantable interpositional orthopedic pain management apparatus. Here, a posterior or rear view of device 300 includes interpositional saddle surface 302, saddle channel openings 304-310, peripheral protrusions 312-318 disposed in periphery 320, and contours 344-346. As used herein, like numbered and/or like named elements are assumed to be referencing the same or a substantially similar element having the same or substantially similar function or structure. Differences in function or structure may be described separately with regard to a specific feature described.

Here, peripheral protrusions 312-318 are shown, including contours 344-346, which are configured in structure and function similarly to contours 340-342 (FIG. 3C). Peripheral protrusions 312-318 and contours 344-346 may be configured to reside in non-articulating regions of a joint (not shown) when device 300 is surgically implanted. In some examples, like contours 340-342 (FIG. 3C), contours 344-346 may be formed with various types of shapes and features (e.g., convex, concave, partially or wholly, or a combination thereof). If one or more bones of the joint (in which device 300 is surgically implanted) are articulated, then peripheral protrusions 312-318 and contours 344-346 are configured to prevent the bones from coming into contact with each other, maintaining dynamic stability, and restoring an ability for the joint to be manipulated while preventing expulsion of device 300 from the joint or dislocation of bones from the joint. In other words, peripheral protrusions 312-318 and contours 344-346 may be formed to provide structures that function to interact with anatomical structures of a joint, including the bones or portions thereof within the joint, to prevent device 300 from expulsion and dislocation. In other examples, device 300 and the elements shown and described may be designed, configured, formed, modified, or implemented apart from the examples shown or described and are not limited to those provided.

Figure 3E:
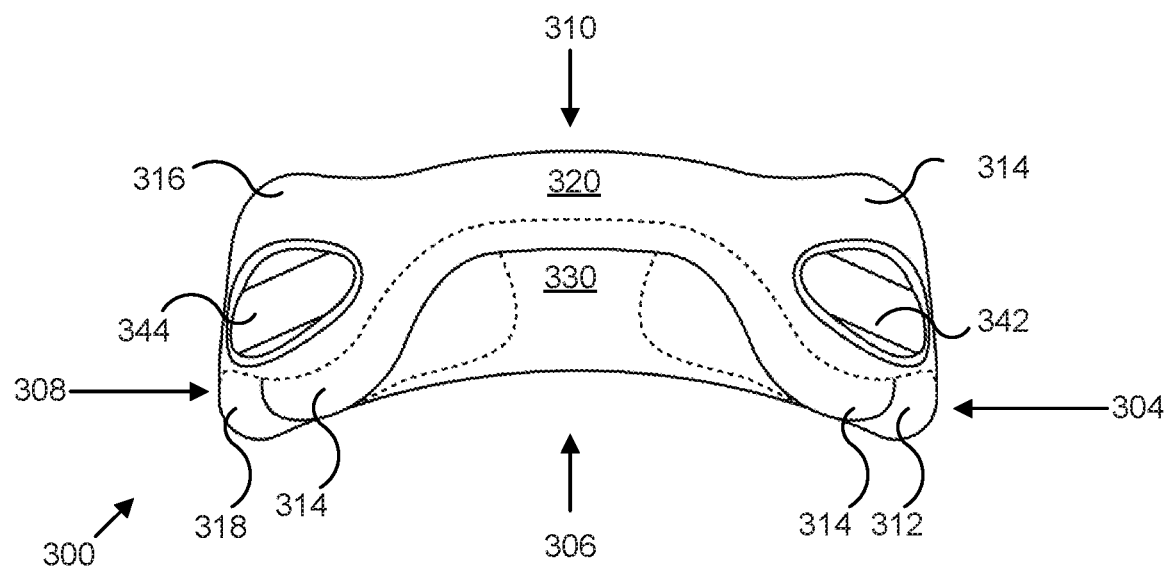
FIG. 3E illustrates a left view of an exemplary implantable interpositional orthopedic pain management apparatus.

FIG. 3E illustrates a left view of an exemplary implantable interpositional orthopedic pain management apparatus. Here, a left side view of device 300 includes saddle channel openings 304-310, peripheral protrusions 312-318 disposed along and within periphery 320, interpositional saddle surface 330, and contours 342-344. As used herein, like numbered and/or like named elements are assumed to be referencing the same or a substantially similar element having the same or substantially similar function or structure. Differences in function or structure may be described separately with regard to a specific feature described. As shown, a left side view reveals interpositional saddle surface 330 on the underside of device 300 forming a channel between saddle channel openings 306 and 310 in a substantially orthogonal or substantially mutually reciprocal orientation to the channel described above in connection with FIG. 3C. In other examples, the channel formed by interpositional saddle surface 330 and saddle channel openings 306 and 310 may be oriented differently (i.e., set at an angle other than orthorgonal to a given axis) and implementation of the techniques described herein do not require an axially orthogonal position. Alternatively, a channel may be found on only a single side of device 300 and is not required to be on mutually reciprocal or substantially reciprocal sides of device 300.

In other examples, device 300 and the elements shown and described may be designed, configured, formed, modified, or implemented apart from the examples shown or described and are not limited to those provided.

Figure 3F:
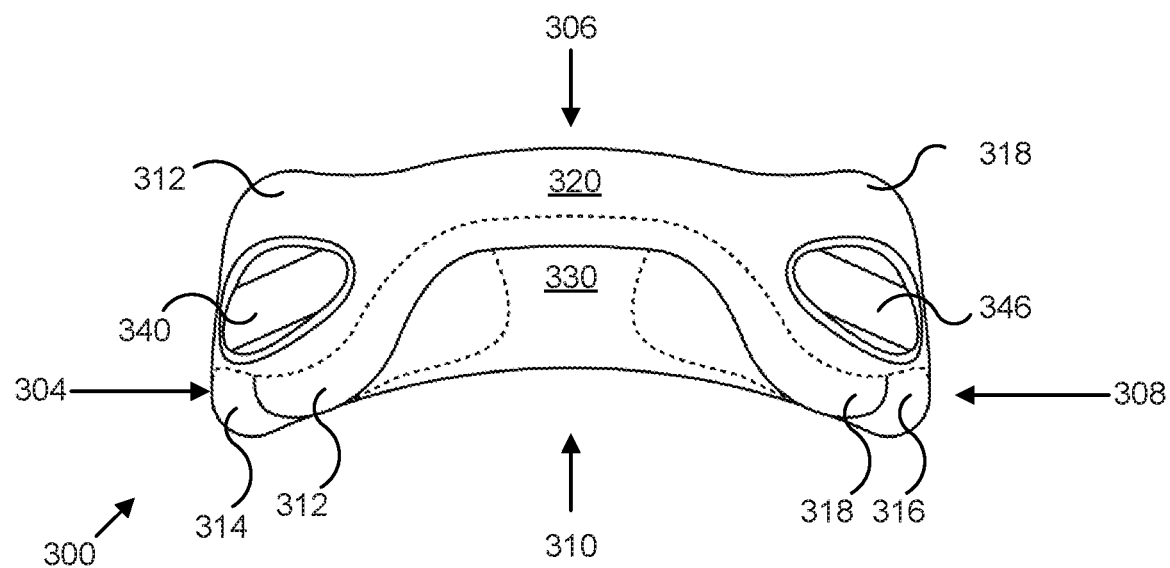
FIG. 3F illustrates a right view of an exemplary implantable interpositional orthopedic pain management apparatus.

FIG. 3F illustrates a right view of an exemplary implantable interpositional orthopedic pain management apparatus. Here, a right side view of device 300 includes saddle channel openings 304-310, peripheral protrusions 312-318 disposed along and integrated with periphery 320, interpositional saddle surface 330, and contours 344 and 346. As used herein, like numbered and/or like named elements are assumed to be referencing the same or a substantially similar element having the same or substantially similar function or structure. Differences in function or structure may be described separately with regard to a specific feature described.

In some examples, peripheral protrusions 312-318 may be coupled directly or indirectly with periphery 320 or formed as surface or structural features or components thereof. As shown and described, peripheral protrusions 312-318 may have various sizes, shapes, dimensions, and other attributes, without limitation or restriction. As shown and described, peripheral protrusions 312-318 may have features integrated or formed within them as well, including, but not limited to, contours 340 and 346. Like contours 342-344 (FIG. 3E), contours 344 and 346 may be implemented as concave features, "dimple-like" in appearance, but are configured to provide contouring for peripheral protrusions 312-318 to engage and fit within a joint when device 300 is surgically implanted.

As shown, an "opening" into a saddle-shaped channel formed by interpositional saddle surface 330 and extending between saddle channel openings 310 (from the right side of device 300) and 306 (not shown, but disposed as a saddle-shaped opening from the left side of device (FIG. 3E)). In some examples, interpositional saddle surface 330 may be a mutually reciprocal surface to interpositional saddle surface 302, both of which provides engaging surfaces of device 300 to fit within a joint having, for example, opposing bones, bone structures, or portions thereof In other examples, peripheral protrusions 312-318 may be implemented with multiple or no contours (e.g., contours 340-346), or varied beyond those examples shown and/or described, without limitation or restriction. In still other examples, device 300 and the elements shown and described may be designed, configured, formed, modified, or implemented apart from the examples shown or described and are not limited to those provided.

Figure 3G:
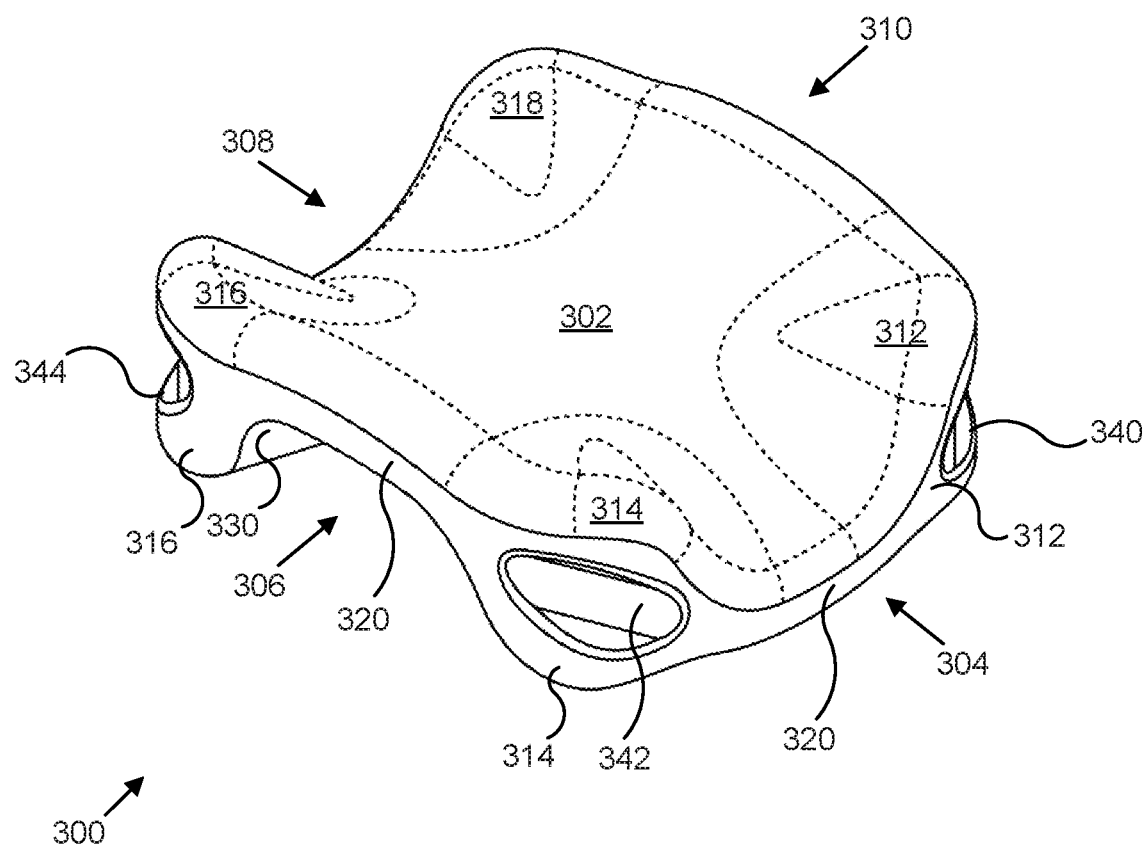
FIG. 3G illustrates a perspective view of an exemplary implantable interpositional orthopedic pain management apparatus.

FIG. 3G illustrates a perspective view of an exemplary implantable interpositional orthopedic pain management apparatus. Here, a perspective view of device 300 includes interpositional saddle surface 302, saddle channel openings 304-310, peripheral protrusions 312-318 in periphery 320, interpositional saddle surface 330, and contours 340-344 (contour 346 (FIG. 3F) formed as part of peripheral protrusion 318 is not shown). As used herein, like numbered and/or like named elements are assumed to be referencing the same or a substantially similar element having the same or substantially similar function or structure. Differences in function or structure may be described separately with regard to a specific feature described.

As shown, in some examples, device 300 has multiple channel configured to receive the proximal or distal ends of bones within a joint (not shown). Interpositional saddle surfaces 302 and 330 are shown, which are formed and integrated with peripheral protrusions 312-318 from a top and bottom surfaces of device 300. Here, dotted lines are provided to show outlines of peripheral protrusions 312-318, which provide corner structures that "rise" from the corners of interpositional saddle surface 302 to provide structures that, when placed within non-articulating regions of a joint, prevent device 300 from being expulsed, partially or wholly, when the joint is articulated. Further, peripheral protrusions 312-318 may be implemented with additional structures configured to further prevent expulsion of device 300 from a joint or to aid in maintaining position and/or orientation of device 300 when surgically implanted. For example, contours 340-344 may be implemented as substantially concave features that can be configured to "fit" or receive bones, bone structures, or portions thereof in addition to interpositional saddle surfaces 302 and 330 when device 300 is surgically implanted. In other examples, contours 340-344 may also be configured to provide surfaces that are shaped to fit and/or fill with other materials within a synovial capsule such as cartilage, blood, bodily fluids, or other synthetic or organic materials that are injected or otherwise implanted to aid device 300 in maintaining dynamic stability and position within a joint after surgical implantation. In still other examples, device 300 and the elements shown and described may be designed, configured, formed, modified, or implemented apart from the examples shown or described and are not limited to those provided.

Figure 4A:
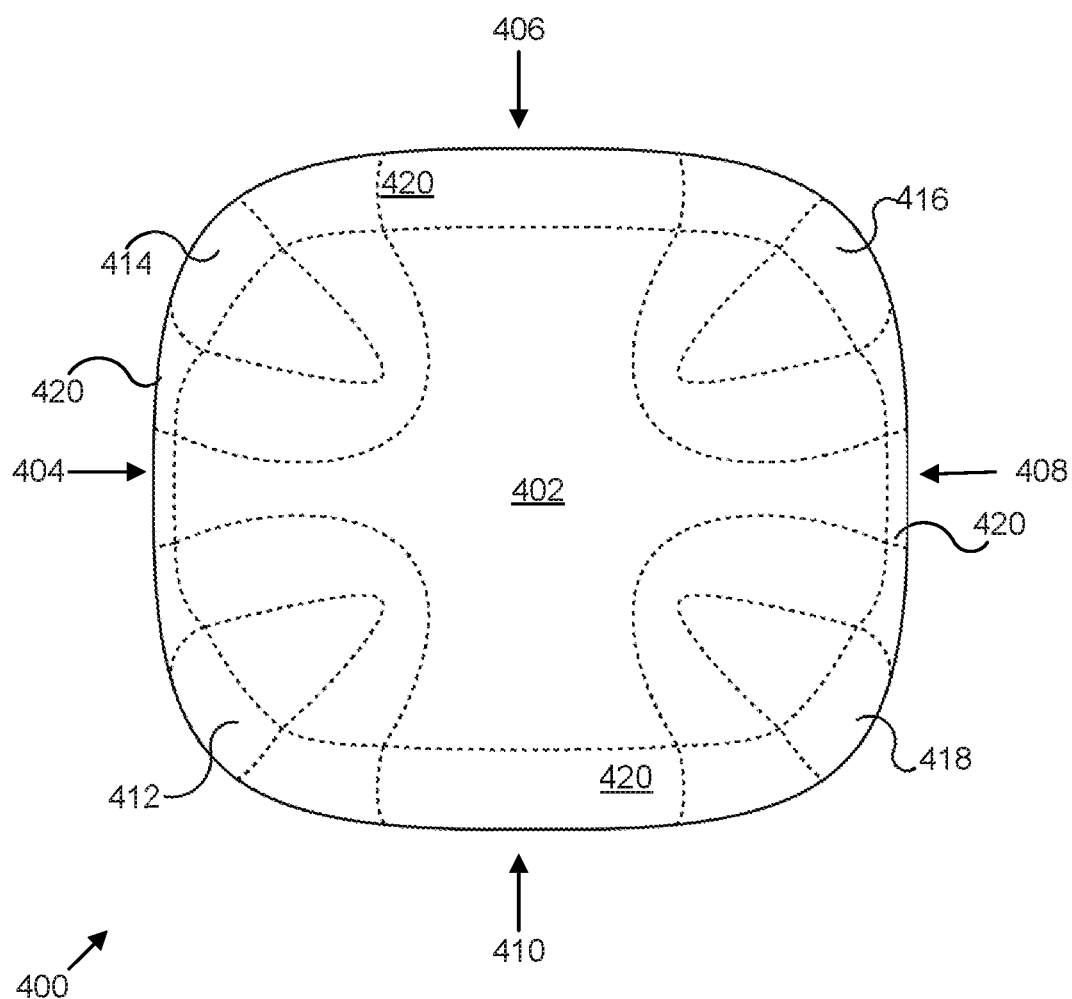
FIG. 4A illustrates a top view of an exemplary implantable interpositional orthopedic pain management apparatus.

FIG. 4A illustrates a top view of an exemplary implantable interpositional orthopedic pain management apparatus. Here, device 400 includes interpositional saddle surface 402, saddle channel openings 404-410, and peripheral protrusions 412-418 disposed along periphery 420. As used herein, like numbered and/or like named elements are assumed to be referencing the same or a substantially similar element having the same or substantially similar function or structure. Differences in function or structure may be described separately with regard to a specific feature described. In some examples, device 400 may be designed, formed, and implemented as described above. Broken (i.e., dotted) lines are provided for purposes illustrating contours of peripheral protrusions 412-418, which are formed as part of periphery 420 and interpositional saddle surface 402. In some examples, peripheral protrusions 412-418 may be built up as structures that rise in the "corners" of device 400 from a concave recess or cavity (or convex feature) formed from interpositional saddle surface 402 that is configured to maintain dynamic stability of device 400 once surgically implanted in a joint. Peripheral protrusions 412-418 may also be configured in some examples without contours or other features, such as those described above in connection with FIGS. 3A-3G. In other examples, device 400 and the elements shown and described may be designed, configured, formed, modified, or implemented apart from the examples shown or described and are not limited to those provided.

Figure 4B:
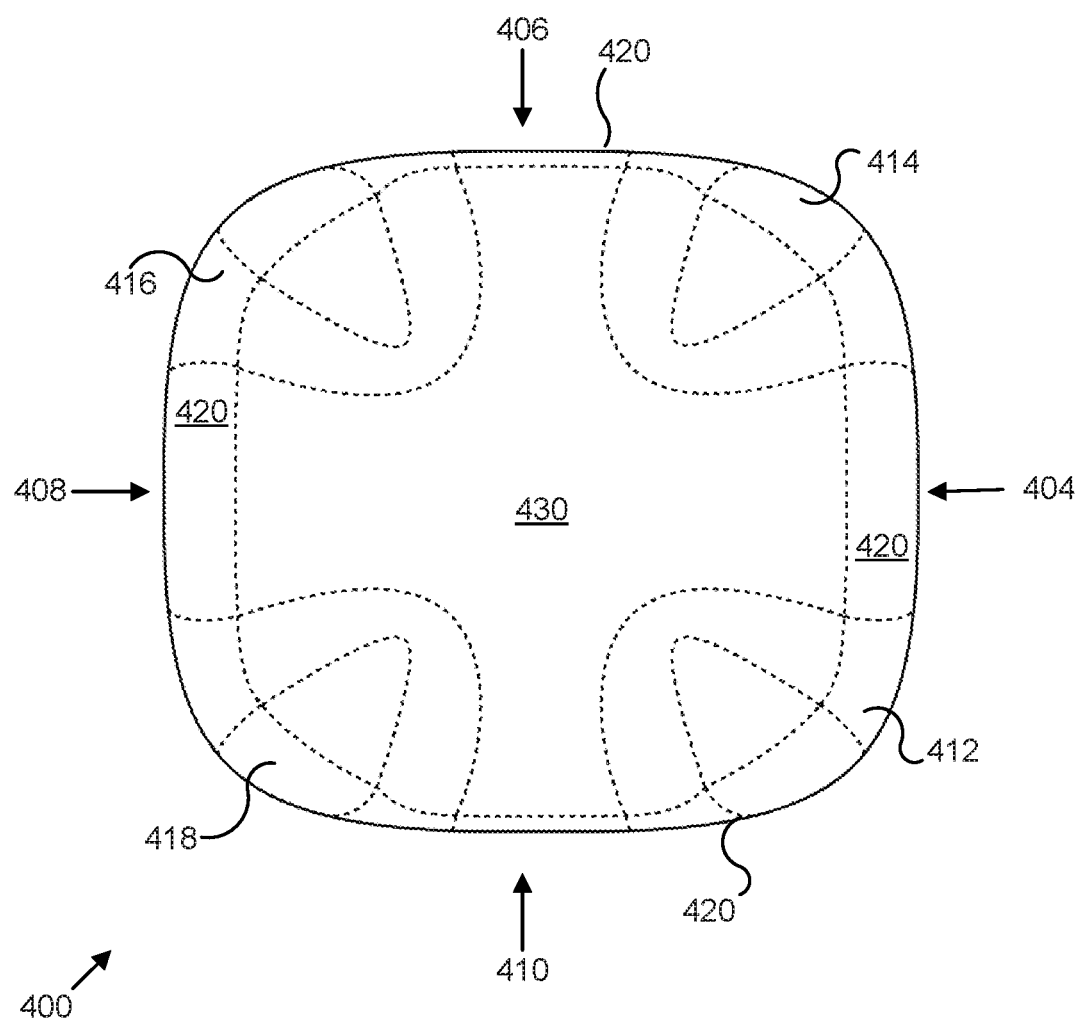
FIG. 4B illustrates a bottom view of an exemplary implantable interpositional orthopedic pain management apparatus.

FIG. 4B illustrates a bottom view of an exemplary implantable interpositional orthopedic pain management apparatus. Here, a bottom view of device 400 is shown, including saddle channel openings 404-410, peripheral protrusions 412-418 disposed in periphery 420, and interpositional saddle surface 430. As used herein, like numbered and/or like named elements are assumed to be referencing the same or a substantially similar element having the same or substantially similar function or structure. Differences in function or structure may be described separately with regard to a specific feature described. For example, peripheral protrusions 412-418 may be designed, formed, implemented, and function substantially similar or similar to peripheral protrusions 312-318 (FIG. 3A) or as other examples shown or described.

Here, broken (i.e., dotted) lines are shown for purposes of illustrating the outline of peripheral protrusions 412-418 as shown integrated with device 400 and interpositional saddle surface 430. In other examples, device 400 and the elements shown and described may be designed, configured, formed, modified, or implemented apart from the examples shown or described and are not limited to those provided.

Figure 4C:
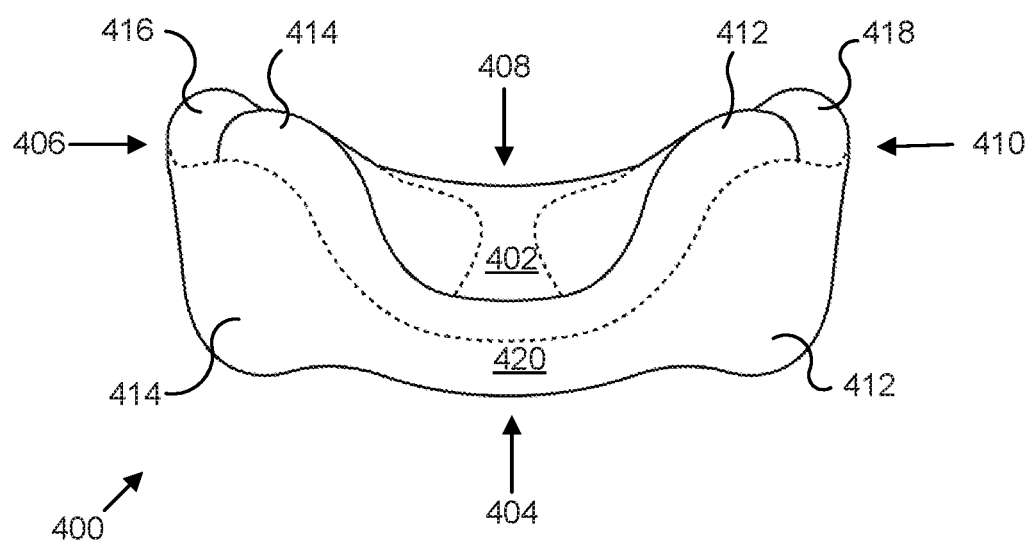
FIG. 4C illustrates an anterior view of an exemplary implantable interpositional orthopedic pain management apparatus.

FIG. 4C illustrates an anterior view of an exemplary implantable interpositional orthopedic pain management apparatus. Here, an anterior or front view of device 400 includes interpositional saddle surface 402, saddle channel openings 404-410, peripheral protrusions 412-418 disposed along periphery 420. As used herein, like numbered and/or like named elements are assumed to be referencing the same or a substantially similar element having the same or substantially similar function or structure. Differences in function or structure may be described separately with regard to a specific feature described. In some examples, peripheral protrusions 412-418 may be implemented without contours (e.g., contours 340-346 (FIGS. 3A-3G)) and instead provide substantially vertical walls rising from the bottom to the top of device 300 (i.e., from the bottom to the top of peripheral protrusions 412-418). Device 400, as shown and described here, is an example of another type of implementation that may be used to provide dynamic stability and range of motion while providing pain relief and prevent expulsion due to joint articulation (i.e., one or more bones, bone structures, or portions thereof being manipulated within a joint) after surgical implantation. As shown and described, interpositional saddle surface 402 forms a channel between saddle channel openings 404 and 408 while saddle channel openings 406 and 410 provide another channel with interpositional saddle surface 430 (FIG. 4B). Directional arrows associated with saddle channel openings 404-410 are intended to indicate openings for each of channel formed using interpositional saddle surfaces 402 and 430. For example, saddle channel opening 404 indicates an opening between peripheral protrusions 412 and 414 that is directed into a substantially concave recess formed by interpositional saddle surface 402, which then exits through saddle channel opening 408. Likewise, another channel is indicated at either end by saddle channel openings 406 and 410 that, together with interpositional saddle channel 430, create another channel on the bottom surface of device 400. In other examples, device 400 and the elements shown and described may be designed, configured, formed, modified, or implemented apart from the examples shown or described and are not limited to those provided.

Figure 4D:
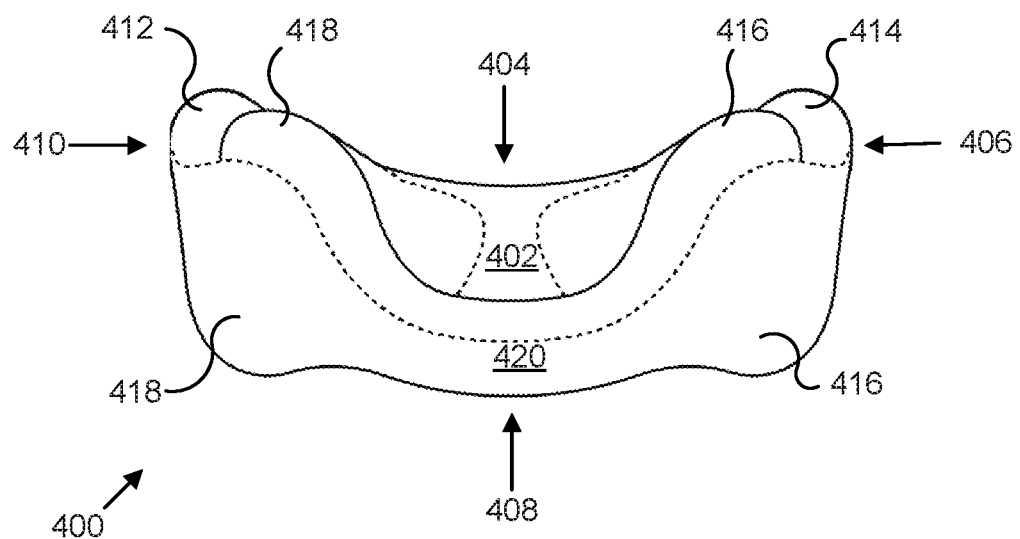
FIG. 4D illustrates a posterior view of an exemplary implantable interpositional orthopedic pain management apparatus.

FIG. 4D illustrates a posterior view of an exemplary implantable interpositional orthopedic pain management apparatus. Here, posterior or rear view of device 400 includes interpositional saddle surface 402, saddle channel openings 404-410, peripheral protrusions 412-418 disposed along periphery 420. As used herein, like numbered and/or like named elements are assumed to be referencing the same or a substantially similar element having the same or substantially similar function or structure. Differences in function or structure may be described separately with regard to a specific feature described. In some examples, a rear view of device 400 further illustrates peripheral protrusions 416-418 may be implemented with or without contours (e.g., contours 340-346 (FIGS. 3A-3G)), such as those shown and described above. Peripheral protrusions 412-418 may be varied and are not limited to examples shown and described and may be varied in number, placement, position, shape, configuration, shape, and may be varied in other attributes, without limitation or restriction. In other examples, device 400 and the elements shown and described may be designed, configured, formed, modified, or implemented apart from the examples shown or described and are not limited to those provided.

Figure 4E:
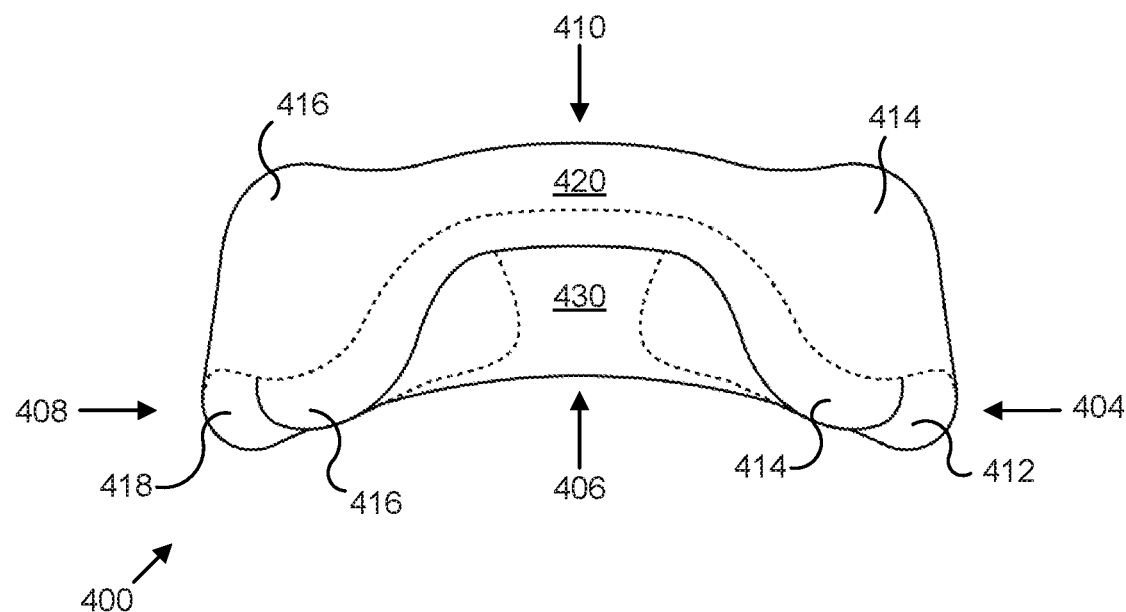
FIG. 4E illustrates a left view of an exemplary implantable interpositional orthopedic pain management apparatus.

FIG. 4E illustrates a left view of an exemplary implantable interpositional orthopedic pain management apparatus. Here, a left view of device 400 includes saddle channel openings 404-410, peripheral protrusions 412-418 disposed in periphery 420, and interpositional saddle surface 430. As used herein, like numbered and/or like named elements are assumed to be referencing the same or a substantially similar element having the same or substantially similar function or structure. Differences in function or structure may be described separately with regard to a specific feature described. In some examples, interpositional saddle surface 430 may be implemented on the bottom (i.e., underside, underneath, or the like) of device 400. A channel may be formed with interpositional saddle surface 430 and saddle channel openings 406 and 410. As shown, a channel disposed in device 400 using interpositional saddle surface 430 may be configured to receive a bone, bone structure, or portion thereof when surgical implantation occurs.

In some examples, when device 400 is surgically implanted, peripheral protrusions 412-418 provide structures along periphery 420 that are configured to maintain device 400 in a given joint (i.e., prevent expulsion of device 400), provide dynamic stability in the given joint, and alleviate pain by preventing bones, bone structures, or portions thereof from contacting each other as a replacement for missing, damaged, worn, or otherwise degraded cartilage within a joint or synovial capsule. As shown and described, peripheral protrusions 412-418 may be configured to provide outer perimeter walls that are devoid of contours such as those discussed above in connection with FIGS. 3A-3G. In other examples, peripheral protrusions 412-418 may be implemented with different structures (e.g., contours) apart from those shown and described. For example, peripheral protrusions 412-418 may alternatively have convex or concave structures formed within them to provide features to maintain device 400 within a joint, provide dynamic stability, maintain positioning of device 400 within a synovial capsule and/or joint, increase or protect ranges of motion, alleviate or prevent pain due to bone contact, or others. Still further, peripheral protrusions 412-418 may be varied in quantity, placement, location, position, or other attributes relative to periphery 420. As another example, peripheral protrusions 412-418 may be varied in the number of protrusions disposed and formed with periphery 420. In still other examples, device 400 and the elements shown and described may be designed, configured, formed, modified, or implemented apart from the examples shown or described and are not limited to those provided.

Figure 4F:
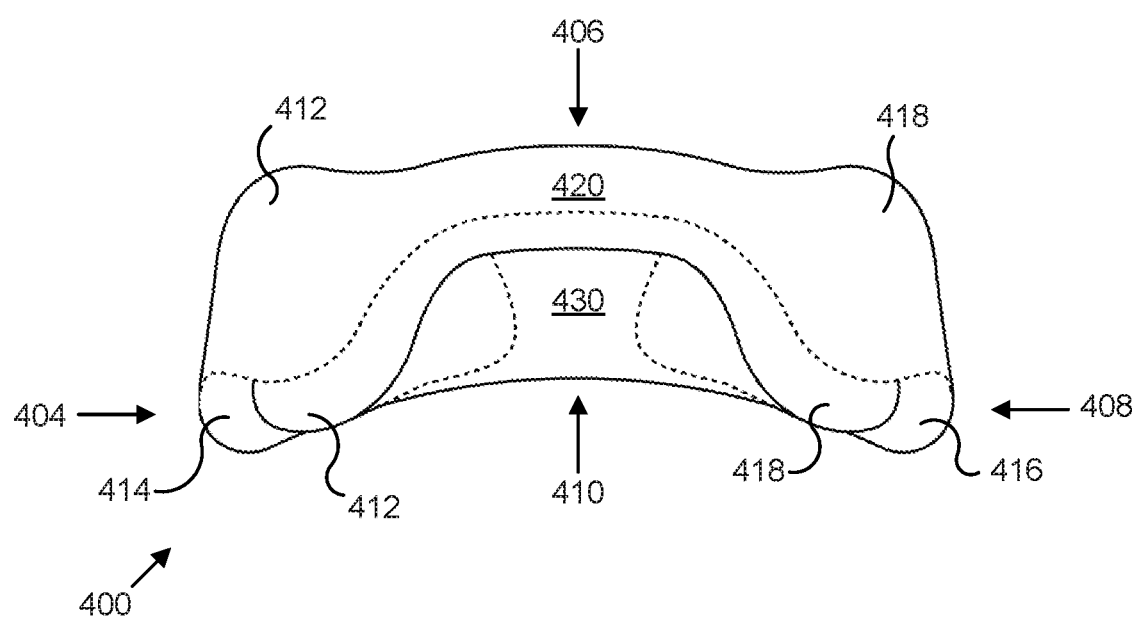
FIG. 4F illustrates a right view of an exemplary implantable interpositional orthopedic pain management apparatus.

FIG. 4F illustrates a right view of an exemplary implantable interpositional orthopedic pain management apparatus. Here, a right view of device 400 includes saddle channel openings 404-410, peripheral protrusions 412-418 disposed in periphery 420, and interpositional saddle surface 430. As used herein, like numbered and/or like named elements are assumed to be referencing the same or a substantially similar element having the same or substantially similar function or structure. Differences in function or structure may be described separately with regard to a specific feature described. As shown, saddle channel opening 410 indicates an opening to a channel formed with interpositional saddle surface 430 and saddle channel opening 406, the latter of which being indicated by a directional arrow pointed to the rear of device 400. As shown herein (as well as other drawings above and below), a directional arrow for saddle channel opening is directed at an opening having a radius of curvature implemented with interpositional saddle surface 430, which is configured to receive a bone, bone structure, or portion thereof such as a trapezium bone in a CMC joint. As with the other examples throughout this description, various radii of curvature may be used and are not limited to the examples shown and described. For example, an orthopedic surgeon (not shown) may receive a kit having one or more devices similar or substantially similar to device 400. Various devices may be formed using different radii of curvature in order to provide a range of options for a surgeon to determine which device (e.g., device 400) would be suited or appropriately sized for a given joint. Further, as discussed in greater detail below, trial devices (hereafter referred to as "trials") may be implemented examples of device 400 of different sizes (e.g., having varied or different dimensions), but also have a stem that may be manipulated for testing the placement and position of a device within a given joint. In some examples, a trial may also be used to probe a synovial capsule or joint in order to determine one or more attributes (e.g., size, dimensions, depth, width, tension, resistance, presence or lack of cartilage, and others, without limitation or restriction).

Referring back to FIG. 4F, device 400 may be implemented without contours or other features on the outer most perimeter of periphery 420. In alternative examples, contours or other features may be used and are not limited to those shown and described. In still other examples, device 400 and the elements shown and described may be designed, configured, formed, modified, or implemented apart from the examples shown or described and are not limited to those provided.

Figure 4G:
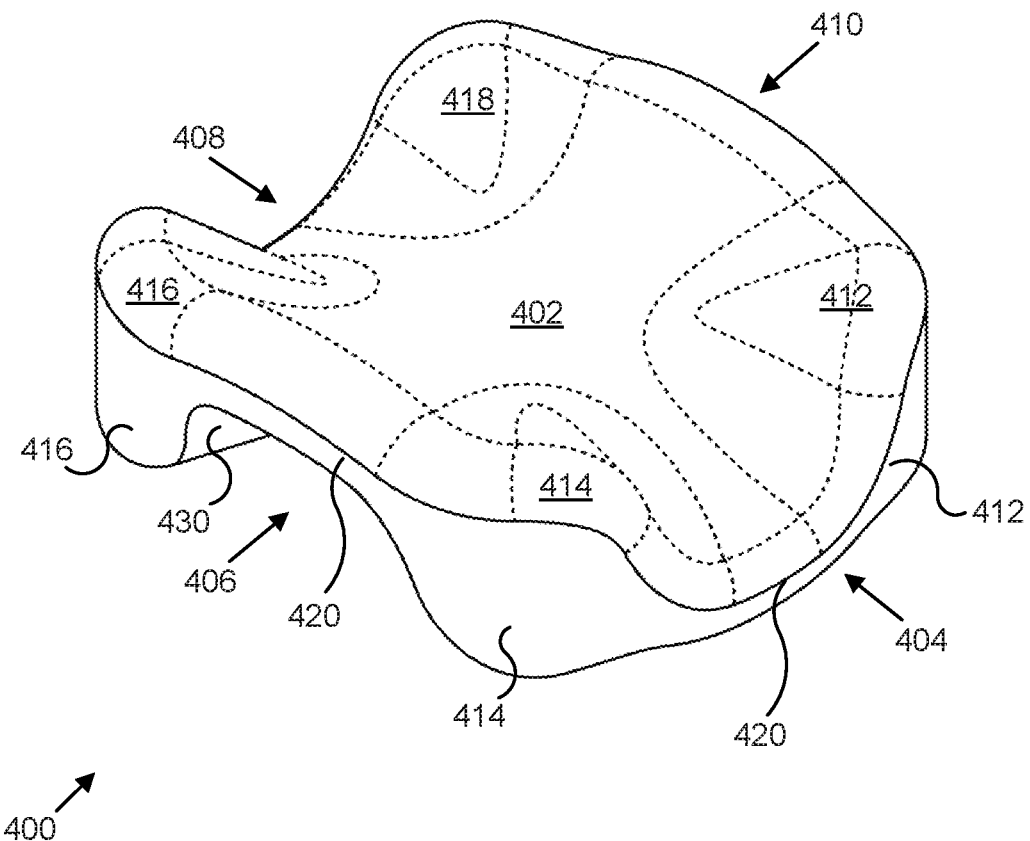
FIG. 4G illustrates a perspective view of an exemplary implantable interpositional orthopedic pain management apparatus.

FIG. 4G illustrates a perspective view of an exemplary implantable interpositional orthopedic pain management apparatus. Here, device 400 includes interpositional saddle surface 402, saddle channel openings 404-410, peripheral protrusions 412-418 disposed in periphery 420, and interpositional saddle surface 430. As used herein, like numbered and/or like named elements are assumed to be referencing the same or a substantially similar element having the same or substantially similar function or structure. Differences in function or structure may be described separately with regard to a specific feature described. In some examples, device 400 includes peripheral protrusions 412-418, which may be formed with or without features such as contours (e.g., contours 340-346 (FIGS. 3A-3G)). As shown and described herein, peripheral protrusions 412-416 are illustrated with upper and lower portions (peripheral protrusion 418 is shown with an upper portion based on the perspective view angle) that are intended to convey the integration of peripheral protrusions 412-418 with interpositional saddle surfaces 402 and 430 in device 400. Further, broken lines are provided to illustrate exemplary contouring and shaping of peripheral protrusions 412-418 as each is formed shape-wise into interpositional saddle surface 402. While periphery 420 is identified as a separate element, one, some, or all of peripheral protrusions 412-418 may be integrated portions that are part of periphery 420. In other examples, periphery 420 may be formed by directly or indirectly coupling peripheral protrusions 412-418, which may be formed with or apart from device 400. In other examples, device 400 and the elements shown and described may be designed, configured, formed, modified, or implemented apart from the examples shown or described and are not limited to those provided.

Figure 5A:
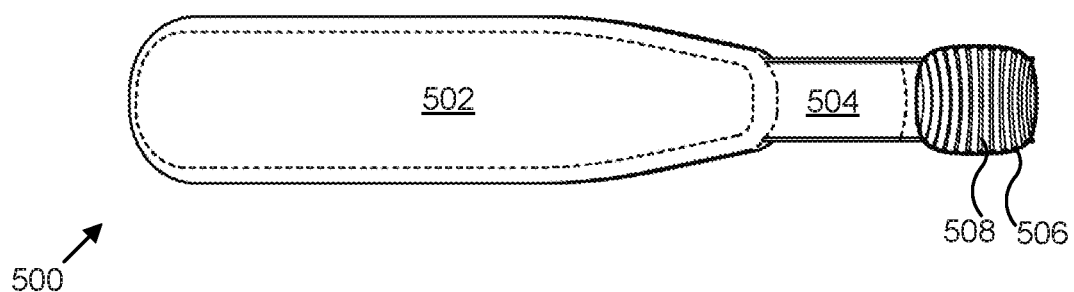
FIG. 5A illustrates a top view of an exemplary rasping instrument used for implantable interpositional orthopedic pain management.

FIG. 5A illustrates a top view of an exemplary rasping instrument used for implantable interpositional orthopedic pain management. Here, instrument 500 includes handle 502, neck 504, rasp 506, and teeth 508. As used herein, like numbered and/or like named elements are assumed to be referencing the same or a substantially similar element having the same or substantially similar function or structure. Differences in function or structure may be described separately with regard to a specific feature described. In some examples, instrument 500 may be used to prepare a path for surgical insertion (i.e., implantation) of device 100 (FIGS. 1A-1G), 200 (FIGS. 2A-2G), 300 (FIGS. 3A-3G), 400 (FIGS. 4A-4G), or others. Using handle 502, which is coupled to rasp 506, a user (e.g., orthopedic surgeon, or others) may prepare a joint for insertion of an implantable device, examples of which are provided and discussed herein. As an example, rasp 506 may be implemented (i.e., formed, manufactured, shaped, or otherwise formed) to have a larger radius of curvature than a device (hereafter "device" may refer to any of the exemplary implantable devices shown and described herein). Rasp 506 may be implemented with teeth 508, which may be rasping ridges, cutting ridges, cutting teeth, saw teeth, cutting rows, or the like. As an example, rasp 506 with teeth 508 may be used to "rasp" or modify a joint prior to insertion and implanting of a device. Instrument 500 and the elements may be constructed of various types of materials, such as those described above. In other examples, device 500 and the elements shown and described may be designed, configured, formed, modified, or implemented apart from the examples shown or described and are not limited to those provided.

Figure 5B:
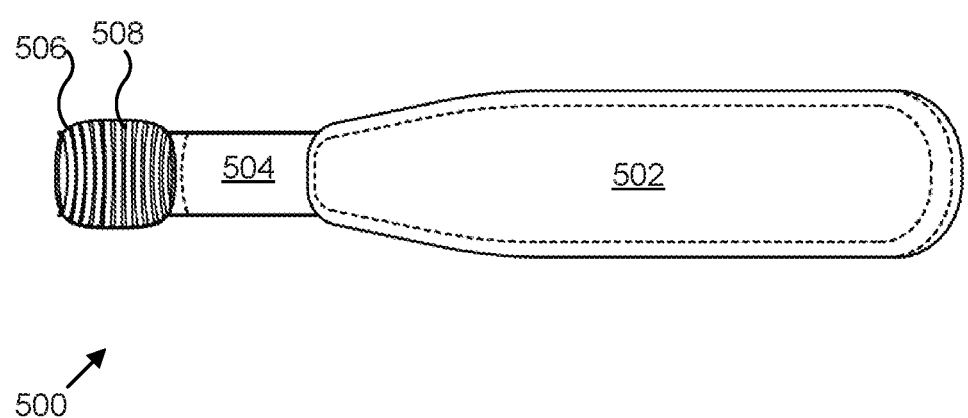
FIG. 5B illustrates a bottom view of an exemplary rasping instrument used for implantable interpositional orthopedic pain management.

FIG. 5B illustrates a bottom view of an exemplary rasping instrument used for implantable interpositional orthopedic pain management. Here, instrument 500 includes handle 502, neck 504, rasp 506, and teeth 508. As used herein, like numbered and/or like named elements are assumed to be referencing the same or a substantially similar element having the same or substantially similar function or structure. Differences in function or structure may be described separately with regard to a specific feature described. As shown and described, instrument 500 may be configured with rasp 506, which may have a radius of curvature that is slightly larger than a device to be implanted and may be substantially similar in shape to a device. In other words, rasp 506 may be formed in size, shape, and configuration similar to a device intended for implantation. When instrument 500 is used to modify or rasp a joint, the substantial similarity in size, shape, and configuration aids implantation of a device. In other examples, instrument 500 and the elements shown and described may be designed, configured, formed, modified, or implemented apart from the examples shown or described and are not limited to those provided.

Figure 5C:
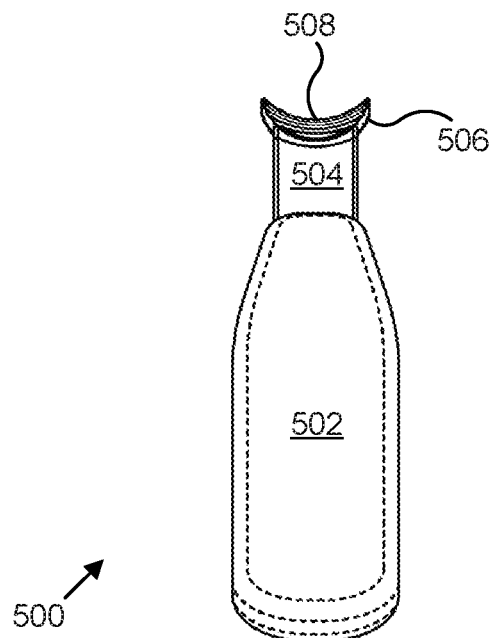
FIG. 5C illustrates an anterior view of an exemplary rasping instrument used for implantable interpositional orthopedic pain management.

FIG. 5C illustrates an anterior view of an exemplary rasping instrument used for implantable interpositional orthopedic pain management. Here, instrument 500 includes handle 502, neck 504, rasp 506, and teeth 508. As used herein, like numbered and/or like named elements are assumed to be referencing the same or a substantially similar element having the same or substantially similar function or structure. Differences in function or structure may be described separately with regard to a specific feature described. In other examples, instrument 500 and the elements shown and described may be designed, configured, formed, modified, or implemented apart from the examples shown or described and are not limited to those provided.

Figure 5D:
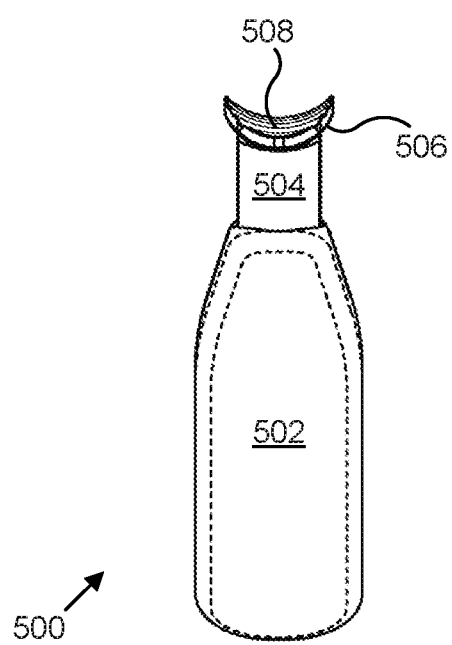
FIG. 5D illustrates a posterior view of an exemplary rasping instrument used for implantable interpositional orthopedic pain management.

FIG. 5D illustrates a posterior view of an exemplary rasping instrument used for implantable interpositional orthopedic pain management. Here, instrument 500 includes handle 502, neck 504, rasp 506, and teeth 508. As used herein, like numbered and/or like named elements are assumed to be referencing the same or a substantially similar element having the same or substantially similar function or structure. Differences in function or structure may be described separately with regard to a specific feature described. In other examples, instrument 500 and the elements shown and described may be designed, configured, formed, modified, or implemented apart from the examples shown or described and are not limited to those provided.

Figure 5E:
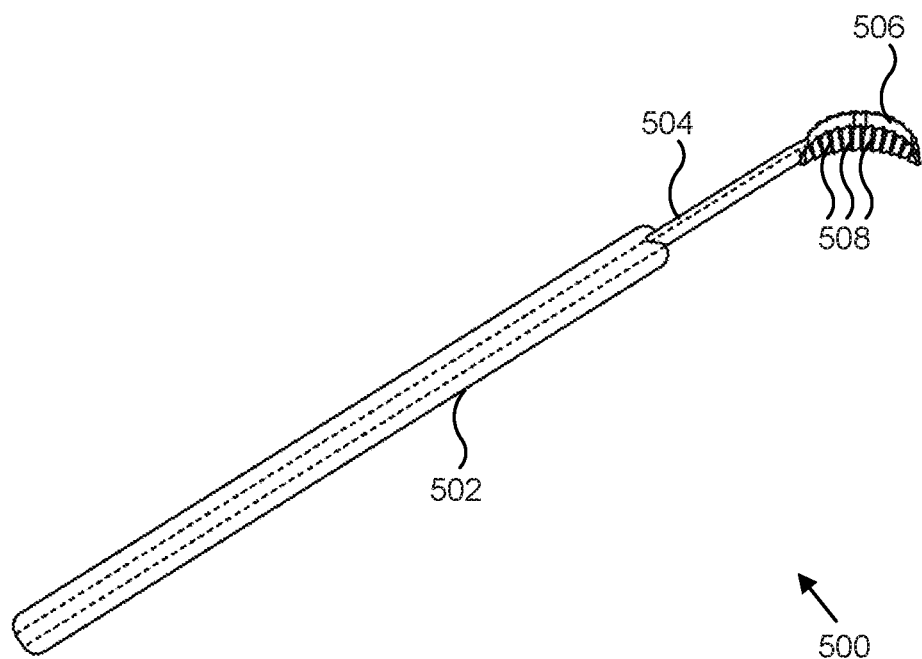
FIG. 5E illustrates a left view of an exemplary rasping instrument used for implantable interpositional orthopedic pain management.

FIG. 5E illustrates a left view of an exemplary rasping instrument used for implantable interpositional orthopedic pain management. Here, instrument 500 includes handle 502, neck 504, rasp 506, and teeth 508. As used herein, like numbered and/or like named elements are assumed to be referencing the same or a substantially similar element having the same or substantially similar function or structure. Differences in function or structure may be described separately with regard to a specific feature described. In other examples, instrument 500 and the elements shown and described may be designed, configured, formed, modified, or implemented apart from the examples shown or described and are not limited to those provided.

Figure 5F:
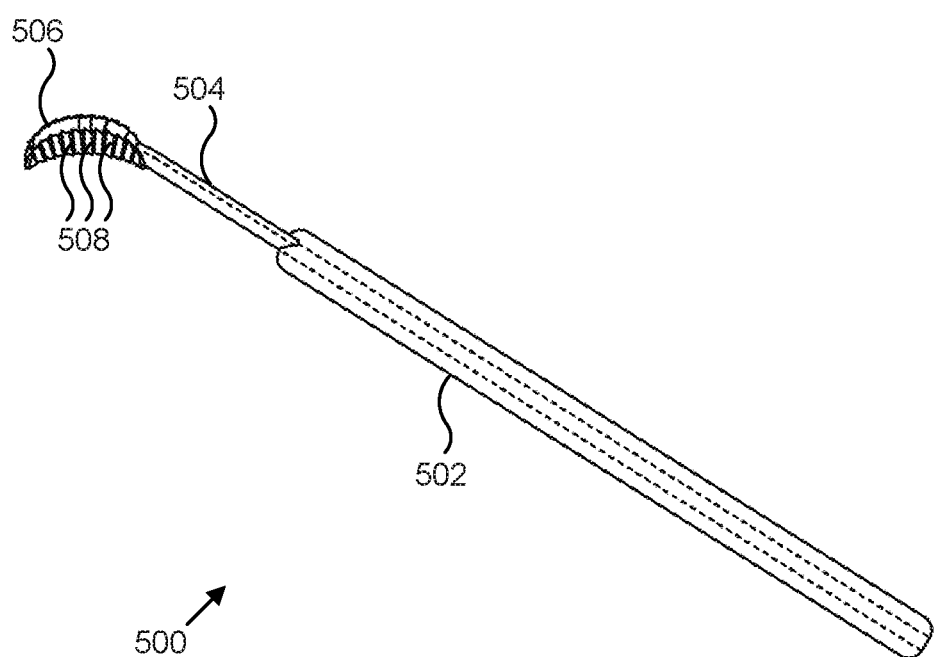
FIG. 5F illustrates a right view of an exemplary rasping instrument used for implantable interpositional orthopedic pain management.

FIG. 5F illustrates a right view of an exemplary rasping instrument used for implantable interpositional orthopedic pain management. Here, instrument 500 includes handle 502, neck 504, rasp 506, and teeth 508. As used herein, like numbered and/or like named elements are assumed to be referencing the same or a substantially similar element having the same or substantially similar function or structure. Differences in function or structure may be described separately with regard to a specific feature described. In other examples, instrument 500 and the elements shown and described may be designed, configured, formed, modified, or implemented apart from the examples shown or described and are not limited to those provided.

Figure 5G:
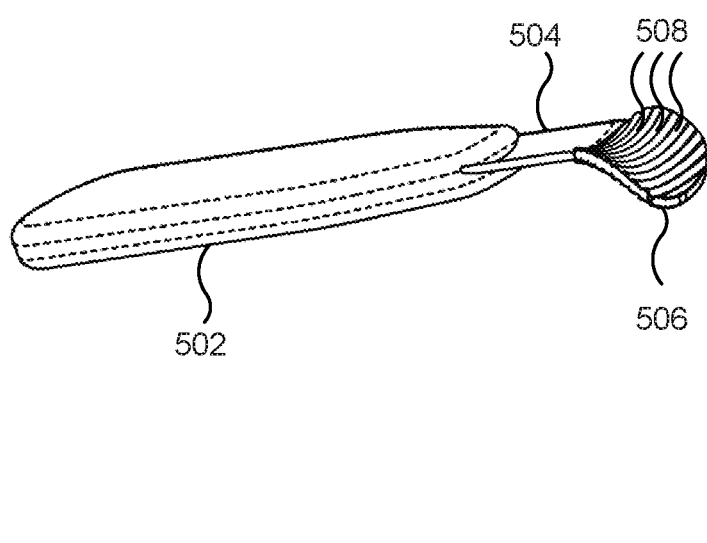
FIG. 5G illustrates a perspective view of an exemplary rasping instrument used for implantable interpositional orthopedic pain management.

FIG. 5G illustrates a perspective view of an exemplary rasping instrument used for implantable interpositional orthopedic pain management. Here, instrument 500 includes handle 502, neck 504, rasp 506, and teeth 508. As used herein, like numbered and/or like named elements are assumed to be referencing the same or a substantially similar element having the same or substantially similar function or structure. Differences in function or structure may be described separately with regard to a specific feature described. In other examples, instrument 500 and the elements shown and described may be designed, configured, formed, modified, or implemented apart from the examples shown or described and are not limited to those provided.

Figure 6A:
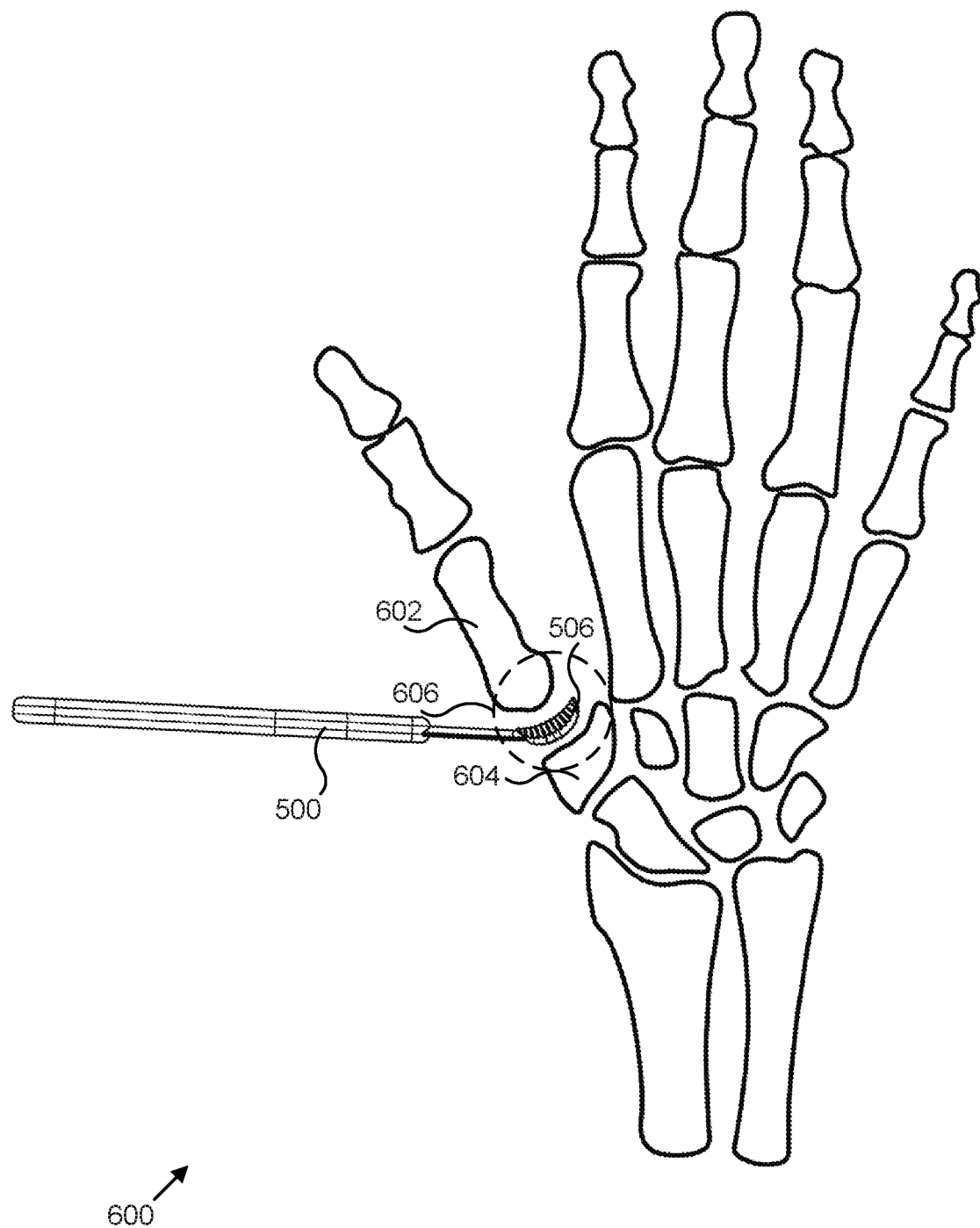
FIG. 6A illustrates an exemplary rasping instrument used for implantable interpositional orthopedic pain management.

FIG. 6 illustrates an exemplary rasping instrument used for implantable interpositional orthopedic pain management. Here, diagram 600 illustrates a basic skeletal structure of a human hand (in other examples, the skeletal structure of an animal other than homo sapiens may be used) having metacarpal bone 602, trapezium bone 604, and joint 606. As used herein, like numbered and/or like named elements are assumed to be referencing the same or a substantially similar element having the same or substantially similar function or structure. Differences in function or structure may be described separately with regard to a specific feature described. As described above in connection with FIGS. 5A-5G, rasping instrument 500 with rasp 506 is shown disposed between metacarpal 602 and trapezium 604 forming joint 606. As shown here, rasping instrument 500 may be used to clear, abrade, rasp, or otherwise modify the CMC joint between metacarpal 602 and trapezium 604 for the purpose of path preparation into joint 606 prior to surgical implantation of a device (e.g., device 100 (FIGS. 1A-1G), device 200 (FIGS. 2A-2G), device 300 (FIGS. 3A-3G), device 400 (FIGS. 4A-4G); not shown here). In other examples, rasping instrument 500 may be used to modify joints other than a CMC joint (e.g., joint 606) and is not limited to those shown and described. As presented herein, a joint (e.g., joint 606) targeted for surgical implantation of a device such as those described herein may be prepared (i.e., have a path prepared) by rasping out a path in joint 606 into which a trial or device may be inserted. Surgeons (i.e., users) of rasping instrument 500 may prepare a path for surgical implantation of an interpositional orthopedic pain management device such as those described herein, regardless of the type of joint targeted for modification. In other examples, path preparation may also be performed using more or different tools other than rasping instrument 500 (and rasp 506) and are not limited to the examples shown and described. In other examples, rasping instrument 500 as depicted in diagram 600 and the elements shown and described may be designed, configured, formed, modified, or implemented apart from the examples shown or described and are not limited to those provided.

Figure 6B:
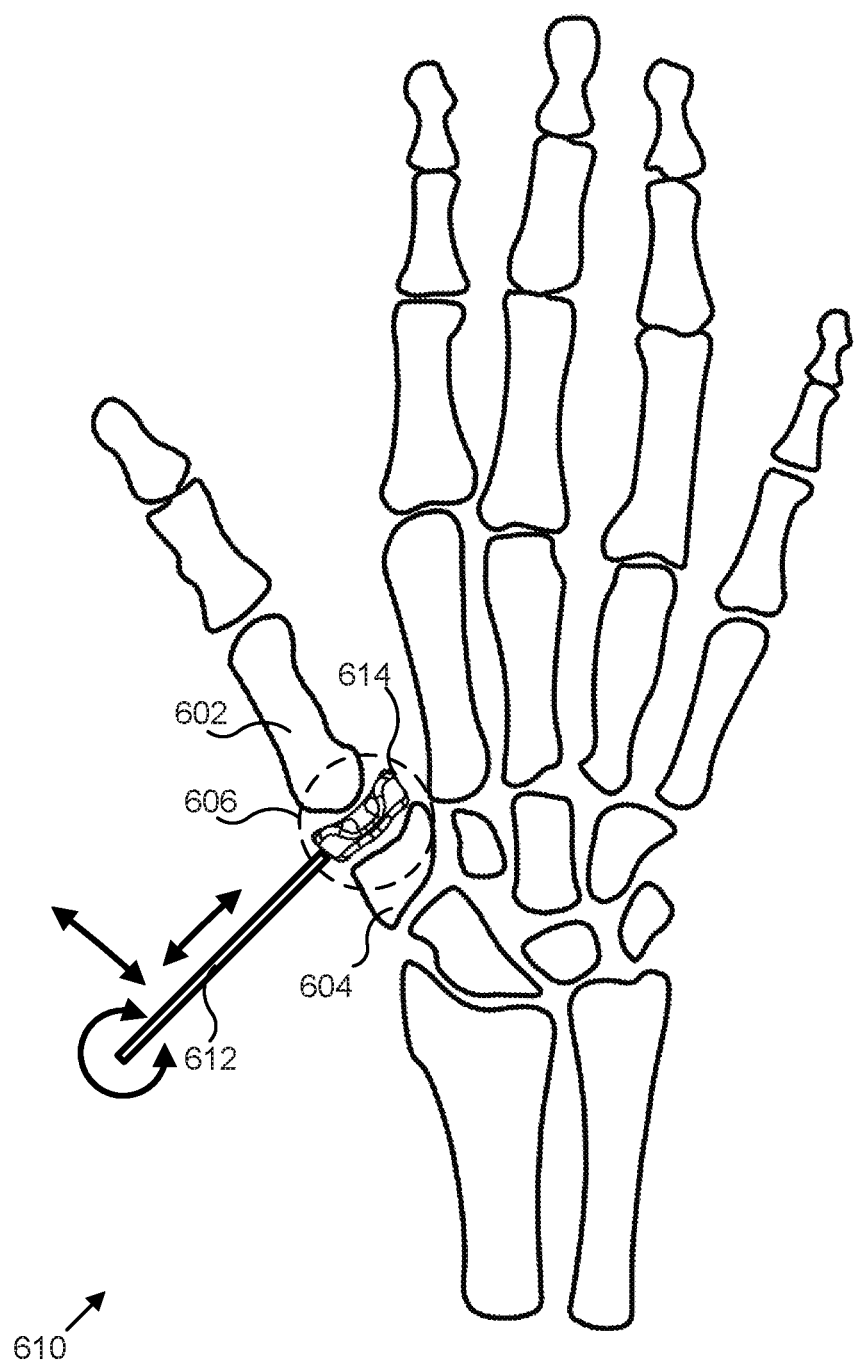
FIG. 6B illustrates an exemplary placement of an implantable interpositional orthopedic pain management device in a carpometacarpal joint.

FIG. 6B illustrates an exemplary placement of an implantable interpositional orthopedic pain management device in a carpometacarpal joint. Here, diagram 610 depicts metacarpal bone (i.e., "metacarpal") 602, trapezium bone (i.e., "trapezium") 604, joint 606, trial 612, and trial device 614. As used herein, like numbered and/or like named elements are assumed to be referencing the same or a substantially similar element having the same or substantially similar function or structure. Differences in function or structure may be described separately with regard to a specific feature described. In some examples, after path preparation (as described above in connection with FIG. 6A) has been performed, trial 612 (i.e., a stem coupled to trial device 614, which may be used for purposes of identifying a size of an implantable device targeted for surgical implantation into joint 606, such as those described above) may be inserted into joint 606 to determine whether additional path preparation is desired and, once completed, a size for an implantable device. As shown and described, trial 612 may be formed with trial device 614. In some examples, trial 614 may be welded, integrated with, incorporated into, or otherwise attached to a stem of trial 612. Here, when trial 612 is manipulated by a surgeon or other user, a stem may be provided to formed of various types of materials, such as those described above, and is not limited to the type, manner of formation or manufacturing, or shape. For example, a stem of trial 612 may be an elongated handle having a rounded, circular, oval, square, rectangular, or other type of cross section. Further, a stem of trial 612 may be rigid, flexible, malleable, or have other attributes intended to provide ease of manipulation of trial device 614 during path preparation and fitting (i.e., "sizing" or determining a size for an implantable device based on joint 606). As described herein, trial 612 may be manipulated in various directions to test ranges of motion for trial 614, as indicated by the various arrows provided for generally indicating directional manipulation of device 612, without limitation or restriction to degree, angle, or direction.

As used herein, trial 612 may be one of several trials included in a surgical kit having one or more implantable devices (e.g., device 100 (FIGS. 1A-1G), device 200 (FIGS. 2A-2G), device 300 (FIGS. 3A-3G), device 400 (FIGS. 4A-4G); not shown here). Trial 612 and other trials not shown may be included in a kit intended for reuse or disposal, but after being used to identify a suitable size of an implantable device (not shown) for insertion into joint 606. As shown, trial device 614 may be shaped, configured, or otherwise formed similarly or substantially similarly to a device (not shown) intended for surgical implantation. Trial 612 and other trials used provide the ability to determine a suitable size for an implantable device without requiring excessive trial and error (i.e., attempting to surgically implant disparate implantable devices), which can not only be time and cost-consuming, but also incur risks associated with unnecessary tissue, ligament and ligature, and tendon stress or damage. In other examples, trial 612 as depicted in diagram 610 and the elements shown and described may be designed, configured, formed, modified, or implemented apart from the examples shown or described and are not limited to those provided.

Figure 6C:
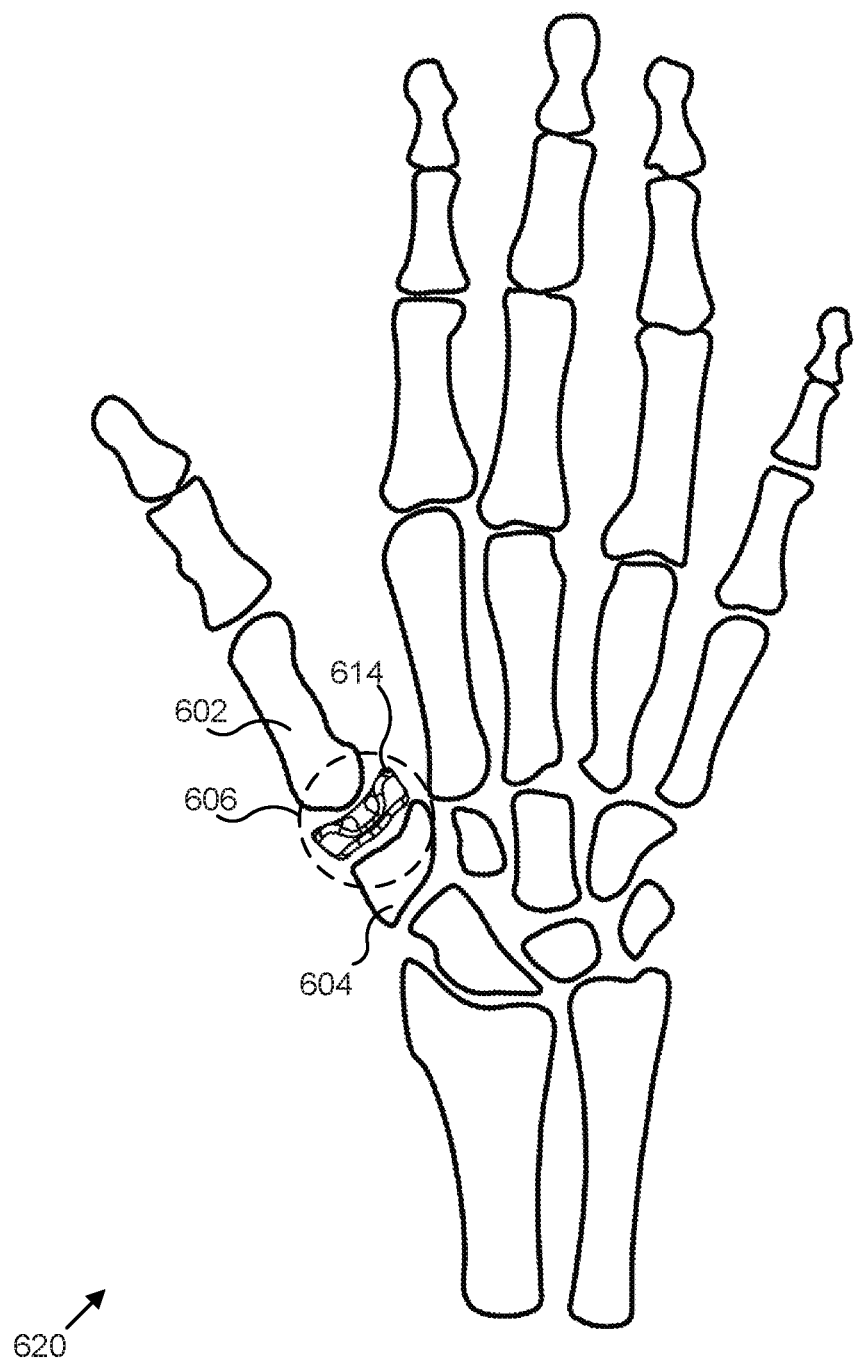
FIG. 6C illustrates an exemplary placement of an implantable interpositional orthopedic pain management device in a carpometacarpal joint.

FIG. 6C illustrates an exemplary placement of an implantable interpositional orthopedic pain management device in a carpometacarpal joint. Here, diagram 620 depicts metacarpal bone (i.e., "metacarpal") 602, trapezium bone (i.e., "trapezium") 604, joint 606, trial 612, and device 622. As used herein, like numbered and/or like named elements are assumed to be referencing the same or a substantially similar element having the same or substantially similar function or structure. Differences in function or structure may be described separately with regard to a specific feature described. In some examples, device 622 may be surgically implanted in joint 606 between metacarpal 602 and trapezium 606. However, in other examples, device 622 and others as described above (e.g., device 100 (FIGS. 1A-1G), device 200 (FIGS. 2A-2G), device 300 (FIGS. 3A-3G), device 400 (FIGS. 4A-4G); not shown here) may be used for surgical implantation in other human or animal joints, without limitation or restriction, using the techniques and tools described herein. In other examples, device 622 as depicted in diagram 610 and the elements shown and described may be designed, configured, formed, modified, or implemented apart from the examples shown or described and are not limited to those provided.

Figure 7A:
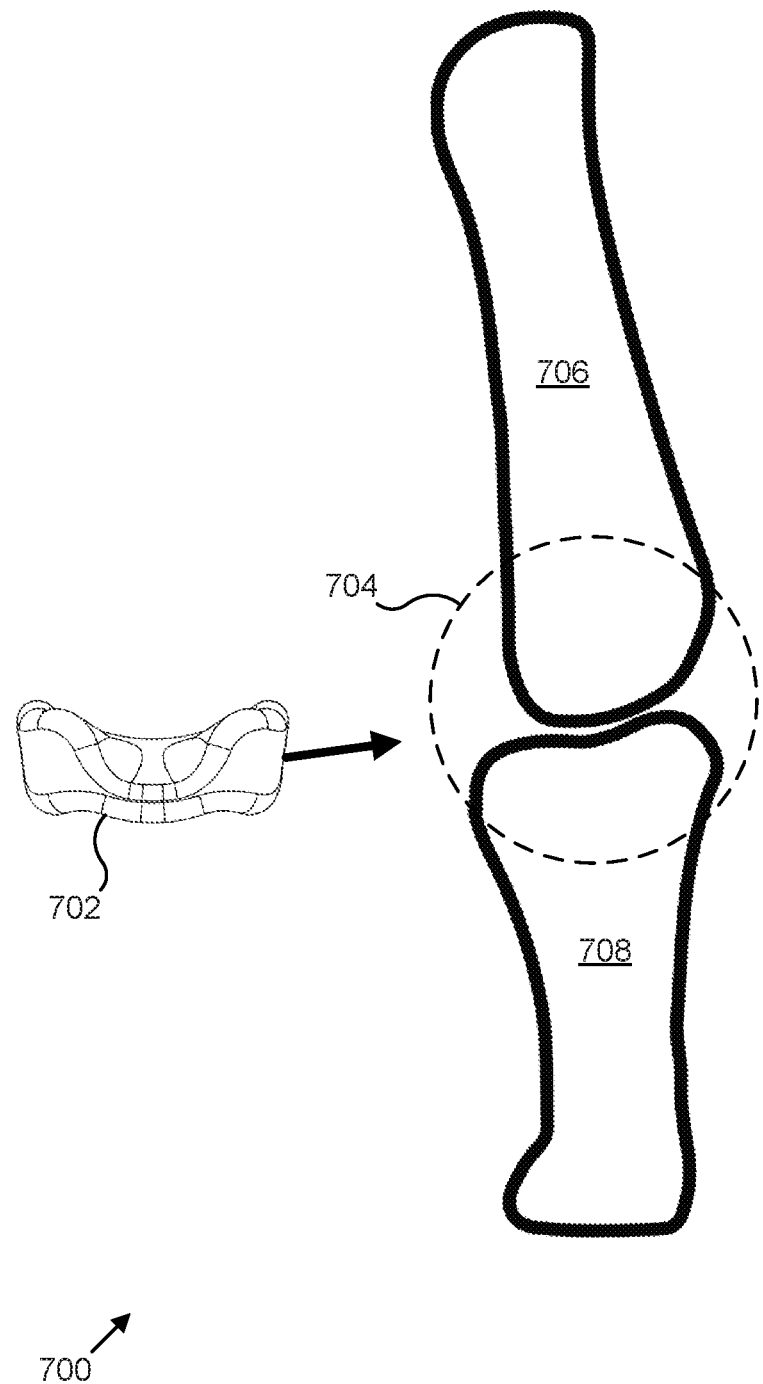
FIG. 7A illustrates another exemplary placement of an implantable interpositional orthopedic pain management device in a carpometacarpal joint.

FIG. 7A illustrates another exemplary placement of an implantable interpositional orthopedic pain management device in a bone joint. Here, diagram 700 illustrates a general illustration of device 702 being configured for insertion into joint 704 between bones 706-708. As used herein, like numbered and/or like named elements are assumed to be referencing the same or a substantially similar element having the same or substantially similar function or structure. Differences in function or structure may be described separately with regard to a specific feature described. In some examples, device 702 may be of varying dimensions, shapes, sizes, or other attributes, including modification for joints other than a CMC joint. Here, joint 704 is provided as a basic illustration of a joint in which multiple bones (e.g., bones 706-708) are positioned against each other, but without any intervening material (e.g., cartilage or other bone structures). Device 702 may be formed of varying size and shape to be used, as described herein, for insertion between bones 706-708 to provide the functions provided and described elsewhere. Although bones 706-708 are shown, joint 704 may include other bones or bone structures beyond those shown and described.

As shown, joint 704 between bones 706-708 may lack cartilage, in which case, device 702 may be surgically implanted to prevent contact resulting in pain (i.e., pain relief and management). In other examples, device 702 may be surgically implanted into joint 704 between bones 706-708 to prevent dislocation and, once inserted, features such as those described above in connection with various implementations of an implantable device may be used to prevent expulsion of device 702 from joint 704. In other examples, device 702 as depicted in diagram 700 and the elements shown and described may be designed, configured, formed, modified, or implemented apart from the examples shown or described and are not limited to those provided.

Figure 7B:
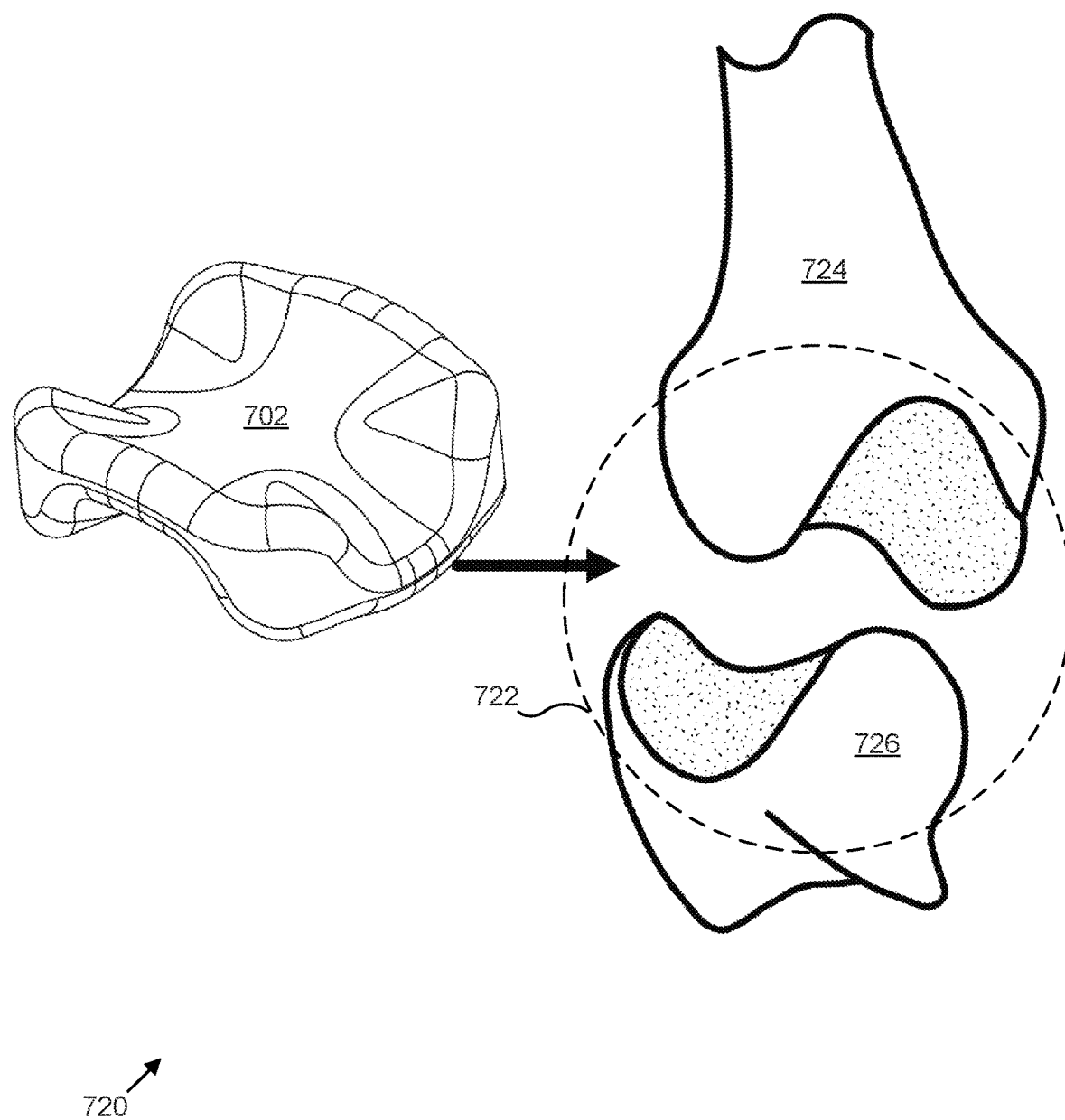
FIG. 7B illustrates a further exemplary placement of an implantable interpositional orthopedic pain management device in a carpometacarpal joint.

FIG. 7B illustrates a further exemplary placement of an implantable interpositional orthopedic pain management device in a bone joint. Here, diagram 720 provides a three-dimensional oriented view (i.e., perspective view) of surgically implanting device 702 into joint 722 between bones 724 and 726, which are not limited or restrictive to only those of the CMC joint. As used herein, like numbered and/or like named elements are assumed to be referencing the same or a substantially similar element having the same or substantially similar function or structure. Differences in function or structure may be described separately with regard to a specific feature described. For example, bones 724 and 726 may be representative of those found in a knee joint (e.g., femur and tibia) and device 722 may be used to replace worn, damaged, aged, missing, or otherwise incapacitated cartilage that is no longer sufficiently structured or functionally able to provide dynamic stability to joint 722, enable range of motion, or alleviate pain when bones 724-726 physically contact each other. In other examples, device 702 as depicted in diagram 720 and the elements shown and described may be designed, configured, formed, modified, or implemented apart from the examples shown or described and are not limited to those provided.

Figure 7C:
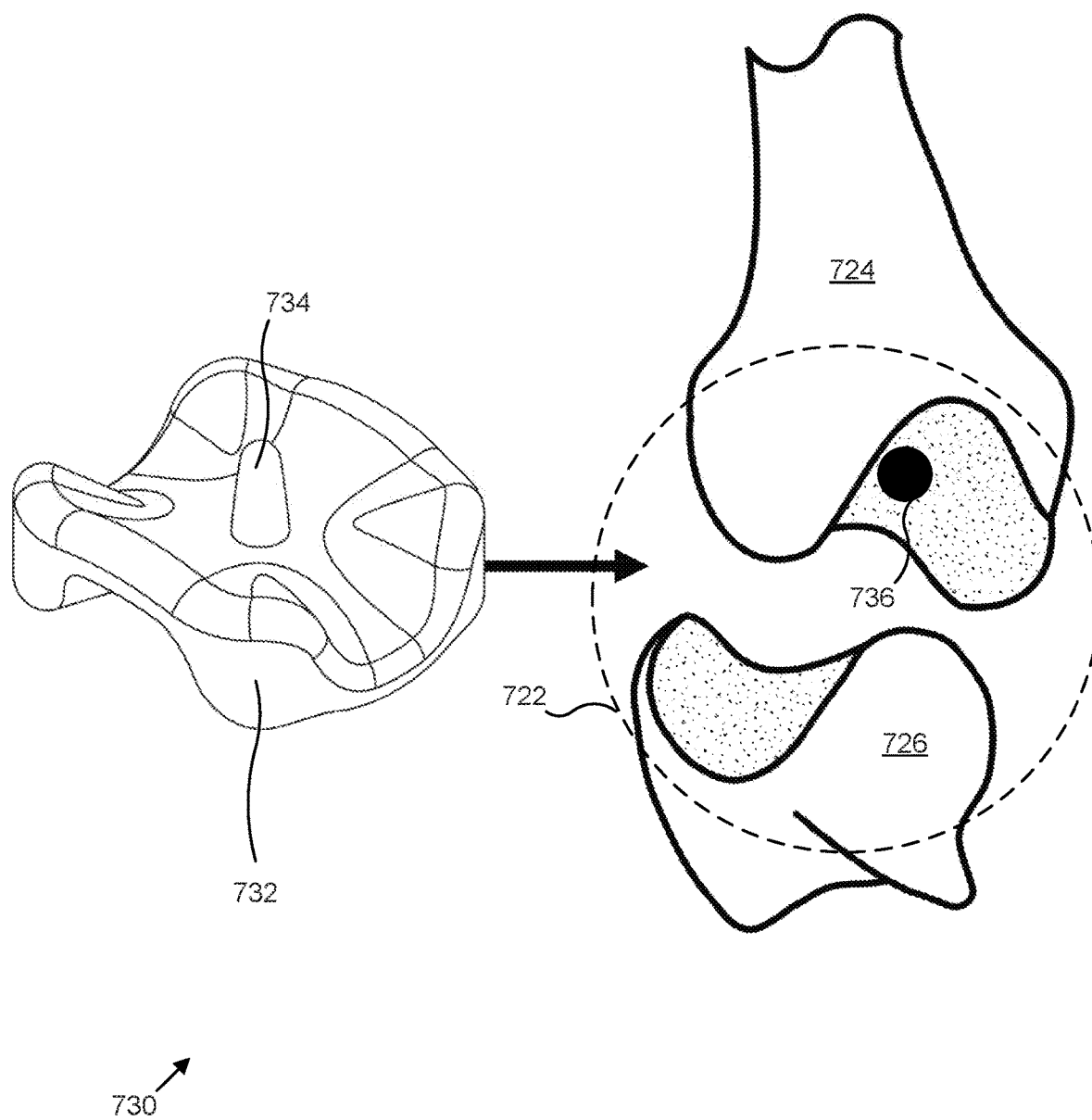
FIG. 7C illustrates yet another exemplary placement of an implantable interpositional orthopedic pain management device in a bone joint.

FIG. 7C illustrates yet another exemplary placement of an implantable interpositional orthopedic pain management device in a bone joint. Here, diagram 730 provides a three-dimensional oriented view (i.e., perspective view) of surgically implanting device 732 into joint 722 between bones 724 and 726, anchor structure 734 and anchor recess 736. As described above, joint 722 is not limited to a specific joint or type of joints, examples of which are provided for purposes of illustration and explanation. As used herein, like numbered and/or like named elements are assumed to be referencing the same or a substantially similar element having the same or substantially similar function or structure. Differences in function or structure may be described separately with regard to a specific feature described.

As described above, device 732 may be implemented similar to other devices (e.g., device 100 (FIGS. 1A-1G), device 200 (FIGS. 2A-2G), device 300 (FIGS. 3A-3G), device 400 (FIGS. 4A-4G)). In some examples, device 732 may also be varied to include elements other than those described herein (e.g., peripheral protrusions, periphery, opposing interpositional saddle surfaces, or others). As shown here, device 732 may be implemented with anchor structure 734, which may be an extra or different element configured to be placed, positioned, or otherwise inserted into anchor recess 736 to provide, among other uses, a point of fixation to bone 724 within joint 722. In some examples, when inserted into anchor recess 736, anchor structure 734 may be used to prevent device 732 from a loss or degradation of position or orientation, dislodgement, or expulsion from joint 722. Further, anchor structure 734 may also be used to prevent one or both of bones 724-726 (which may be any type of bone surrounding any type of joint, as used herein) from becoming dislocated from joint 722. In other examples, anchor structure 734 may be designed, configured, or implemented differently and is not limited to the shape, structure, or function as described herein. For example, anchor structure 734 may have different shapes or other structures, such as protrusions, corners, recesses, or other elements that are configured to fit within anchor recess 736. In still other examples, anchor recess 736 may not be present and bone 724 may instead be configured to receive anchor structure 734 (e.g., which may be implemented as a bump, protrusion, nub, or other type of raised surface or structure (which may or may not be coupled directly or indirectly or formed with device 73)), which have a penetrating or sharp edge that may be pressed into bone 724 without a pre-configured or pre-cut recess or receptacle such as anchor recess 736. In still other examples, device 732 and/or anchor structure 734 may be configured differently and is not limited to the examples shown or described herein.

For example, device 732 may be designed, configured, or implemented differently. In some examples, a stem or substrate, which may be disposed on one or more sides of a joint, may be implemented with one or more peripheral protrusions to be used with or without anchor structure 734 or anchor recess 736. A stem (not shown) may be a substantially flat, smooth, sharp, shortened, elongated, or other shape apart from those shown and described, but when coupled (directly or indirectly) to one or more peripheral protrusions (e.g., peripheral protrusions 112-118 (FIGS. 1A-1G), 212-218 (FIGS. 2A-2G), 312-318 (FIGS. 3A-3G), 412-418 (FIGS. 4A-4G), or others, without limitation or restriction) or other structures (e.g., anchor structure 734) may be used to provide the functions as described herein, including, but not limited to pain relief, pain management, cartilaginous replacement/supplement/augmentation, prevention of dislocation, and others. In other examples, device 732 as depicted in diagram 730 and the elements shown and described may be designed, configured, formed, modified, or implemented apart from the examples shown or described and are not limited to those provided.

Figure 8:
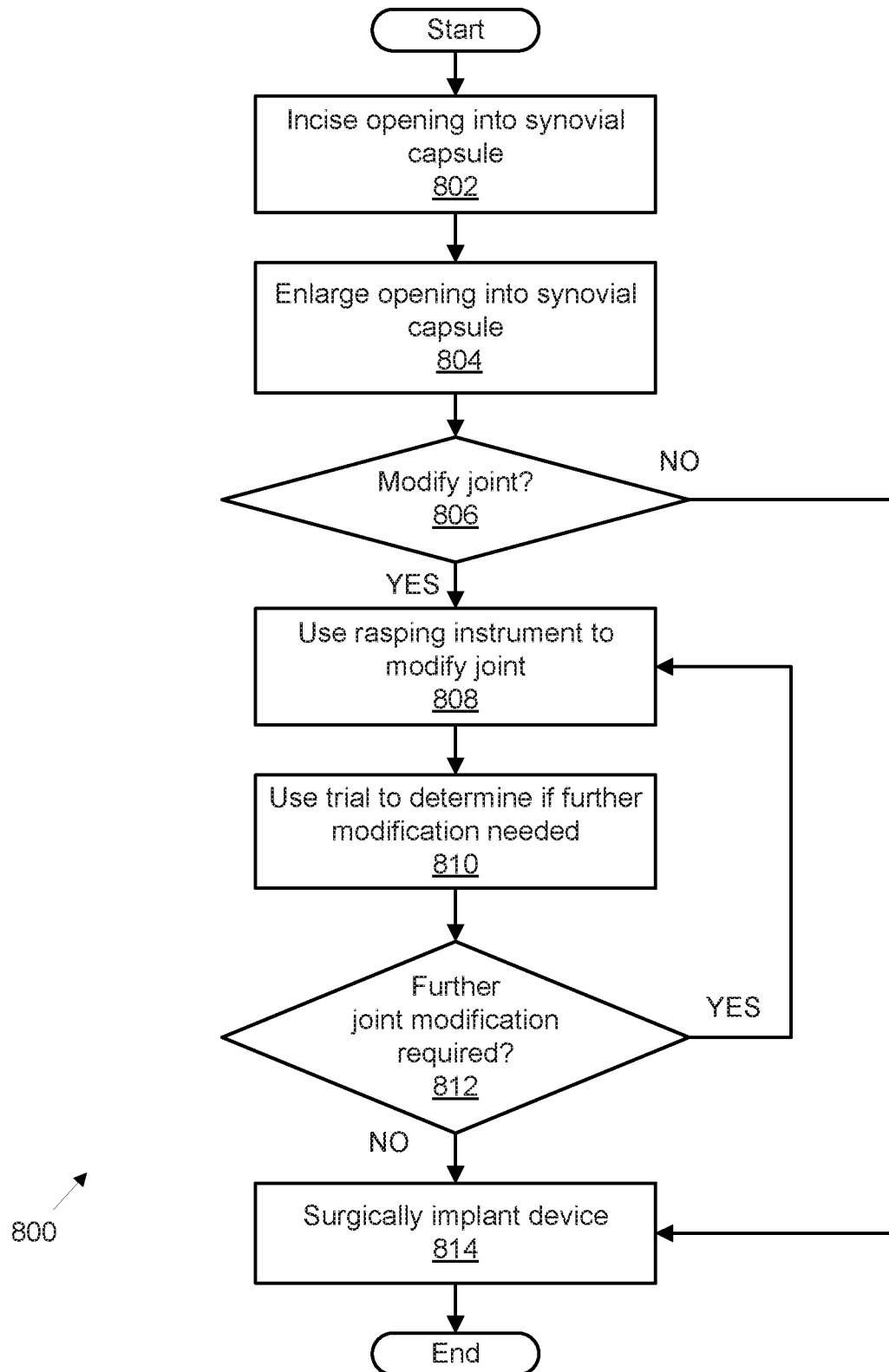
FIG. 8 illustrates an exemplary surgical technique for implantable interpositional orthopedic pain management.

FIG. 8 illustrates an exemplary surgical technique for implantable interpositional orthopedic pain management. Here, process 800 begins by incising (i.e., making an incision) into a synovial capsule surrounding a joint (802). Once an incision (i.e., an opening) has been made, the opening into a synovial capsule may be enlarged using, for example, a trocar or other cutting tool designed for surgically enlarging an incision (804). A determination is then made to determine whether the joint require modification due to obstructions or restrictions such as an osteophyte, abnormal bone growth, or other skeletal structure or substructure that may obstruct the articulation of an implantable device (e.g., device 100 (FIGS. 1A-1G), device 200 (FIGS. 2A-2G), device 300 (FIGS. 3A-3G), device 400 (FIGS. 4A-4G), or any other implementation of said devices having one or more peripheral protrusions and other features as described herein) once positioned within a joint (806). If modification is desired, a rasping instrument (e.g., rasping instrument 500 (FIGS. 5A-5G)) may be used to rasp or remove/cut away obstructions within a joint in order to permit insertion, articulation, and non-obstruction of a device once surgically implanted (808).

After rasping or modifying a joint, a trial (e.g., trial 612 (FIG. 6B)) may be inserted into the joint through the enlarged opening to determine if further modification (e.g., additional modification using, for example, rasping instrument 500 (FIGS. 5A-5G)) is desired (810). A determination is then made using a trial as to whether further modification of the joint is required (812). In some examples, if further modification is desired, then rasping instrument 500 (FIGS. 5A-5G) may be used (808) and trial 612 (FIG. 6B) is again inserted to determine if various attributes are within tolerances and/or thresholds for surgical implantation of a device (e.g., device 100 (FIGS. 1A-1G), device 200 (FIGS. 2A-2G), device 300 (FIGS. 3A-3G), device 400 (FIGS. 4A-4G)) (810). However, if modification of a joint is not required, then a device may be surgically implanted and the process ends (814). In other examples, process 800 and the sub-processes or processes shown and described may be designed, configured, performed, ordered, reordered, or otherwise implemented differently than the examples shown or described and are not limited to those provided.

Figure 9:
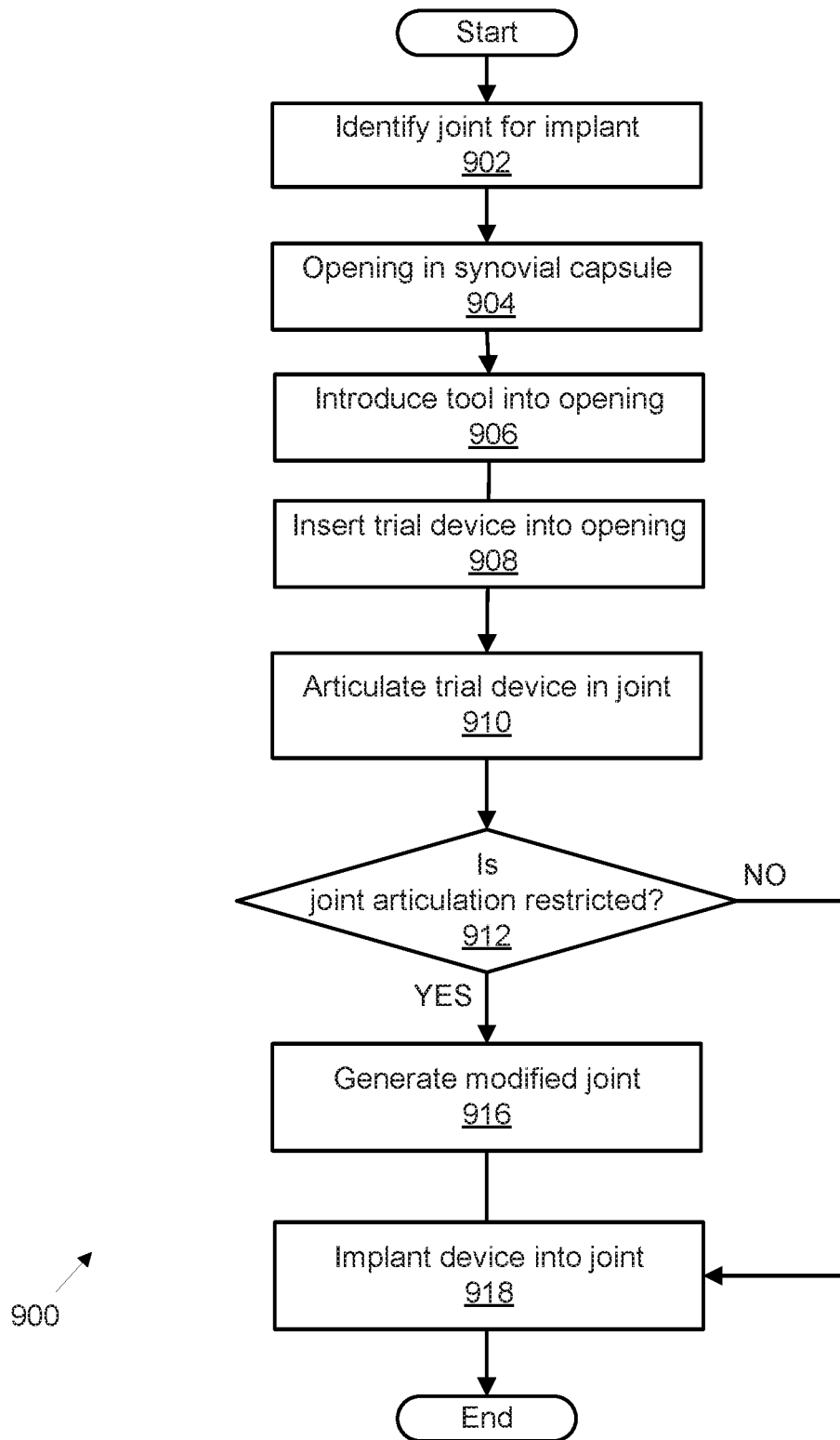
FIG. 9 illustrates another exemplary surgical technique for implantable interpositional orthopedic pain management.

FIG. 9 illustrates another exemplary surgical technique for implantable interpositional orthopedic pain management. Here, alternate process 900 begins by identifying a joint for implantation using a device (e.g., device 100 (FIGS. 1A-1G), device 200 (FIGS. 2A-2G), device 300 (FIGS. 3A-3G), device 400 (FIGS. 4A-4G)) (902). After identifying a joint for implantation, an opening is made into a synovial capsule surrounding the joint (e.g., CMC joint) (904). Next, a tool may be introduced into the opening (e.g., scalpel, trocar, or other cutting tools) to enlarge the initial incision (906). Once the opening/incision has been enlarged, a trial (e.g., trial 612 (FIG. 6B)) is inserted into the joint to determine one or more attributes (e.g., size, position, orientation, and others, without limitation or restriction) (908). In order to aid determination of the one or more factors, the trial device is articulated. In some examples, trial 612 may be articulated using, for example, a stem molded, adhered, attached, or otherwise coupled, directly or indirectly, to a trial device (e.g., trial device 614 (FIG. 6B)) (910). By articulating trial 612, a determination may be made to identify whether any obstructions, restrictions, or limitations are present in the joint (912). For example, osteophytes (i.e., abnormal bone growth or bone structures within a joint) may form into a joint that could prohibit an implantable device (e.g., device 100 (FIGS. 1A-1G), device 200 (FIGS. 2A-2G), device 300 (FIGS. 3A-3G), device 400 (FIGS. 4A-4G)) from articulating fully within a given range of motion, or prohibit articulation of bones adjacent to the joint once surgical implantation has occurred.

In some examples, if a determination is made that a joint is restricted in its ability to articulate, then modification of the joint may be desired and performed using, for example, surgical instruments such as rasping instrument 500 (FIGS. 5A-5G) (916). Once modified or, in the alternative, if no obstruction, restriction, or limitation to articulation of a target joint was detected in step 912, then a device may be surgically implanted into the joint (918) and process 900 ends. In other examples, process 900 and the sub-processes or processes shown and described may be designed, configured, performed, ordered, reordered, or otherwise implemented differently than the examples shown or described and are not limited to those provided.

Figure 10:
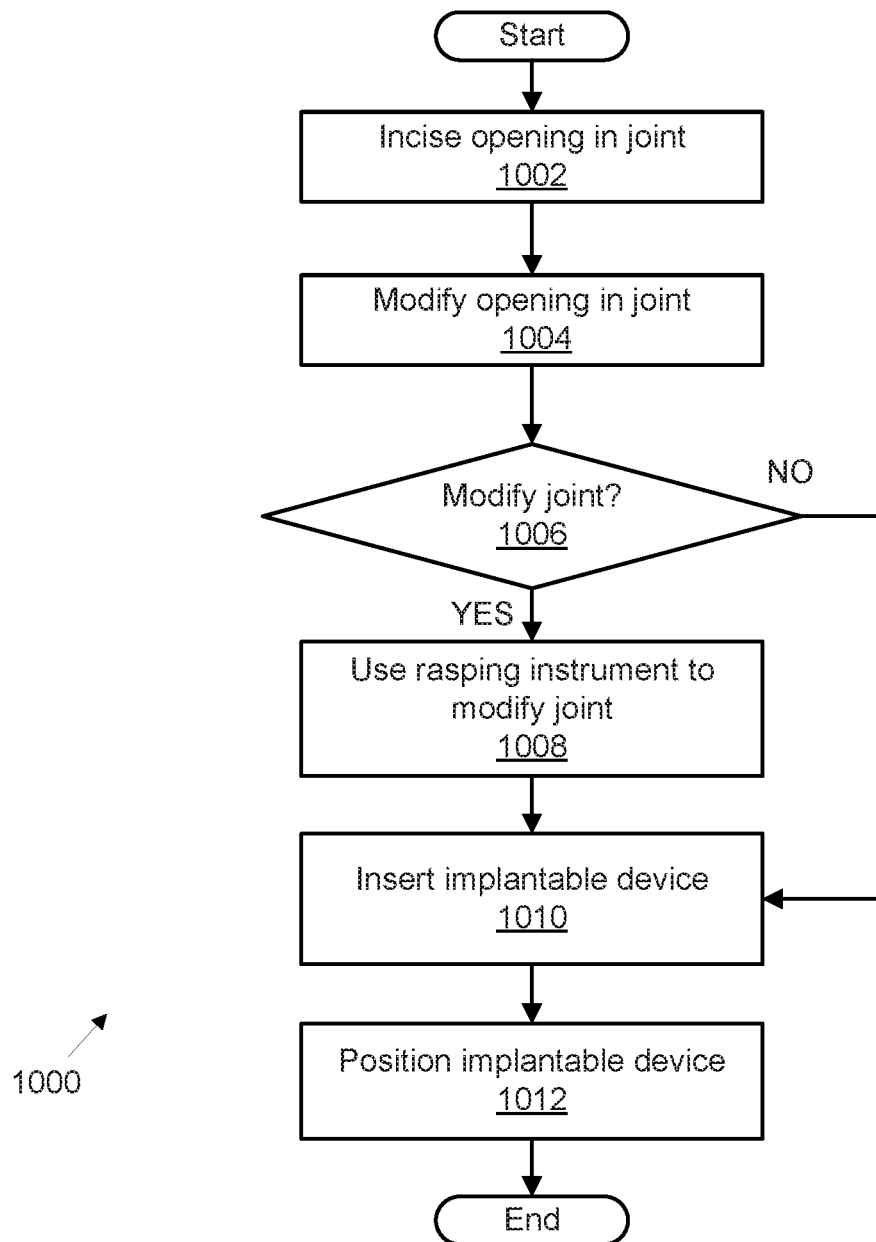
FIG. 10 illustrates an exemplary surgical technique for implantable interpositional orthopedic pain management.

FIG. 10 illustrates an exemplary surgical technique for implantable interpositional orthopedic pain management. Here, process 1000 begins by incising an opening into a joint (1002). Once incised, the opening is modified (i.e., enlarged) (1004). As described herein, various surgical tools and techniques may be used to enlarge the incision, without limitation or restriction, to any particular technique. In some examples, a determination is made as to whether a joint or bones forming the joint need to be modified in order to permit implantation, positioning, and unimpeded (i.e., unobstructed, unrestricted) articulation of a device (e.g., device 100 (FIGS. 1A-1G), device 200 (FIGS. 2A-2G), device 300 (FIGS. 3A-3G), device 400 (FIGS. 4A-4G)) once surgically implanted in a joint (1006). If modification of a joint is required, then a rasping instrument (e.g., rasping instrument 500 (FIGS. 5A-5G)) may be used to modify the joint by removing obstructions, rasping or cutting down osteophytes or other bone growth or bone structures (1008). Once modified or if no modification is required, a device may be surgically implanted (1010). Once inserted, a device may be positioned in order to position peripheral protrusions, such as those described above, to permit articulation of the joint, demonstration of dynamic stability, and restoration (either immediately or a gradual restoration) of strength and range of motion, among other benefits (1012). In other examples, process 1000 and the sub-processes or processes shown and described may be designed, configured, performed, ordered, reordered, or otherwise implemented differently than the examples shown or described and are not limited to those provided.

Figure 11:
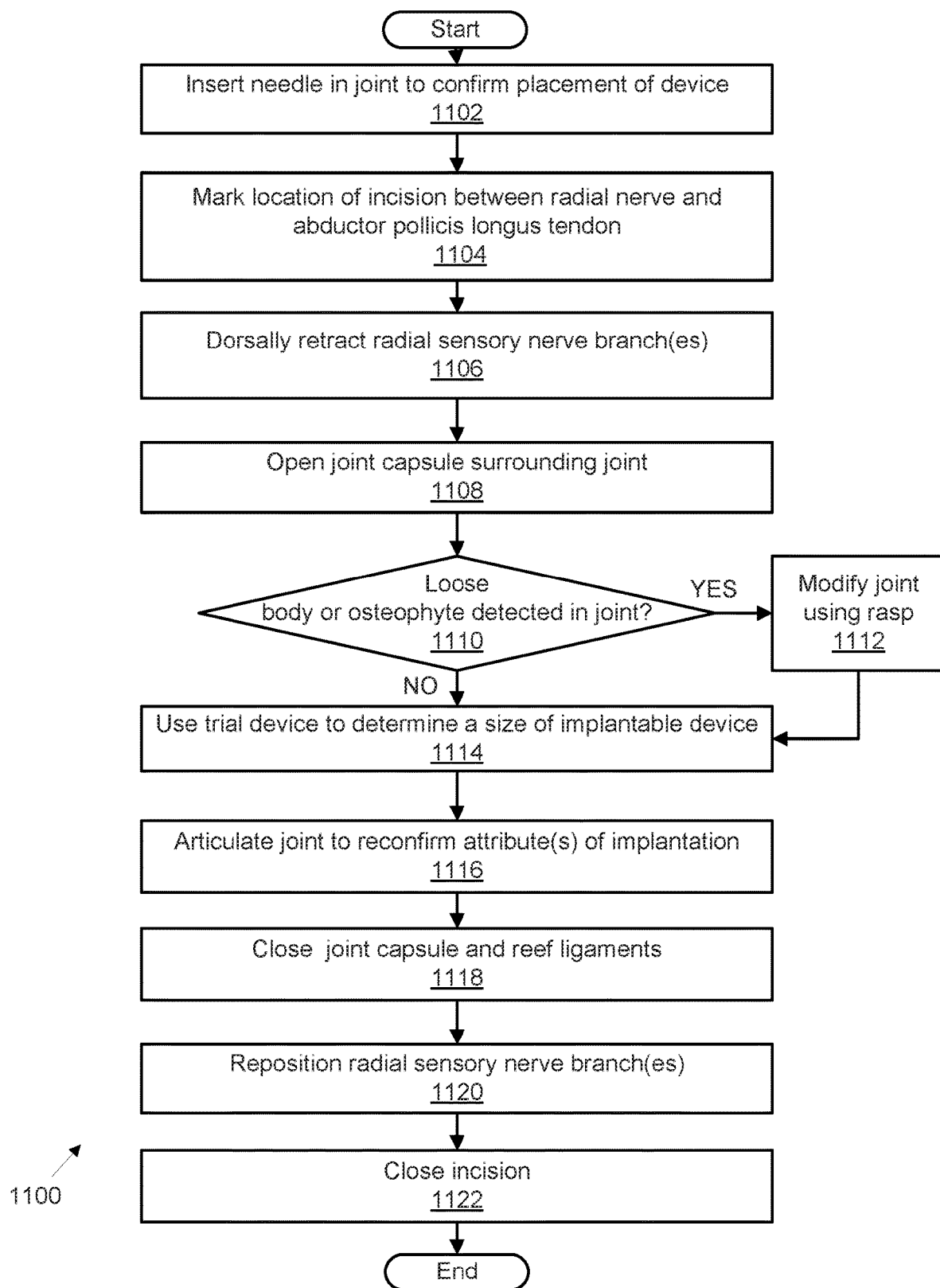
FIG. 11 illustrates yet another exemplary surgical technique for implantable interpositional orthopedic pain management.

FIG. 11 illustrates yet another exemplary surgical technique for implantable interpositional orthopedic pain management. Here, process 1100 begins by inserting a needle into a joint to confirm placement of a device (1102). After determining the intended position of a surgically implanted device (e.g., device 100 (FIGS. 1A-1G), device 200 (FIGS. 2A-2G), device 300 (FIGS. 3A-3G), device 400 (FIGS. 4A-4G)), a location for an initial incision is marked (1104). In some examples, an incision performed for purposes of inserting a device (e.g., device 100 (FIGS. 1A-1G), device 200 (FIGS. 2A-2G), device 300 (FIGS. 3A-3G), device 400 (FIGS. 4A-4G)) into a CMC joint may be marked as running between the radial nerve and the abductor pollicis longus tendon ("APLT"), to avoid cutting, slicing, incising, or otherwise damaging either the radial nerve or the APLT. Generally, an incision should lie or fall between the radial nerve and the APLT. In other words, the radial nerve and the APLT may bracket either side of an incision as marked in this step. Once marked, one or more radial sensory nerve branches are dorsally retracted (1106). Next, a joint capsule (e.g., synovial capsule) surround a joint is opened (1108). A determination is then made as to whether a loose body (e.g., bone shard, loose cartilage, or other undesired tissue or bone remnants) or osteophytes are detected within a joint (1110). If detected, then rasping instrument 500 (FIGS. 5A-5G) may be used to rasp or cut osteophytes or remove loose objects within the joint (1112). In other examples, different types of surgical tools may be used and are not limited to the examples presented and discussed herein. If no loose bodies (i.e., objects) or osteophytes are detected within a joint, then a trial device may be used to determine a size of an implantable device (1114). Once inserted into a joint through an enlarged opening incised into a joint capsule, trial 612 (FIG. 6B) may be articulated to determine a size of a device (e.g., device 100 (FIGS. 1A-1G), device 200 (FIGS. 2A-2G), device 300 (FIGS. 3A-3G), device 400 (FIGS. 4A-4G)) ultimately intended for surgical implantation in a joint (1114).

After determining a size of a device to be surgically implanted into a joint, articulation may be performed with a trial inserted into the joint in order to reconfirm one or more attributes of implantation (1116). In some examples, attributes of implantation may include size, scale, orientation, position, or other factors for consideration when surgically implanting a device (e.g., device 100 (FIGS. 1A-1G), device 200 (FIGS. 2A-2G), device 300 (FIGS. 3A-3G), device 400 (FIGS. 4A-4G)). After reconfirming attributes associated with the surgically implanted device (i.e., "device"), the joint capsule may be closed and one or more ligaments reefed (1118). Radial sensory nerve branches may then be repositioned prior to closure (1120) and the initial incision is closed (1122). In other examples, process 1000 and the sub-processes or processes shown and described may be designed, configured, performed, ordered, reordered, or otherwise implemented differently than the examples shown or described and are not limited to those provided.

Although the foregoing examples have been described in various detail for purposes of clarity of understanding, the above-described inventive techniques and subject matter are not limited to the details provided. There are many alternative ways of implementing the above-described invention techniques. The disclosed examples are illustrative and not restrictive.

What is claimed:

1. An implantable device, comprising:
a substantially saddle-shaped body having a top contoured saddle surface and a bottom contoured saddle surface, the top contoured saddle surface being substantially orthogonal to the bottom contoured saddle surface, the body configured to axially align the top contoured saddle surface to a bone surface and to axially align the bottom contoured saddle surface to another bone surface and the body being configured to articulate with the bone surface and the another bone surface the top contoured saddle surface and the bottom contoured saddle surface including substantially orthogonal channels, the substantially orthogonal channels including a top channel and a bottom channel, the top contoured saddle surface having the top channel, and the bottom contoured saddle surface having the bottom channel, the top channel having a top length of curvature disposed horizontally traversed across the top contoured saddle surface, and the bottom channel having a bottom length of curvature disposed horizontally traversed across the bottom contoured saddle surfaces, such that the top length of curvature has an orientation that is substantially orthogonal to another orientation of the bottom length of curvature, each channel having channel openings, and the top and bottom channels extending between channel openings, the channel openings each being substantially concave, and each channel configured to receive one of the bone surface or the another bone surface to prevent the bone surface from contacting the another bone surface, and
a plurality of peripheral protrusions disposed on a periphery of the substantially saddle-shaped body, each of the plurality of peripheral protrusions located at a substantially corner position of the periphery; the peripheral protrusions shaped to extend in a direction of an end of the bone surface and configured to be in intermittent contact with the end of the bone surface, the peripheral protrusions being configured to permit motion of the bone surface and the another bone surface without dislocation of the body when movement of the body causes one or more of the plurality of peripheral protrusions to contact the bone surface or the another bone surface, maintain dynamic stability of the saddle-shaped body between the bone surface and the another bone surface, to prevent expulsion of the device from a cavity between the bone surface and the another bone surface, and to prevent physical contact between the bone surface and the another bone surface.

2. The implantable device of claim 1, wherein the dynamic stability comprises maintaining anatomical alignment of the implantable device when inserted into the cavity.

3. The implantable device of claim 1, wherein the dynamic stability comprises preventing the implantable device from being displaced, partially or entirely, from within a joint between the bone surface and the another bone surface.

4. The implantable device of claim 1, wherein the substantially saddle-shaped body and the peripheral protrusions are substantially formed using a material comprising pyrolytic carbon.

5. The implantable device of claim 1, wherein the substantially saddle-shaped body and the peripheral protrusions are formed using a material having one or more properties substantially similar to a property of cortical bone.

6. The implantable device of claim 1, wherein one or more dimensions associated with the substantially saddle-shaped body are configured to be determined using a ratio generated by comparing one or more other dimensions associated with the substantially saddle-shaped body, the peripheral protrusions, the periphery, and a joint formed between the bone surface and the another bone surface.

7. The implantable device of claim 1, wherein the peripheral protrusions are configured to prevent displacement of the implantable device from a joint formed between the bone surface and the another bone surface.

8. The implantable device of claim 1, wherein the peripheral protrusions are disposed on the periphery at locations at which the peripheral protrusions are configured to move the implantable device in a direction that is substantially opposite to a force transmitted by the bone surface or the another bone surface.

9. The implantable device of claim 1, wherein the peripheral protrusions are configured to prevent the implantable device from being displaced, partially or entirely, from a joint when movement between the bone surface and the another bone surface occurs.

10. The implantable device of claim 1, wherein the peripheral protrusions are formed along the periphery.

11. The implantable device of claim 1, wherein the peripheral protrusions are formed in the periphery, the peripheral protrusions being disposed at different positions along the periphery and configured to prevent the implantable device from being substantially dislodged from a joint formed between the bone surface and the another bone surface.

12. An implantable device, comprising:
a body having a cross sectional area that has a curvature attribute that is larger than another curvature attribute associated with a bone forming, with another bone, a joint into which the implantable device is inserted, the body having a top saddle surface and a bottom saddle surface, the top saddle surface being substantially orthogonal to the bottom saddle surface, the top saddle surface and the bottom saddle surface each having substantially orthogonal channels extending between channel openings, each channel opening located on a periphery of the body, the substantially orthogonal channels including a top channel and a bottom channel, the top saddle surface having the top channel and the bottom saddle surface having the bottom channel, the top channel having a top length of curvature disposed horizontally traversed across the top saddle surface, and the bottom channel having a bottom length of curvature disposed horizontally traversed across the bottom saddle surface, such that the top length of curvature has an orientation that is substantially orthogonal to another orientation of the bottom length of curvature, and the top and bottom channels extending between channel openings, the channel openings each being substantially concave; and
a plurality of peripheral protrusions, each of the plurality of peripheral protrusions being formed in a periphery of the body and disposed at substantially corner positions of the periphery such that each channel opening indicates an opening in between peripheral protrusions, and the plurality of peripheral protrusions being configured to be in intermittent contact with the bone or the another bone, to permit motion of the joint without dislocation of the body from the joint when at least one of the plurality of peripheral protrusions comes into contact with the bone or the another bone, and to prevent the bone from physically contacting the another bone.

13. The implantable device of claim 12, further comprising the body being configured to be inserted into a synovial capsule substantially located within the joint.

14. The implantable device of claim 12, wherein the cross sectional area is substantially concave while the body has another cross sectional area that is substantially orthogonal to the cross sectional area and the another cross sectional area is substantially convex.

15. The implantable device of claim 12, wherein the joint is a carpometacarpal joint.

16. An implantable device, comprising:
a body having a substantially saddle shape, the body having a top saddle surface and a bottom saddle surface, the top saddle surface being substantially orthogonal to the bottom saddle surface, the body being configured to articulate with a bone surface of a metacarpal and the another bone surface of a trapezium within a carpometacarpal joint, and being configured to be interpositionally placed within a carpometacarpal joint to substantially maintain the articulating orientation between the metacarpal and a trapezium, the top saddle surface having a top channel and the bottom saddle surface having a bottom channel, the top channel having a top length of curvature disposed horizontally traversed across the top saddle surface, and the bottom channel having a bottom length of curvature disposed horizontally traversed across the bottom saddle surface, such that the top length of curvature has an orientation that is substantially orthogonal to another orientation of the bottom length of curvature, each channel having channel openings, and the top and bottom channels extending between channel openings, the channel openings each being substantially concave; and
a plurality of peripheral nubs formed along a periphery of the body disposed at substantially corner positions of the periphery, each of the plurality of peripheral nubs being configured to substantially stabilize the implantable device and prevent expulsion of the device from the joint when movement of the body causes at least one of the peripheral nubs comes into contact with the bone surface of the metacarpal or the another bone surface of the trapezium when inserted in the carpometacarpal joint and to prevent the metacarpal from physically cotacting the trapezium when the carpometacarpal joint is articulated.

17. The implantable device of claim 16, wherein each of the plurality of peripheral nubs are configured to prevent expulsion of the implantable device when the metacarpal and the trapezium are articulated relative to each other.

18. The implantable device of claim 16, wherein each of the plurality of peripheral nubs are disposed on the periphery between a portion of the metacarpal and another portion of the trapezium and are configured to generate joint distraction between the metacarpal and the trapezium when the carpometacarpal joint is articulated.

19. The implantable device of claim 16, wherein each of the plurality of peripheral nubs are disposed on the periphery between a non-articulating portion of the metacarpal and another non-articulating portion of the trapezium and are configured to generate joint distraction between the metacarpal.

* * * * *